United States Patent [19]

Crowe et al.

[11] Patent Number: 5,368,391
[45] Date of Patent: Nov. 29, 1994

[54] METHOD AND APPARATUS FOR HIGH RESOLUTION ANALYSIS

[75] Inventors: Benjamin S. Crowe, Centerville; Steven R. Sauerbrunn, Wilmington, both of Del.

[73] Assignee: TA Instruments, Inc., New Castle, Del.

[21] Appl. No.: 979,168

[22] Filed: Nov. 18, 1992

Related U.S. Application Data

[60] Division of Ser. No. 663,106, Mar. 1, 1991, Pat. No. 5,165,792, which is a continuation-in-part of Ser. No. 638,847, Jan. 8, 1991, abandoned.

[51] Int. Cl.$^5$ .................... G01N 25/00; G01N 25/18
[52] U.S. Cl. ..................................... 374/10; 374/14; 374/43; 374/44; 374/45; 374/31; 374/141; 374/142
[58] Field of Search ............... 374/10, 14, 45, 43, 374/44, 31, 141, 142

[56] References Cited

U.S. PATENT DOCUMENTS

| | | | |
|---|---|---|---|
| 3,045,472 | 7/1962 | Paulik et al. | 374/10 |
| 3,271,996 | 9/1966 | Paulik et al. | 374/14 |
| 3,344,654 | 10/1967 | Erdey et al. | 374/14 |
| 3,519,547 | 7/1970 | Paulik et al. | 374/14 |
| 3,712,110 | 1/1973 | Paulik et al. | 374/12 |
| 3,839,903 | 10/1974 | Buehler | 374/45 |
| 3,902,354 | 9/1975 | Harlan et al. | 374/14 |
| 4,388,410 | 6/1983 | Arroyo et al. | 374/14 |
| 4,457,632 | 7/1984 | Collins et al. | 374/14 |
| 4,690,569 | 9/1987 | Veitch | 374/11 |
| 4,838,706 | 6/1989 | Coey et al. | 374/54 |

FOREIGN PATENT DOCUMENTS

| | | |
|---|---|---|
| 2139494 | 1/1973 | France . |
| 1283564 | 11/1968 | Germany ................. 374/14 |
| 2176011 | 12/1986 | United Kingdom . |
| 02856 | 4/1988 | WIPO . |

OTHER PUBLICATIONS

O. Toft Sorensen, "Thermogravimetric Studies of Non-Stoichiometric Cerium Oxides Under Isothermal and Quasi-Isothermal Conditions", Journal of Thermal Analysis, vol. 13, pp. 429–437 (1978).

G. M. Lukaszewski, "Accuracy in Thermogravimetric Analysis", Nature, vol. 194, No. 4832, pp. 959–961 (Jun. 1962).

(List continued on next page.)

Primary Examiner—William A. Cuchlinski, Jr.
Assistant Examiner—Diego F. F. Gutierrez
Attorney, Agent, or Firm—Kirkland & Ellis

[57] ABSTRACT

The present invention relates to analytical methods for determining the composition of a material that undergoes a transition as a function of a driving variable. As applied to thermogravimetric analysis (TGA), a first preferred embodiment comprises (1) decreasing the heating rate when deviations from a baseline signal are detected; (2) establishing a minimum heating rate; (3) forcing the heating rate to a predetermined maximum whenever the rate of change of the weight change with respect to the temperature falls below a predetermined value; and (4) adjusting the heating rate according to the rate of change of the weight of the sample to track a predetermined rate of change of the weight of the sample. A second preferred embodiment comprises (1) selecting either a high-productivity or a high-resolution mode; (2) in both modes, controlling the rate of temperature increase according to a function containing an exponential term, wherein the argument of the exponential term includes the percent weight change per unit time of the sample; (3) in the high-productivity mode, choosing the function so that when the percentage weight change per minute of the sample is small, the heating rate approaches the maximum allowed heating rate, and when the percentage weight change per minute is very large, the heating rate approaches zero; (4) in the high-resolution mode, choosing the function such that the heating rate is held at almost zero during a transition.

23 Claims, 35 Drawing Sheets

OTHER PUBLICATIONS

F. Paulik and J. Paulik, "Thermoanalytical Examination Under Quasi-Isothermal-Quasi-Isobaric Conditions", Thermochimica Acta, vol. 100, pp. 23-59 (1986).

J. Paulik and F. Paulik, "'Quasi-isothermal' thermogravimetry", Anal. Chim. Acta, vol. 56, pp. 328-331 (1971).

F. Paulik, J. Paulik, M. Arnold and R. Naumann, "Investigation on the Thermal Behaviour of $Mg(NO_3)hd 2 6H_2O$ I. The Decomposition Behaviour", J. Therm. Anal., vol. 34, pp. 627-635 (1988).

J. Paulik, F. Paulik and M. Arnold, "The Derivatograph-C. A microcomputer-controlled simultaneous TG, DTG, DTA, TD and EGA apparatus I", J. Therm. Anal., vol. 32, pp. 301-309 (1987).

J. Rouquerol, "Controlled Transformation Rate Thermal Analysis: The Hidden Face of Thermal Analysis", Thermochimica Acta, vol. 144, pp. 209-224 (1989).

J. Rouquerol, "Methode d'analyse thermique sous faible pression et a vitesse de decomposition constante", Memoires Presentes a la Societe Chimique, (Manuscript received on Oct. 24, 1963, listed as published in Jan. 1964), pp. 31-32.

M. Reading, D. Dollimore, J. Rouquerol and F. Rouquerol, "The Measurement of Meaningful Activation Energies Using thermoanalytical methods. A tentative proposal", J. Therm. Anal., vol. 29, pp. 775-785 (1984).

M. Reading, "The Kinetics of Heterogeneous Solid State Decomposition Reactions: A New Way Forward?", Int'l. Confed. of Therm. Analysis (1988).

J. Chiu, "Dynamic Thermal Analysis of Polymers. An Overview", J. Macromol, Sci-Chem., vol. A8(1), pp. 3-23 (1974).

J. Chiu, "Applications of Thermogravimetry to the Study of High Polymers", Applied Polymer Symposia, No. 2, pp. 25-43 (1966).

J. Chiu, "Small Sample Size . . . A New Trend in DTA", Du Pont Thermogram, vol. 1.1, pp. 102 (1964).

O. Toft Sorensen, "Computer Controlled Thermogravimetric Stepwise Isothermal Analysis", Thermochimica Acta, vol. 85, pp. 287-290 (1985).

P. L. Husum and O. T. Sorensen, "Computer Controlled Forced Stepwise Isothermal Analysis", Thermochimica Acta, vol. 114, pp. 131-138 (1987).

S. El-Houte and M. El-Sayed Ali and O. Toft Sorensen, "Dehydration of $CUSOhd 4.5H_2O$ Studied by Conventional and Advanced Thermal Analysis Techniques", Thermochimica Acta, vol. 138, pp. 107-114 (1989).

V. A. Bir and V. A. Logvinenko, "CRTA: A Mathematical Description of Reversible Thermal Dissociation Reactions in the Q-Derivcatograph", J. Therm. Anal., vol. 33, pp. 237-242 (1988).

O. Toft Sorensen, "Quasi-Isothermal Methods in Thermal Analysis", Thermochimica Acta, vol. 50, pp. 163-175 (1981).

A. I. Borovikova and V. A. Logvinenko, "Thermal Aspects of Constant Rate Transformation", J. Therm. Anal.; vol. 33, pp. 97-106 (1988).

I. Groves and L. C. Thomas, "You can determine oil in rubber by vacuum TGA", Vacuum Technology, pp. 133-136 (Feb. 1988).

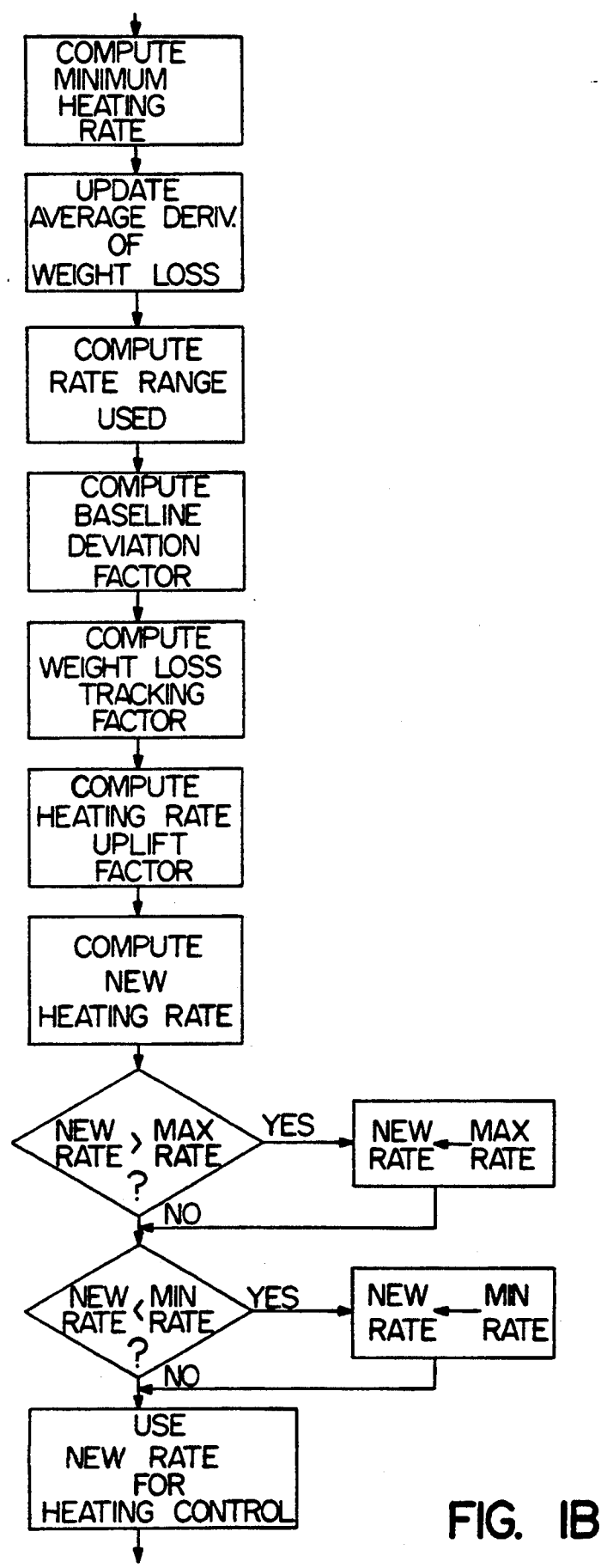
FIG. IB

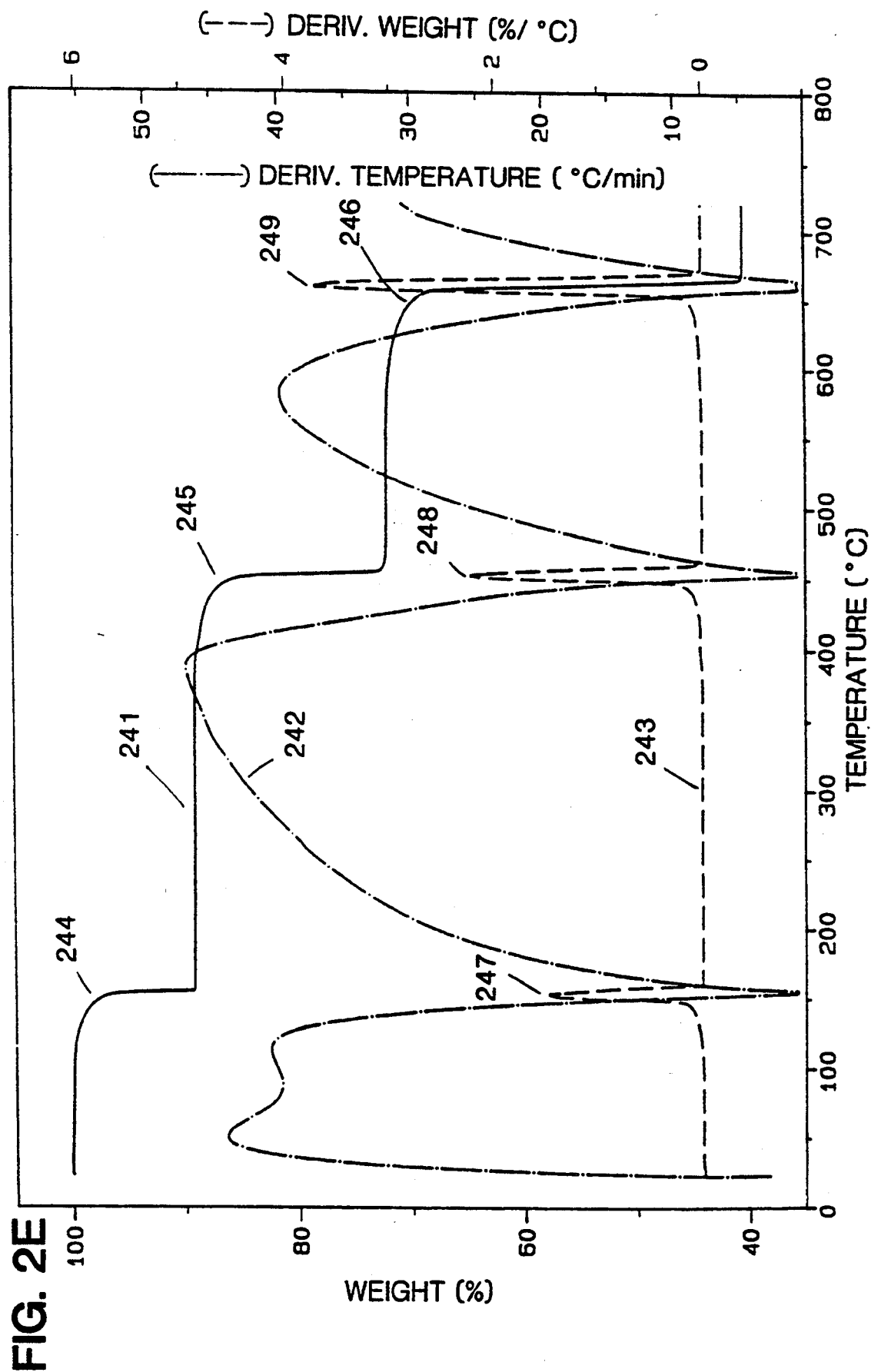

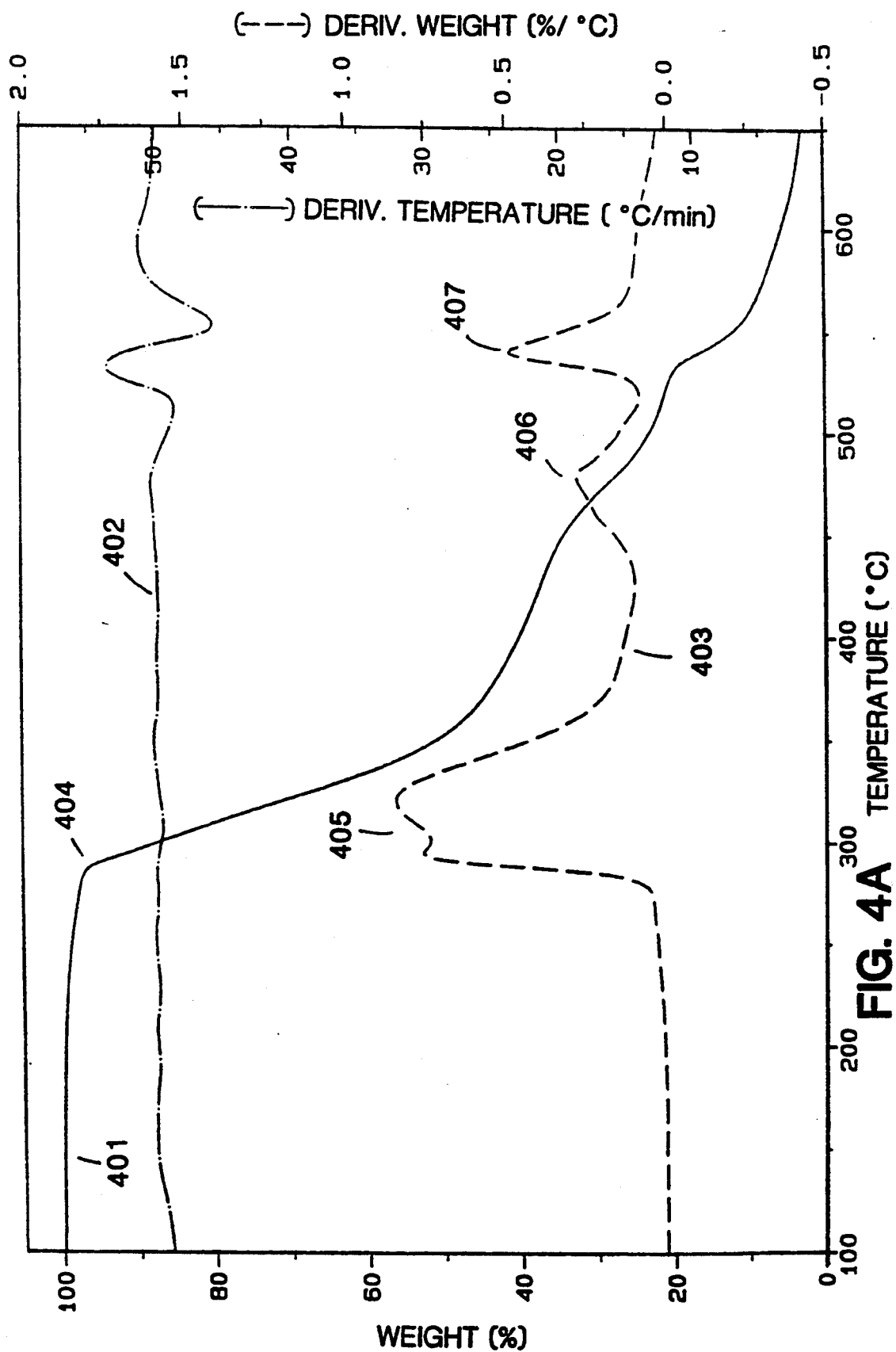

METHOD AND APPARATUS FOR HIGH RESOLUTION ANALYSIS

This application is a divisional application of application Ser. No. 07/663,106, filed on Mar. 1, 1991, now U.S. Pat. No.5,165,792, which is itself a continuation-in-part application of application Ser. No. 07/638,847, filed on Jan. 8, 1991, now abandoned.

BACKGROUND

1. Field of the Invention

The present invention relates to analytical techniques for determining the composition, phase, structure, or other properties of a sample of material.

2. Background of the Invention

Thermal analysis techniques generally comprise measuring a physical parameter as a function of the temperature of the sample. The sample temperature is strictly controlled throughout the analysis. Whenever the sample undergoes a chemical or physical transformation, phase change or other transition which affects the physical parameter being measured, the changes in that physical parameter may be interpreted to analyze the composition, structure, or thermal stability of the sample.

One common thermal analysis technique is thermogravimetric analysis ("TGA"). TGA is a thermal analysis technique which measures the weight change of a material as a function of temperature, or as a function of time at a controlled temperature. The classic TGA method comprises heating the sample at a constant rate of temperature-increase, typically at 10° C. to 50° C. per minute, while the sample weight change or the percent of weight change is recorded versus temperature.

Other thermal analysis techniques include Differential Thermal Analysis (DTA), Differential Scanning Calorimetry (DSC), Pressure Differential Scanning Calorimetry (PDSC), Thermomechanical Analysis (TMA), Dynamic Mechanical Analysis (DMA), Dynamic Mechanical Spectrometry (DMS), Dielectric Analysis (DEA), Differential Photocalorimetry (DPC), Thermal Conductivity Analysis (TCA), and any simultaneous combination of these techniques.

Differential Scanning Calorimetry measures the temperatures and the heat flow associated with transitions in materials as a function of time and temperature. These measurements provide quantitative and qualitative information about the sample transitions that involve endothermic or exothermic processes, or changes in heat capacity. Pressure Differential Scanning Calorimetry is a related technique in which the heat flow and temperature of transitions are measured as a function of temperature under controlled pressure.

Differential Thermal Analysis, like DSC, measures the temperatures and heat flow associated with transitions in materials as a function of time and temperature. However, unlike DSC, DTA results are semi-quantitative. DTA is generally carried out at higher temperatures than DSC.

Thermomechanical Analysis measures linear or volumetric changes in materials as a function of temperature under controlled stress or strain.

Dynamic Mechanical Analysis and Dynamic Mechanical Spectrometry measure mechanical properties of a material as it is deformed under periodic stress as a function of temperature.

Dielectric Analysis measures the dielectric properties of materials as a function of temperature.

Differential Photocalorimetry measures the heat absorbed or released by a sample as it and an inert reference are exposed simultaneously to radiation of known wavelength and intensity.

Thermal Conductivity Analysis measures the thermal conductivity of materials as a function of temperature.

Conventional thermal analysis techniques have limited resolution because in conventional thermal analysis, time and temperature are changing simultaneously. Because chemical and physical transformations are time-dependent (not instantaneous), transitions that actually occur as a function of time are recorded as occurring as a function of temperature.

TGA is particularly useful for observing the thermal decomposition of compounds. When individual thermal decompositions occur at well separated temperatures, quantitative information about sample composition may be obtained from the percent weight change per minute at each transition. However, due to the limited resolution of conventional TGA, in conventional TGA decomposition transitions frequently overlap or appear drawn out in temperature. This substantially reduces the ability to obtain an accurate measurement of weight change and reaction temperature.

It has long been known that the use of very slow TGA heating rates will improve the separation of some overlapping transitions and, thus, increases the resolution of the technique. U.S. Pat. No. 3,344,654 to Erdey, et al. ("Erdey"), which is incorporated by reference herein, discloses a quasi-static technique of reducing heating rate to limit the rate of weight change to a predetermined maximum during transitions. Although using very slow heating rates or heating rates controlled by sample weight change improves the separation of transitions, such methods also increase substantially the total time required for a measurement, thereby reducing laboratory productivity.

Moreover, increasing measurement time reduces the accuracy and reliability of the analysis. For example, a sample exposed to high temperatures for a long period of time undergoes slow time-dependent changes such as oxidation, deformation, absorption and adsorption, which may introduce errors in the analysis. The long time period also implies further difficulties due to instrument drift, and to ambient temperature, humidity, and pressure variations. Mechanical vibrations and fluctuations in the voltage of the main power line also increasingly affect the accuracy of the analysis as the analysis time increases. Furthermore, the effective signal-to-noise ratio is reduced, because the signal peaks are flattened by the slow temperature ramp.

Quasi-static techniques are discussed extensively in the article by F. Paulik and J. Paulik, "Thermoanalytical Examination Under Quasi-Isothermal—Quasi-Isobaric Conditions." *Thermochimica Acta*, Vol. 100 (1986), pp. 23–59, which is incorporated by reference herein. The Paulik quasi-isothermal technique attempts to maintain a specific rate of weight change by controlling the temperature of the sample.

DEFINITIONS

"Downstream analytical technique", as used herein, means any analytical technique that is commonly used in conjunction with gas chromatography to determine quantitatively or qualitatively the presence or concentration of atomic, molecular, or ionic species in the effluent of a gas chromatograph, such as mass spectroscopy, Fourier transform infrared spectroscopy, laser diode spectrometry, flame ionization detection, electron capture detection, photoionization detection, flame photometric detection and chemiluminescent detection.

"Driving variable", as used herein, means the independent physical parameter, such as temperature, pressure, time, applied stress, or wavelength of incident radiation, that is being used to drive a material through a transition. For example, in thermal analysis techniques such as TGA, temperature is the driving variable.

"Characterizing physical parameter", as used herein, means the dependent physical parameter characterizing the sample, such as its weight, length, volume, dielectric or mechanical properties, or thermal conductivity. For example, in TGA the characterizing physical parameter is the percent weight change of the sample. In thermomechanical analysis, the characterizing physical parameters are the linear or volumetric changes in the material.

"Resolution" of an analytical technique, as used herein, means the degree to which signals associated with different transitions can be physically separated in the analytical data produced by the technique. This quality of the analytical technique is most critical when multiple transitions occur at closely spaced values of the driving variable.

"Signal baseline", as used herein, means that portion of a signal representing the value of a characterizing physical parameter obtained in a range in which there are no transitions or transformations.

"Transition" or "transformation", as used herein, mean any type of physical or chemical transformation, phase change, or structural change in a material.

SUMMARY OF THE INVENTION

The present invention uses a computer system to control an analytical technique by monitoring and controlling the technique's driving variable according to changes observed in a characterizing physical parameter, according to preselected maximum and minimum values for the rate of change of the driving variable, and/or according to preselected values for the rate of change of the characterizing parameter.

For example, when the analytical technique is TGA, the driving variable is temperature, and the characterizing physical parameter is the weight of the sample. The derivative of the change in sample weight (weight percent per minute) is calculated in real time. Periodically, e.g., every half second, the computer accepts as inputs the rate of weight change, the sample heating rate (i.e., the rate of increase in sample temperature), the maximum heating rate and the resolution setting. The computer then uses these inputs to calculate a new sample heating rate according to the method of the present invention. The analytical system then controls the heating of the sample material according to the new sample heating rate.

There are four techniques used in a first preferred embodiment of the present invention. Each improves the resolution of thermal analysis methods and/or reduces the total time required for analysis. Individually or in combination, they provide an analytical method applicable to all thermal analysis techniques that dramatically improves their resolution, reduces the time required for analysis, and enhances their ability to detect small transformations. These improvements are realized because these techniques sharpen the signal derived from each transition and increase the separation of closely spaced transitions.

The first technique comprises monitoring the signal baseline, detecting deviations from the signal baseline, and then rapidly decreasing the sample heating rate as the sample undergoes a chemical or physical transformation. This allows the use of very high heating rates through temperature regions with no transitions (for example, greater than 50 degrees Celsius per minute) while preventing overshoot of the transition temperature.

The second technique comprises constraining the furnace heating rate to a minimum rate during a transition or transformation to prevent isothermal or cooling operation, thereby driving the sample through the transition or transformation.

The third technique comprises using a "heating uplift" step to force the apparatus back to the maximum heating rate when the derivative of weight change falls below a certain rate.

The fourth technique comprises adjusting the heating rate as a function of the rate of sample weight change to track a desired constant rate of weight change.

The present invention may be practiced using all four of the techniques in the first preferred embodiment described above. However, any one, two, or three of the four techniques may be used to obtain improved results.

When two or more of the techniques are applied simultaneously, the heating rates derived from each technique are combined to control the heating rate of the sample.

The second preferred embodiment of the present invention comprises two modes of operation. The first mode continually controls the heating rate according to a function comprising an exponential term, wherein the argument of the exponential term includes the percent weight change per minute of the sample. The function is chosen such that, when the percent weight change per minute is very small, i.e., during baseline operation, the heating rate approaches its maximum allowed value. When the percent weight change per minute is very large, i.e., during a transition, the heating rate approaches zero.

The second mode of operation in the second preferred embodiment of the present invention is also based upon controlling the heating rate according to a function computing an exponential term, wherein the argument of the exponential term includes the percent weight change per minute of the sample. The function is chosen such that, when the percent weight change per minute is very small, i.e., during baseline operation, the heating rate is controlled close to a maximum rate as in the first mode. When the percent weight change per minute is large, i.e., during a transition, the heating rate is held at a minimum value. Typically, the minimum value of the heating rate is 0.01° C./minute. For the majority of materials, the preferred value for the minimum value of the heating rate ranges from 0 to about 10% of the maximum value of the heating rate. Once the heating rate falls to the minimum value, it is held at that value until the percent weight change per minute of the sample falls below a selected value for the percent weight change per minute. The selected value for the percent weight change per minute required to override the "hold" at the minimum heating rate may be, for example, one order of magnitude lower than the value of the percent weight change per minute required to force the heating rate to the minimum heating rate.

An alternative to the above described method for overriding the "hold" at the minimum heating rate is to override holding when the heating rate falls to a constant value, i.e., establishes a baseline region. This is particularly useful when the baseline rate of weight change is substantially different after a transition is complete from what it was prior to the onset of the transition.

The operator selects the mode of operation, and also selects the resolution of the analysis. In both modes of operation, the argument of the exponential term includes a factor based on the resolution setting, as well as the factor based upon the percent weight change per minute of the sample. In both modes of operation, the heating rate is generally either close to the maximum rate or to the minimum rate, depending upon the percent weight loss per minute, except for a transition region at intermediate values of the percent weight loss per minute, in which small changes in the percent weight loss per minute result in rapid changes in the heating rate. The relative position of the transition region, i.e., how much percent weight loss per minute is required to increase the heating rate significantly above the minimum, or decrease it significantly below the maximum, is adjusted by the choice of the resolution setting.

Both modes of operation could be used in a single analysis. For example, if the operator needs the highest possible resolution in a particular temperature region, e.g., to resolve two closely-spaced transitions, but does not need the high resolution in other temperature regions, the operator could use one mode for the part of the analysis that does not require the highest possible resolution, and the other mode for the part of the analysis that does.

A first object of the present invention is to provide a temperature control method for thermal analysis techniques which achieves substantially improved resolution of transitions, without increasing the time required for analysis, or possibly reducing the time required for analysis, compared to the times required for analysis by conventional constant heating rate methods.

A second object of the present invention is to provide the analyst with a method for selecting the desired instrument resolution.

A third object of the present invention is to provide a method for improving the accuracy of thermal analysis techniques by preventing thermal overshoot of transition temperatures during heating.

A fourth object of the present invention is to improve the sensitivity of thermal analysis techniques.

A fifth object of the present invention is to simplify the interpretation of thermal analysis data by more sharply defining the temperatures at which transitions occur, for example as demonstrated by the narrowness of the peaks of derivative signals corresponding to transitions.

A sixth object of the present invention is to obtain transition temperatures which more accurately reflect the isothermal reaction temperatures of the transitions.

A seventh object of the present invention is to isolate signal changes so that they can be more easily measured, integrated, compared with other results, and interpreted.

These and other objects of the present invention are described in greater detail in the detailed description of the invention, the appended drawings and the attached claims.

DESCRIPTION OF THE DRAWINGS

FIG. 1b is a flow chart showing some of the computing steps used in a first preferred embodiment of the invention.

FIGS. 2a-2f are TGA scans of calcium oxalate obtained according to the methods described in Example 2.

FIGS. 4a-4c are TGA scans of black electrical tape obtained according to the methods described in Example 4.

DETAILED DESCRIPTION OF THE INVENTION

The present invention resides in control methods for conventional analytical apparatus, and is an improvement on the methods conventionally used to control such conventional apparatus.

The following detailed description of the present invention applies specifically to thermogravimetric analysis, in which temperature is the driving variable and weight change is the characterizing physical parameter. However, although the present invention is described as it is applied to thermogravimetric analysis, it should be understood that the present invention could be used with any thermal analytical method including Differential Thermal Analysis, Differential Scanning Calorimetry, Thermomechanical Analysis, Pressure Differential Scanning Calorimetry, Dynamic Mechanical Analysis, Dynamic Mechanical Spectrometry, Dielectric Analysis, Differential Photocalorimetry, and Thermal Conductivity Analysis, as well as any combination of these techniques. The principles and methods described herein with reference to thermogravimetric analysis could be applied to any and all of the thermal analytical methods listed above, as well as to other analytical methods wherein a characterizing physical parameter is measured as a function of a driving variable.

Figure 1A:
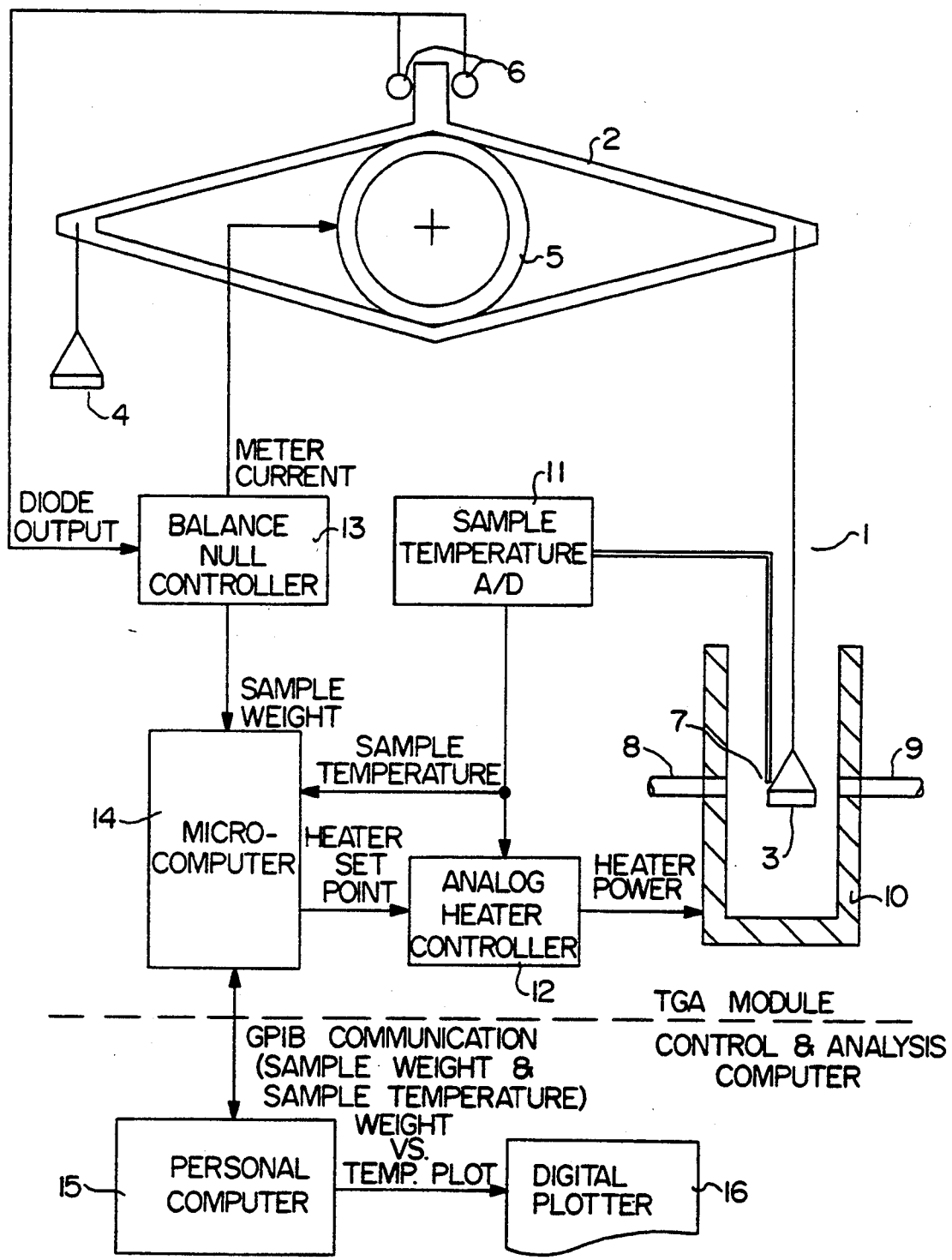
FIG. 1a is a block diagram of a thermogravimetric apparatus.

FIG. 1a is a schematic representation of a conventional thermogravimetric analyzer, showing thermogravimetric balance 1, comprising a balance beam 2, a sample pan 3 and a tare pan 4, a balance null meter movement 5, photo diodes for detecting the balance null 6, sample temperature thermocouple 7, purge gas inlet 8 and purge gas outlet 9, electric furnace 10, sample temperature digitizer 11, heater controller 12, balance null controller 13, and microcomputer 14. FIG. 1a also shows personal computer 15 and digital plotter 16. The thermogravimetric balance measures the weight of a sample in sample pan 3 by measuring the current required by balance null meter movement 5 to maintain the apparatus in balance, as indicated by photodiode detectors 6. The balance null controller 13 receives the signal from the photo diode detectors 6, and increases or decreases the meter current accordingly. Balance null controller 13 provides microcomputer 14 with the weight of the sample, which is calculated from the meter current. Microcomputer 14 also receives the sample temperature from sample temperature thermocouple 7 via sample temperature digitizer 11, and controls the temperature of the sample by controlling the power to furnace 10 using heater controller 12. In the first preferred embodiment of the present invention, the temperature of the sample is controlled by the microcomputer in accordance with the steps outlined below. However, the present invention can be practiced using any combination of computers, hardware and operator control. Personal computer 15 and digital plotter 16 are used to analyze, store, display and plot the analytical results. A purge gas is usually introduced via the purge gas inlet. The purge gas can be a gas that reacts with constituents of the sample being analyzed, or an inert gas, i.e., a gas that does not react with the sample used to prevent reactions with air. Typical purge gases include dry air, oxygen, nitrogen, argon, helium, carbon monoxide and carbon dioxide.

The purge gas may also be used to remove products of the reaction for additional analysis further down the gas stream, via a downstream analytical technique. Analytical techniques and detectors currently being used with gas chromatography may be used with a TGA apparatus operated according to the present invention, including mass spectrometry, atomic spectroscopy, molecular spectroscopy, dispersive infrared spectrometry, laser diode spectroscopy, flame ionization detectors (FID), thermal conductivity detectors (TCD), electron capture detectors (ECD), photoionization detectors (PID), helium ionization detectors (HID), discharge ionization detectors (DID), flame photometric detectors (FPD), chemiluminescent detectors (CD), Raman spectroscopy, and Fourier transform infrared spectrometry (FT-IR). Signals derived from the downstream analytical technique could be used to control the sample temperature, in addition to, or instead of, the thermal analysis signal.

The first preferred embodiment of the present invention is outlined in FIG. 1b, using thermogravimetric analysis as an example. FIG. 1b is a flow chart showing the computing steps used to calculate the heating rate of the sample according to the first preferred embodiment of the present invention, as it is applied to thermogravimetric analysis. The flow chart shown in FIG. 1b includes the four techniques described above in the description of the first preferred embodiment for controlling the heating rate of the sample. These techniques are described in detail below.

Figure 1C:
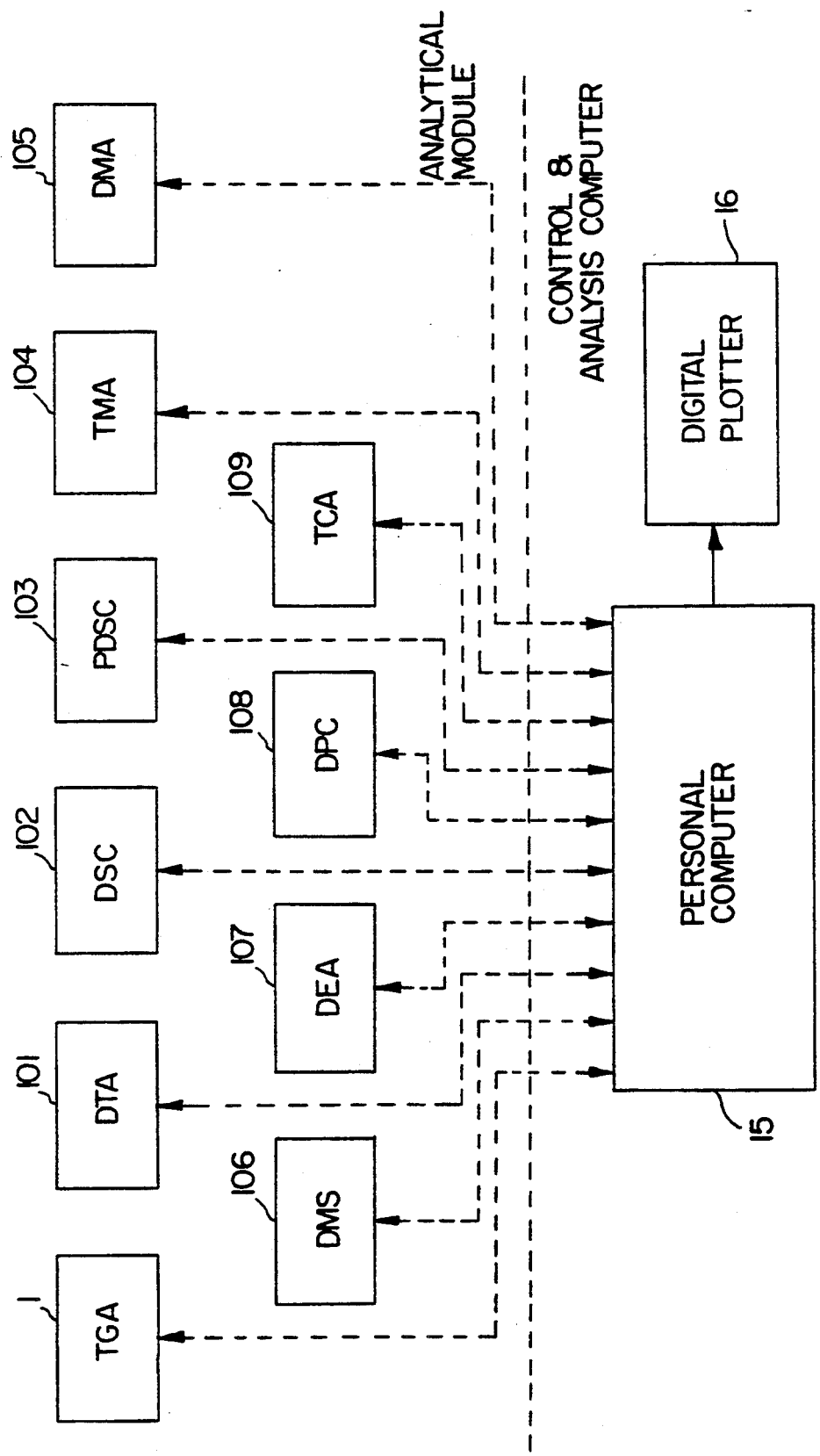
FIG. 1c is a schematic diagram showing how the present invention may be used with Thermogravimetric Analysis (TGA), Differential Thermal Analysis (DTA), Differential Scanning Calorimetry (DSC), Pressure Differential Scanning Calorimetry (PDSC), Thermomechanical Analysis (TMA), Dynamic Mechanical Analysis (DMA), Dynamic Mechanical Spectrometry (DMS), Dielectric Analysis (DEA), Differential Photocalorimetry (DPC), and Thermal Conductivity Analysis (TCA).

FIG. 1c is a schematic diagram showing modules representing many analytical techniques, including Thermogravimetric Analysis (TGA) 1, Differential Thermal Analysis (DTA) 101, Differential Scanning Calorimetry (DSC) 102, Pressure Differential Scanning Calorimetry (PDSC) 103, Thermomechanical Analysis (TMA) 104, Dynamic Mechanical Analysis (DMA) 105, Dynamic Mechanical Spectrometry (DMS) 106, Dielectric Analyzer (DEA) 107, Differential Photocalorimetry (DPC) 108 and Thermal Conductivity Analysis (TCA) 109. Any one of these techniques may be used in conjunction with a personal computer 15 to practice the present invention.

Figure 1D:
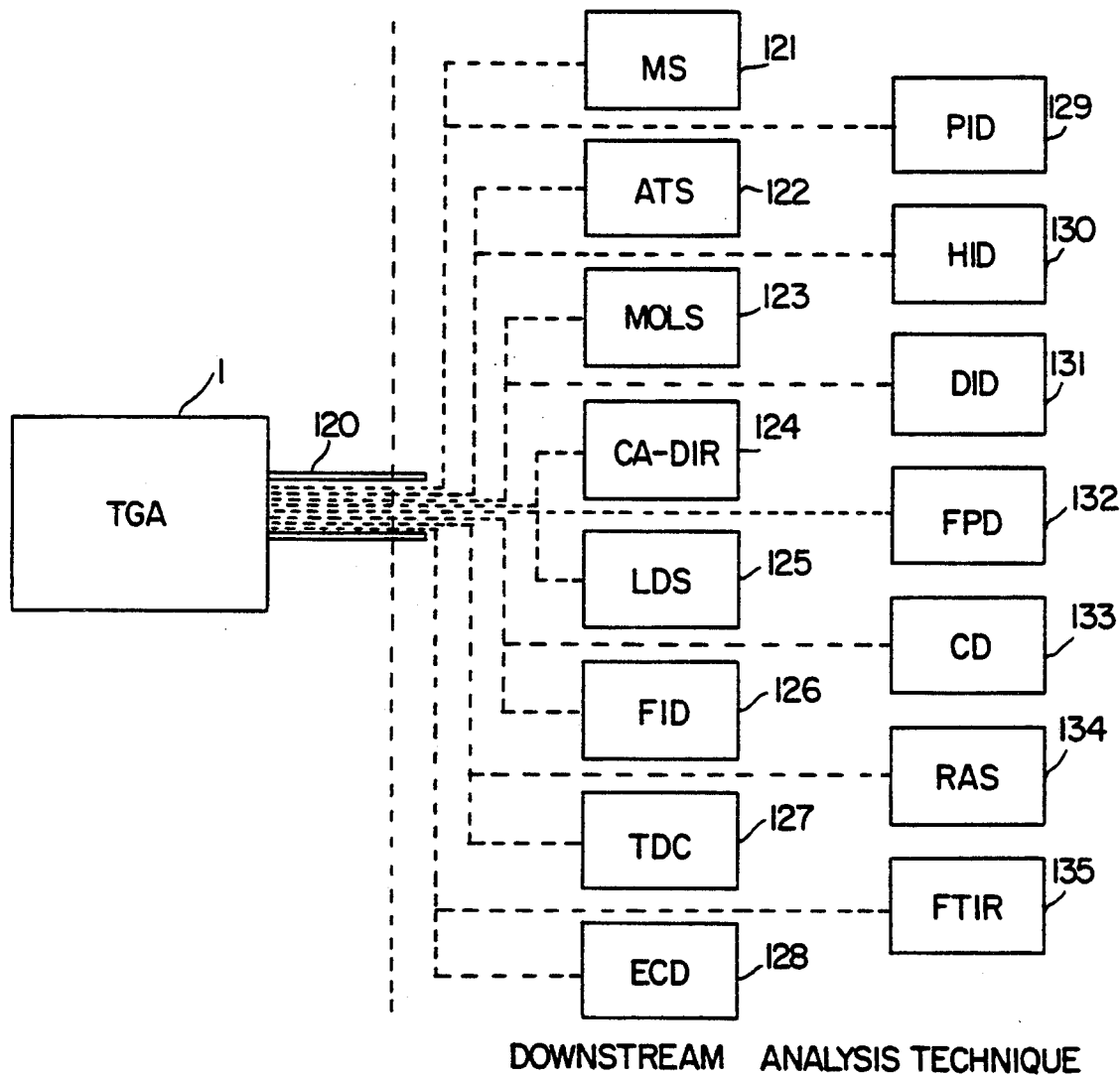
FIG. 1d is a schematic diagram showing how downstream analytical techniques such as mass spectroscopy, Fourier transform infrared spectroscopy, computer-aided dispersive spectroscopy, laser diode spectroscopy, flame ionization spectroscopy, Raman spectroscopy, thermal conductivity detectors, electron capture detectors, photoionization detectors, flame photometric detectors, and chemiluminescent detectors may be used with the present invention.

FIG. 1d is a schematic showing the use of downstream analytical techniques with thermogravimetric analysis. FIG. 1d shows a purge gas 120 carrying products of the reaction for further analysis downstream by mass spectrometry (MS) 121, atomic spectrometry (ATS) 122, molecular spectroscopy (MOLS) 123, computer-aided dispersive infrared spectroscopy (CA-DIR) 124, laser diode spectroscopy (LDS) 125, flame ionization detector (FID) 126, thermal conductivity detector (TCD) 127, electron capture detector (ECD) 128, photoionization detectors (PID) 129, helium ionization detector (HID) 130, discharge ionization detectors (DID) 131, flame photometric detectors (FPD) 132, chemiluminescent detector (CD) 133, Raman spectroscopy (RAS) 134 and Fourier transform infrared spectrometer (FT-IR) 135.

The first method described in detail herein with reference to thermogravimetric analysis incorporates all four of the techniques used in the first preferred embodiment of the present invention. However, any of the four techniques could be used alone, or in combination with one or more of the other techniques, to improve the resolution of a thermal analysis method and/or to reduce the time required for analysis.

The first such technique, the BASELINE technique, comprises monitoring the signal baseline, detecting deviations from the signal baseline, and then rapidly decreasing the sample heating rate as the sample undergoes a chemical or physical transformation. This allows the use of very high heating rates during regions of no transition (for example, greater than 50 degrees Celsius per minute) while preventing overshoot of the transition temperature.

The second such technique, the DRIVING technique, comprises constraining the sample heating rate to a minimum rate during a transition to prevent isothermal or cooling operation, thereby driving the sample through the transition. The minimum heating rate may be a predetermined heating rate, or it may be a dynamically determined heating rate. It could be dynamically determined based upon such factors as, for example, the rate of weight change, time spent at the minimum heating rate, the second derivative of the weight change, or other characteristics of the specific experiment.

The third such technique, the UPLIFT technique, comprises using a "heating uplift" step to force the apparatus back to the maximum heating rate when the derivative of weight change falls below a certain rate.

The fourth such technique, the TRACKING technique, comprises adjusting the heating rate as a function of the rate of sample weight change to track a desired constant rate of weight change.

When two or more of the techniques are applied simultaneously, the heating rates derived from each technique are combined to control the heating rate of the sample.

The first preferred embodiment of the present invention comprises the following steps, wherein step 11 corresponds to the BASELINE technique, step 12 corresponds to the TRACKING technique, step 13 corresponds to the UPLIFT technique, and step 16 corresponds to the DRIVING technique:

STEP 1. Selecting a maximum heating rate ("rate__max").

STEP 2. Selecting a resolution setting ("res__setting"). For example, resolution settings of 1, 2, 3, 4, or 5 could set minimum heating rates of 20%, 7.4%, 2.7%, 1.0% and 0.37% of the maximum heating rate, respectively. Thus, the fastest scans would be obtained using the lowest resolution setting of 1, while scans obtained using the highest resolution setting of 5 would require increased time for analysis.

STEP 3. Computing a minimum allowed heating rate ("rate__min") from the maximum heating rate and the resolution setting. This rate is constrained to be a fraction of the maximum rate such that increasingly higher resolution settings produce proportionally lower minimum heating rates. For example, at the lowest resolution setting the minimum heating rate could be 20% of the maximum rate and at the highest resolution setting the minimum heating rate could be 0.37% of the maximum rate.

STEP 4. Continuously monitoring the weight change of the sample ("wgt__pct"), e.g., by measuring the weight change every half second.

STEP 5. Computing the current derivative with respect to time of the weight change of the sample ("pct__drv").

STEP 6. Computing an average derivative with respect to time of the weight change of the sample ("pct__drv__avg"). For example, the average derivative could be computed with an exponential filter in which 98% of the previous average derivative is added to 2% of the current derivative every half second. The exponential filter simulates an infinite response analog filter by taking 98% of the previous average and adding 2% of the current value (i.e., pct__drv__avg=0.98*pct__drv__avg+0.02*pct__drv).

STEP 7. Computing the fraction of the allowed heating rate range currently being used from the selected maximum heating rate and the computed minimum heating rate. The fraction of the allowed heating rate ("range__used") is defined as the difference between the current heating rate ("rate__now") and the minimum heating rate ("rate__min") divided by the difference between the maximum heating rate ("rate__max") and the minimum heating rate ("rate__min"). This value is used to control the influence of the baseline deviation factor and weight loss tracking factor in the heating rate adjustment calculation (see step 14, below).

STEP 8. (BASELINE TECHNIQUE) Computing the baseline deviation heating rate adjustment factor ("rate__baseline__err"). This factor is equal to the baseline conversion constant (e.g., 1.0° C./%) multiplied by the product of the allowed heating rate range ("range__used") and the absolute value of the difference between the average derivative ("pct__drv__avg") and the current weight change derivative ("pct__drv") (i.e., rate__baseline__err=1.0*range__used*ABS (pct__drv__avg−pct__drv). This factor will naturally increase at the onset of transitions when heating rates are near the maximum but it is reduced at low heating rates. This factor operates to reduce the heating rate rapidly at the onset of a transition to prevent overshooting of the transition temperature.

STEP 9. (TRACKING TECHNIQUE) Computing the weight change tracking heating rate adjustment factor ("rate__tracking__err"). This factor is equal to the tracking conversion constant (0.1° C./%) multiplied by the product of one minus the allowable heating rate range used ("range__used") and the difference between the desired constant weight change derivative ("pct__drv__target") and the absolute weight change derivative ("ABS(pct__drv)") (i.e., rate__tracking__err=0.1*(ABS (pct__drv)−pct__drv__target)*(1.0−range__used)). For example, the desired derivative could be constrained to the range of 2.5%, 2.0%, 1.5%, 1.0% and 0.5% per minute corresponding to resolution settings 1, 2, 3, 4, and 5, respectively. This factor functions by tending to adjust the heating rate to maintain a constant rate of weight change during a transition in which the current heating rate is relatively low.

STEP 10. (UPLIFT TECHNIQUE) Computing the uplift adjustment factor to the heating rate ("rate__uplift__err"). This factor is equal to the uplift conversion constant (0.025° C./%) multiplied by the common logarithm of the absolute average weight change derivative ("ABS (pct__drv__avg)") (i.e., rate__uplift__err=0.025*LOG (ABS(pct__drv__avg)). However, this factor is set to zero when the average weight change derivative is greater than 1.0% per minute and to a reasonable maximum (e.g., −0.1) when the average weight change derivative is less than 0.0001% per minute. The principal purpose of this factor is to accelerate the rise in heating rate when the current weight change derivative is very small, thereby insuring near maximum heating rates during baseline periods and consequently minimizing the measurement time.

STEP 11. Computing an adjustment to the heating rate ("rate__now") from the baseline deviation factor ("rate__baseline__err"), the weight change tracking factor ("rate__tracking__err") and the uplift heating rate factor ("rate__uplift__err"). The new heating rate ("rate__new") is defined to be the current heating rate ("rate__now"), minus the sum of the baseline deviation factor, the weight change tracking factor and the heating rate uplift factor (i.e., rate__new= rate__now−(rate__baseline__err+rate__tracking__err+rate__uplift__err)).

STEP 12. Comparing the new heating rate ("rate__new") to the maximum allowed rate ("rate__max"). The new rate is set to the maximum allowed rate if the new rate is greater than the maximum allowed rate. This prevents thermal runaway of the furnace during baseline operation.

STEP 13. (DRIVING TECHNIQUE) Comparing the new heating rate ("rate__new") to the minimum allowed rate ("rate__min"). The new rate is set to the minimum allowed rate if the new rate is less than the minimum allowed rate. This reduces analysis time and prevents reversal of the sample temperature ramp. The sample temperature thus increases throughout the thermal analysis at a rate between the minimum and maximum heating rates allowed (inclusive).

STEP 14. The current heating rate is set to the new heating rate.

FIGS. 2–6 are plots of TGA analyses practiced according to the first preferred embodiment of the present invention. These figures are discussed in detail in Examples 2–6, below.

In the first preferred embodiment of the present invention, for example, the maximum heating rate used for thermogravimetric analysis could range from 1 degree/minute to 100 degrees/minute Celsius, the resolution setting could range from 1 (lowest resolution) to 5 (highest resolution), and the temperature of the sample could range from room temperature to 1000 degrees Celsius.

Figure 7:
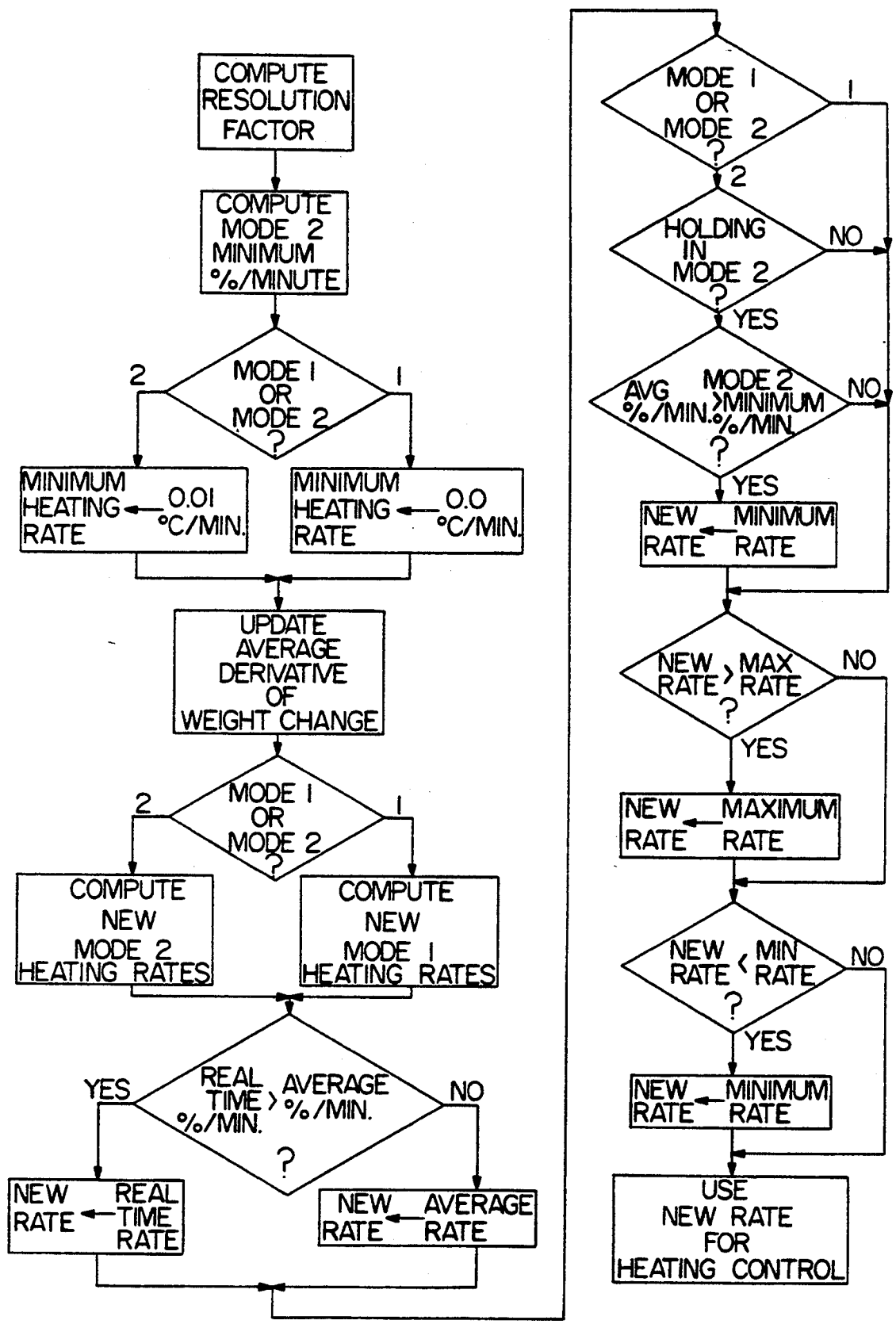
FIG. 7 is a flow chart showing some of the computing steps used in a second preferred embodiment of the invention.

The second preferred embodiment of the present invention is outlined in FIG. 7, as it is applied to thermogravimetric analysis. The second preferred embodiment comprises two modes of operation. The first mode is chosen to maximize the productivity of the analytical instrument. The second mode is chosen to obtain the highest possible resolution and greatest analytical accuracy. In both modes of operation, the heating rate is controlled by an exponential term. The argument of the exponential term includes the percent weight change per minute of the sample and a factor based upon a resolution setting chosen by the operator. The heating rate for both modes of operation is close to the maximum heating rate during baseline operation, i.e., in temperature regions in which no transitions occur. In the first mode of operation, the heating rate approaches zero during a transition. In the second mode of operation, the heating rate is held at 0.01° C./minute during transitions. Once the heating rate falls to 0.01° C./minute, it is held at 0.01° C./minute until the percent weight change per minute falls below a preselected value. The preselected value could be, for example, 10% of the weight percent change per minute required to drive the heating rate to 0.01° C./minute. As an alternative, the heating rate is held at 0.01° C./minute until the rate of weight change reaches a constant value.

The second preferred embodiment comprises the following steps (1–14):

STEP 1. Selecting a maximum heating rate ("rate__max").

STEP 2. Selecting a resolution setting ("res__setting"). The resolution setting ranges from −8.0 to +8.0. Positive values of the resolution setting are used to select the first mode of operation ("mode 1"). Negative values of the resolution setting are used to select the second mode of operation ("mode 2"). Most analyses are run with a resolution setting of −5.0 to −3.0 for the second mode of operation, and +3.0 to +5.0 for the first mode of operation.

STEP 3. Monitoring the percent weight change of the sample ("wgt__pct").

STEP 4. Calculating the derivative of the percent weight change with respect to time ("pct__drv").

STEP 5. Computing the resolution factor from the absolute value of the resolution setting ("res__factor").

STEP 6. Computing the minimum mode 2 percent weight change ("mode2__pct__min") from the resolution factor.

STEP 7. Computing the minimum heating rate allowed. If in mode 2, then the minimum is set to 0.01° C./minute. Otherwise, the minimum rate is set to zero.

STEP 8. Computing a delayed average derivative with respect to time of the weight change of the sample. The delay ("drv__delay__ctr") allows any ringing or overshoot in the weight percent per minute to dampen out. The average weight percent per minute ("pct__drv__avg") is computed by adding 1% of the current value of the weight percent derivative ("pct__drv") to 99% of the previously computed average weight percent derivative.

STEP 9. Computing two new heating rates for the first mode of operation, and two new heating rates for the second mode of operation. For each mode of operation, one new heating rate is calculated using the real-time percent weight change per minute ("rate__drv__pct"), and another new heating rate is calculated using the average weight percent weight change per minute ("rate__drv__avg"). The equation used to calculate the new heating rate for the first mode of operation divides the maximum heating rate by an exponential term. The argument of the exponential term includes either the real-time or the average percent weight change per minute, as discussed above, and the resolution factor. The equation used to calculate the new heating rate for the second mode of operation multiplies the maximum heating rate by a factor comprising a constant minus an exponential term. As in the first mode of operation, the argument of the exponential term includes either the real-time or the average percent weight change per minute, and the resolution factor.

STEP 10. Choosing the new heating rate ("rate__new") calculated from the largest weight change per minute.

STEP 11. In mode 2, checking the current heating rate ("rate__now"). If the current heating rate is equal to or below the minimum heating rate and the average weight change per minute is greater than the minimum weight change per minute for mode 2 operation, then the new heating rate is held at the minimum heating rate. If the average weight change per minute is less than the minimum weight change per minute for mode 2 operation, the computed new heating rate is used to control the sample heating rate.

STEP 12. Limiting the new heating rate to the maximum heating rate allowed. If the new heating rate is greater than the maximum heating rate allowed, the new heating rate is set at the maximum heating rate.

STEP 13. Limiting the new heating rate to the minimum heating rate allowed. If the new heating rate is less than the minimum heating rate, the new heating rate is set at the minimum heating rate.

STEP 14. Setting the current heating rate ("rate__now") equal to the new heating rate.

The steps listed above for the second preferred embodiment use the first alternative for overriding a "hold" at the minimum temperature. The second alternative, overriding the "hold" when the rate of weight change reaches a constant value, can be implemented by, for example, detecting when the rate of weight loss per minute does not change for a preselected period of time.

The present invention can be practiced at higher temperatures, by using materials resistant to higher temperatures, and high temperature equipment. For example, a temperature of 1600 degrees Celsius can be achieved using a high temperature furnace. Different temperature ranges could be used for particular applications, depending on the characteristics of the apparatus used.

The present invention can also be applied to chemical or physical transformations that occur upon cooling as well as upon heating, or upon any combination of heating and cooling cycles, whether or not separated by constant temperature periods or constant-rate heating or cooling periods. When the technique is used to analyze materials that undergo transitions upon cooling, the methods described above are still applied, but with the sample cooling rate substituted for the sample heating rate, and with a cooling apparatus substituted for or used in conjunction with the furnace.

The sample could be heated or cooled using hot or cold air, lasers, fluid baths, microwave energy, chemical reactions, or other appropriate experimental techniques.

For certain reactions, e.g., for explosive reactions, the sample could be self-heated by the chemical reactions, in which the reaction rate is controlled by controlling another variable, such as a fluid flow rate, a pressure or partial pressure of a reacting gas, or by exposure to electromagnetic radiation or to a magnetic field.

The preferred embodiments of the present invention, as described above, control the heating rate of the sample. However, the present invention could be practiced by controlling the sample temperature itself instead of by controlling the heating rate.

FURTHER EMBODIMENTS OF THE INVENTION

The present invention may be employed in other analytical techniques in which temperature is not the driving variable to achieve a similar improvement in the resolution, sensitivity, accuracy and efficiency of those techniques. For example, the present invention could be applied to chemical transformations that occur as a function of applied or ambient pressure, or as a function of the intensity or wavelength of electromagnetic radiation directed at the sample. The present invention may be applied whenever a chemical or physical transformation produces a change in a measurable physical characteristic of a sample as a function of a driving variable.

The present invention may be implemented using hardware, software, or a combination of hardware and software. For example, the maximum heating rate may be limited by adjusting the physical characteristics of the furnace, or by programming a computer that controls the furnace heating rate. Analog devices such as amplifiers could be used for multiplication, integrators for summation, inverters for subtraction, and comparators for decision-making.

The following examples are provided to illustrate certain embodiments of the present invention. They are not to be construed as limiting the invention in any way.

EXAMPLE 1: THERMOGRAVIMETRIC ANALYSIS

This example describes the experimental apparatus and procedures used in Examples 2-6 and Examples 8-9. The TGA system used for these analyses was the TA Instruments TGA 2950 Thermogravimetric Analyzer connected to the TA Instruments Thermal Analyst 2100 computer/thermal analyzer. The instruction manuals for this apparatus are hereby incorporated by reference. All samples used in the experiments were readily available commercial products. Sample sizes varied from 5 to 22 milligrams of material. The samples were loaded into standard 50 microliter platinum sample pans. The purge gases used were either compressed air or nitrogen (99.998% pure), as noted in the Figures for the specific examples. The TGA was set up and leveled on a solid non-vibrating work surface.

Before operation of the TGA apparatus, a steady flow of purge gas was established. The purge gas was connected through pressure regulators and flow meters to the balance and furnace purge inlet ports on the instrument. The flow meters were adjusted to a flow rate of 40 ml/minute to the balance and 60 ml/minute to the furnace for a combined total of 100 ml/min. purge flow rate over the sample pan. When nitrogen was used, the purge gas flow was allowed to purge the system for one hour before starting the experiment.

The sample thermocouple was adjusted to a distance of 5 millimeters above the sample in the analyses described Examples 4, 5, 6, 8 and 9. The distance was 1 millimeter in Examples 2 and 3. The longer distance (5 mm) produced a more stable heating control because the thermocouple is not overly influenced by sudden changes in sample temperature due to endothermic or exothermic reactions of the sample material.

The sample pan was cleaned by first heating the sample pan in a bunsen burner flame until the pan was glowing orange due to its temperature to burn off any residual materials leaving only ash. Any ash remaining was dumped from the pan and the pan was brushed out if necessary. The sample pan was then placed on the loading platform and the TGA was commanded to perform an automatic tare operation by pressing the Tare button. This procedure entailed loading and weighing the empty sample pan and storing the empty weight of the sample pan as a negative offset to the measured experimental weight.

Samples were prepared by cutting off or pouring out small portions of the material of the approximate weight needed and placing them in the center of the sample pan on the platform. In Example 4, the adhesive side of the sample tape was placed facing upwards. Powdered samples were distributed uniformly inside the sample pan.

Sample identification, the desired maximum heating rate, the final temperature to be reached, and the resolution setting were programmed into the computer/thermal analyzer.

The TGA experimental sequence was started by pressing the "Start" button on the TGA 2950. The computer/thermal analyzer then automatically performed the following steps: (1) the sample platform, with the loaded sample pan riding on the platform, was moved to the balance load position and the balance arm was lowered electronically to engage a hook on the balance hang-down wire with the bale of the sample pan; (2) once engaged, the sample pan was lifted from the platform by the balance arm and the platform was moved aside; the sample pan and sample were held motionless by the nulling current in the balance meter movement; (3) the furnace was raised via a motor and drive screw mechanism to surround the sample and the sample thermocouple and seal the furnace chambers against the bottom of the balance housing with an O-ring; (4) the sample pan and sample were weighed for approximately 30 seconds to allow the system to stabilize and establish the initial (100%) sample weight; (5) the sample was heated according to the present invention, as described specifically in Examples 2-6 and Examples 8–9; (6) sample temperature and sample weight were continuously monitored at a rate of 10 times/second; temperature and weight information were averaged, filtered and stored on hard disk in the computer at a rate of one data point every two seconds; (7) when the specified final temperature was reached, the computer turned off power to the furnace and stopped data storage; (8) the furnace cooled back to ambient temperature aided by a heat exchanger and a water cooling jacket around the outside of the furnace; and (9) the sample was unloaded automatically by reversing steps 1 through 3.

The data collected on the computer hard disk was then analyzed and plotted on the digital x-y plotter. Derivative curves were generated mathematically from the temperature, time and weight change data stored on disk.

EXAMPLE 2: EFFECT OF RESOLUTION SETTINGS ON TEMPERATURE ACCURACY, TRANSITION SEPARATION AND ANALYTICAL TIME FOR CALCIUM OXALATE

Figure 2A:
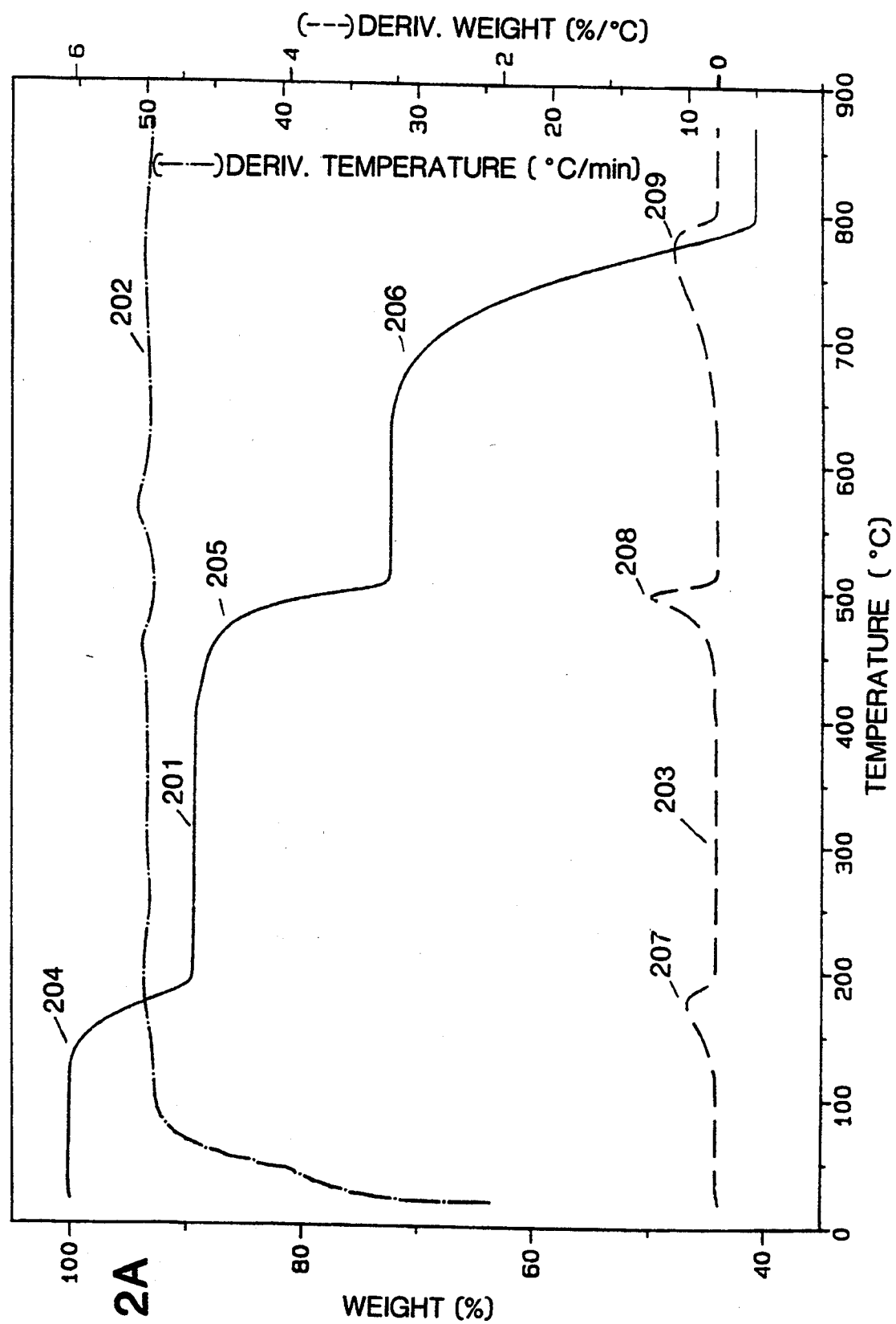
Figure 2B:
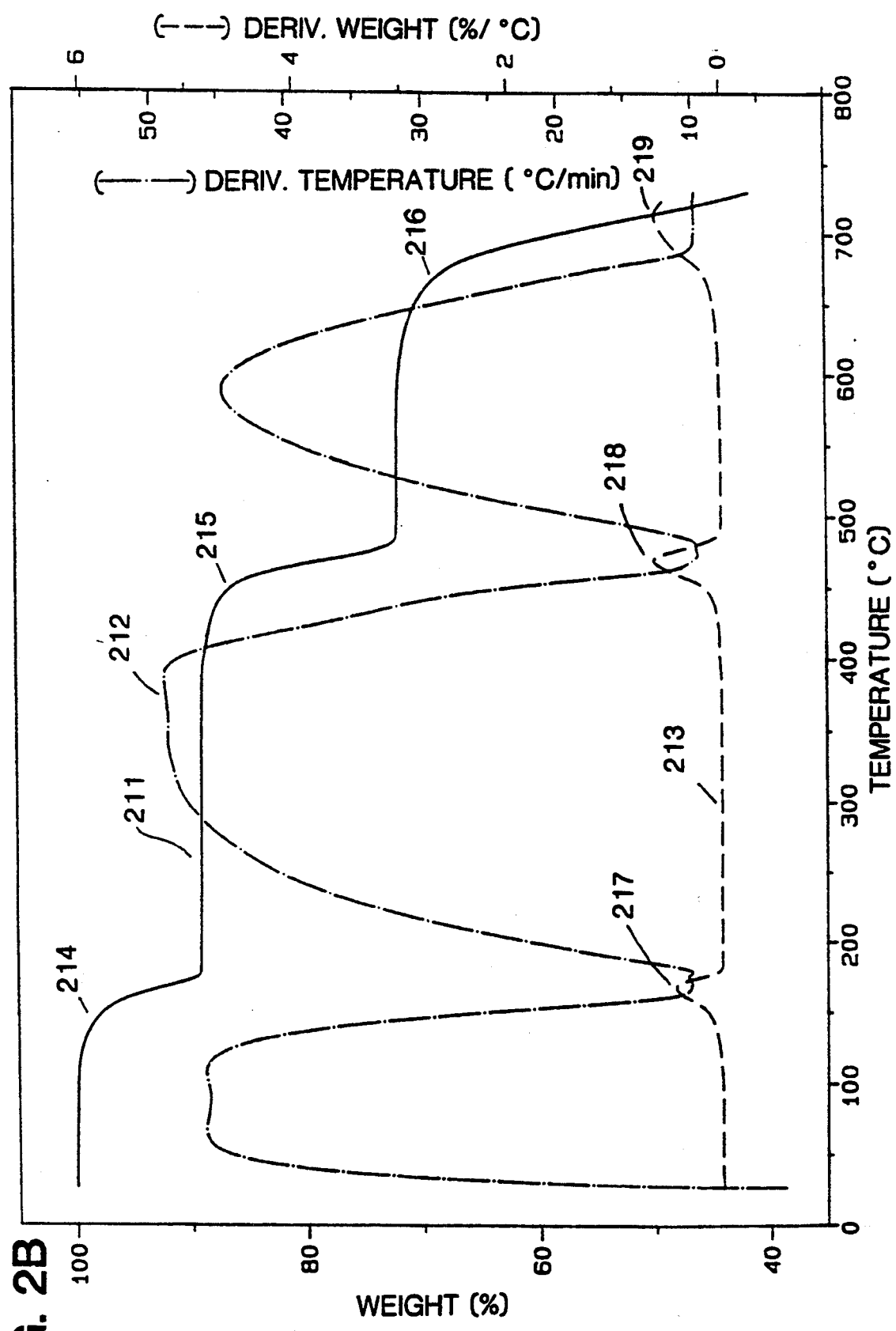
Figure 2C:
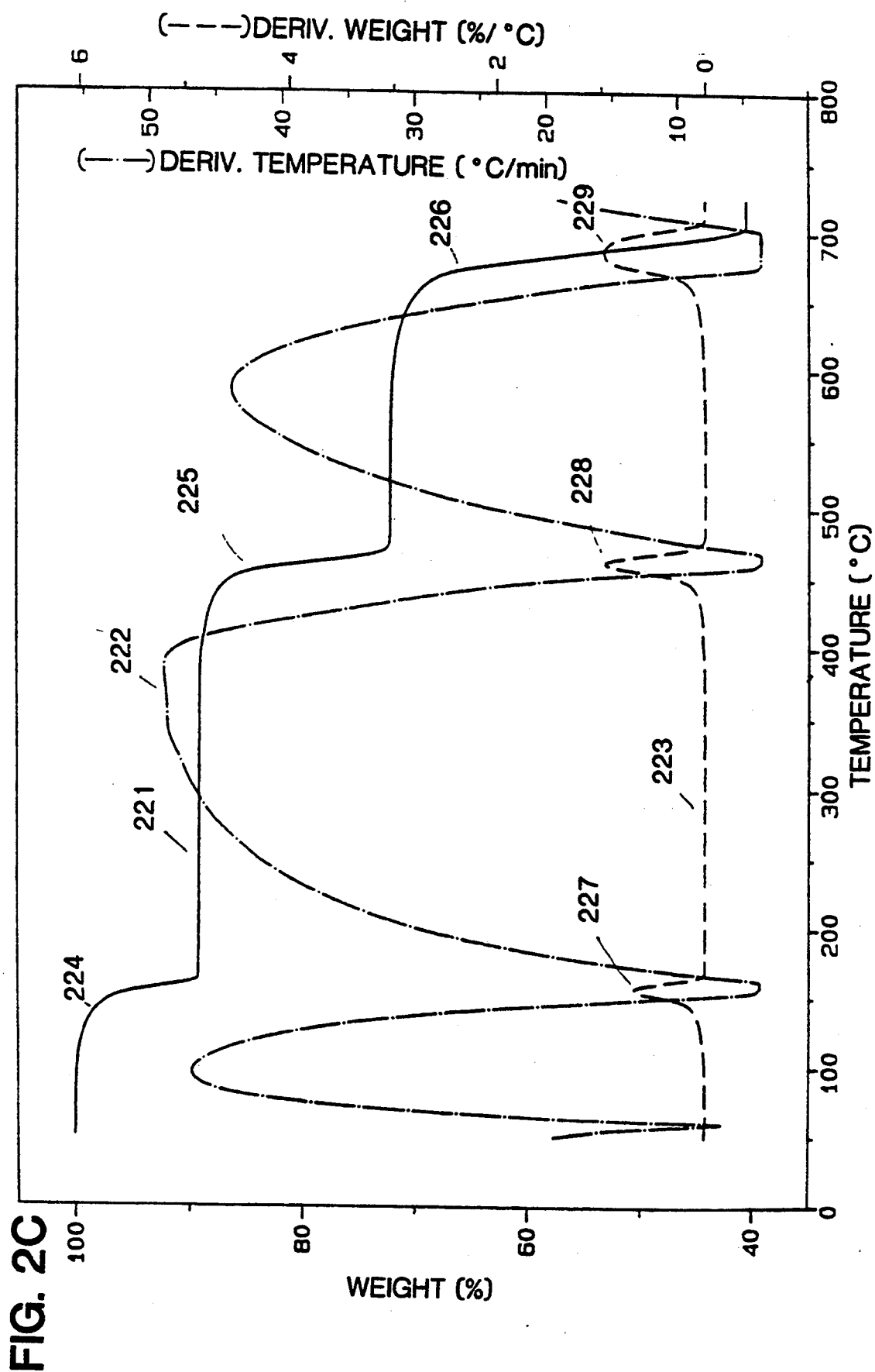
Figure 2D:
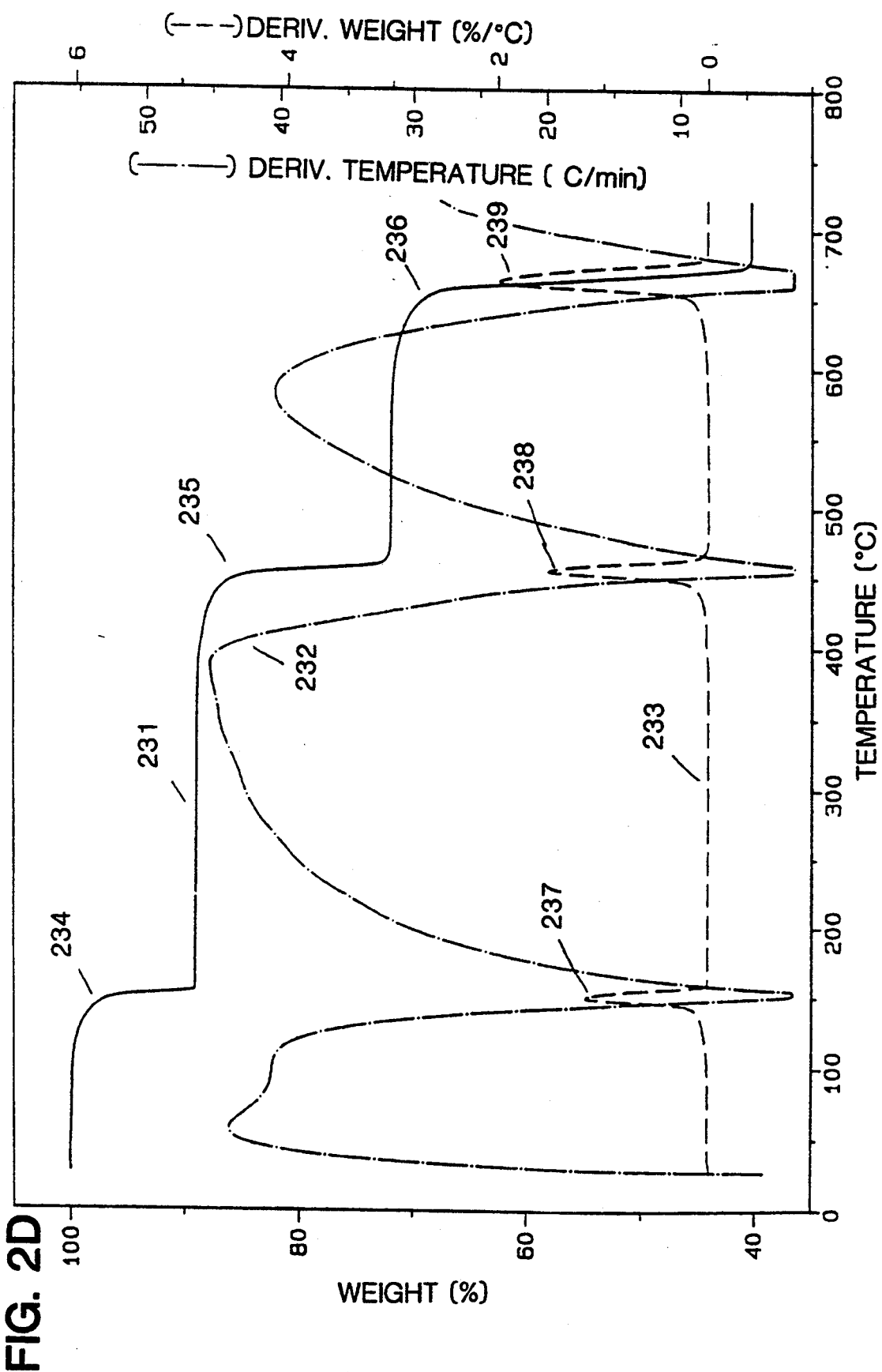
Figure 2F:
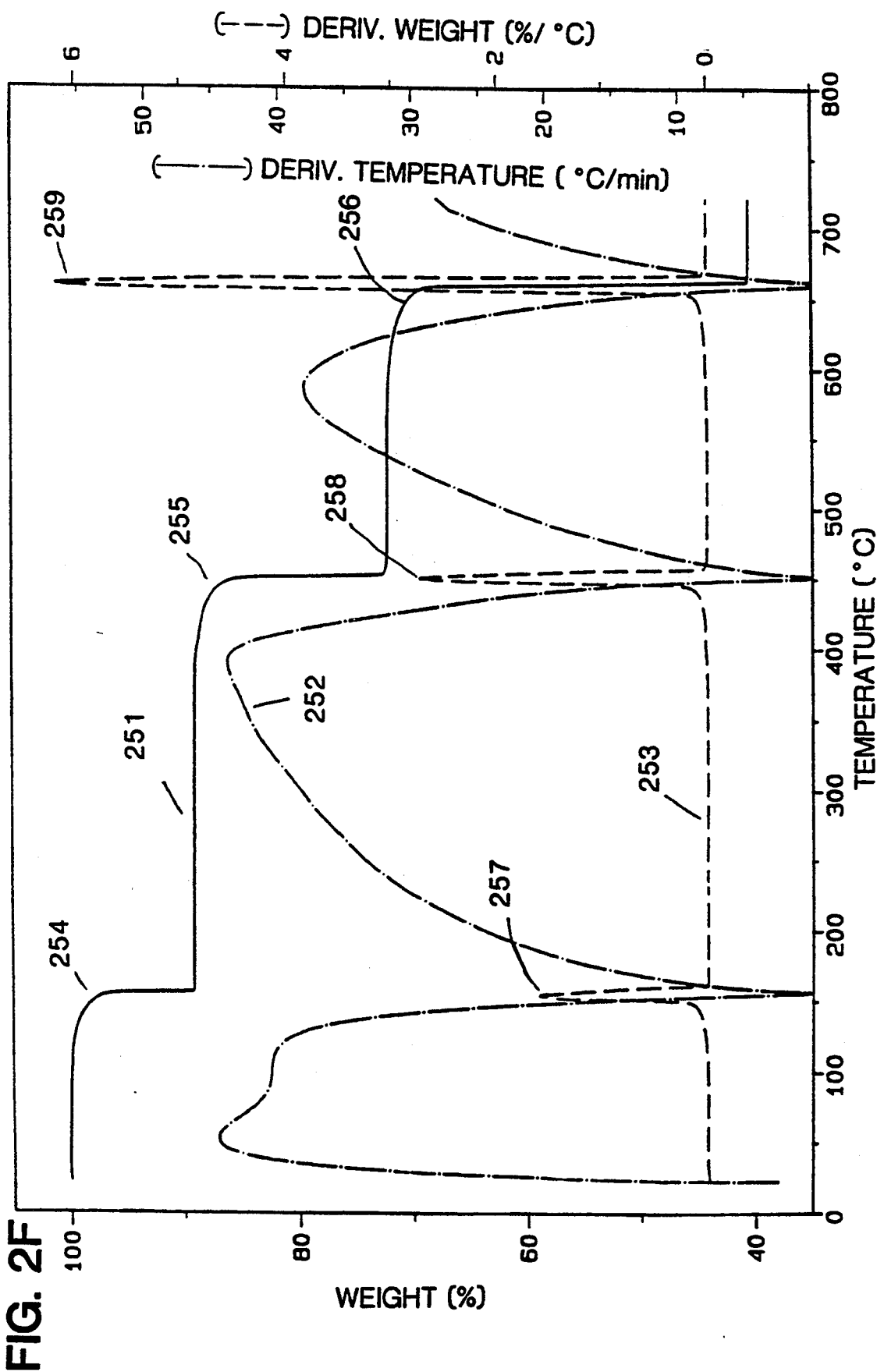

Samples of calcium oxalate monohydrate, $CaC_2O_4$:$H_2O$ were examined in air by conventional TGA using the first preferred embodiment of the present invention to compare the results obtained using different resolution settings. The experimental procedures followed in this example for preparing the apparatus, loading the samples, and running analyses were described in Example 1. The results of the analyses are shown in FIGS. 2a–2f. FIG. 2a is a TGA scan obtained according to the conventional method, at a constant heating rate of 50° C./minute from ambient temperature to above 800° C. FIGS. 2b, 2c, 2d, 2e and 2f are TGA scans obtained according to the first preferred embodiment (steps 1–14) of the present invention at resolution settings of 1, 2, 3, 4 and 5, respectively.

Each of the scans shows three curves. Curves 201 (FIG. 2a), 211 (FIG. 2b), 221 (FIG. 2c), 231 (FIG. 2d), 241 (FIG. 2e) and 251 (FIG. 2f) are plots of the percent weight change of the sample as a function of sample temperature. Curves 202 (FIG. 2a), 212 (FIG. 2b), 222 (FIG. 2c), 232 (FIG. 2d), 242 (FIG. 2e) and 252 (FIG. 2f) are plots of the derivative with respect to time of the sample temperature versus sample temperature. Curves 203 (FIG. 2a), 213 (FIG. 2b), 223 (FIG. 2c), 233 (FIG. 2d), 243 (FIG. 2e) and 253 (FIG. 2f) are plots of the derivative with respect to temperature of the percent weight change of the sample as a function of sample temperature.

Calcium oxalate is a well understood material which produces three well-separated and easily observed weight loss transitions between 100° C. and 800° C. In the first transition, water is released. The first transition appears as features 204 and 207 in FIG. 2a; 214 and 217 in FIG. 2b; 224 and 227 in FIG. 2c; 234 and 237 in FIG. 2d; 244 and 247 in FIG. 2e; and 254 and 257 in FIG. 2f. In the second transition, calcium carbonate is formed with the release of carbon monoxide gas. The second transition appears as appears as features 205 and 208 in FIG. 2a; 215 and 218 in FIG. 2b; 225 and 228 in FIG. 2c; 235 and 238 in FIG. 2d; 245 and 248 in FIG. 2e; and 255 and 258 in FIG. 2f. In the third transition, calcium oxide is formed with the release of carbon dioxide gas. The third transition appears as features 206 and 209 in FIG. 2a; 216 and 219 in FIG. 2b; 226 and 229 in FIG. 2c; 236 and 239 in FIG. 2d; 246 and 249 in FIG. 2e; and 256 and 259 in FIG. 2f.

As shown in FIGS. 2b–2f, increasing the resolution setting from 1 (lowest resolution) to 5 (highest resolution) results in progressively sharper weight loss transitions and higher, narrower derivative peaks. The approach to isothermal transition temperature can be observed at all resolution settings, but is most pronounced at the higher resolution settings. Contrasting the TGA scan at resolution setting 5 (FIG. 2f) with the constant heating rate TGA scan (FIG. 2a) shows the dramatic improvement in reaction temperature determination afforded by the present invention.

The total time required for the experiments of FIGS. 2b–2f were 28, 37, 46, 53, and 63 minutes for resolution settings of 1–5 respectively. This demonstrates the trade-off between minimizing the total time required for analysis and obtaining higher resolutions.

EXAMPLE 3: IMPROVED TRANSITION SEPARATION AND REDUCED ANALYTICAL TIME AT DIFFERENT MAXIMUM HEATING RATES FOR CALCIUM OXALATE

Figure 3A:
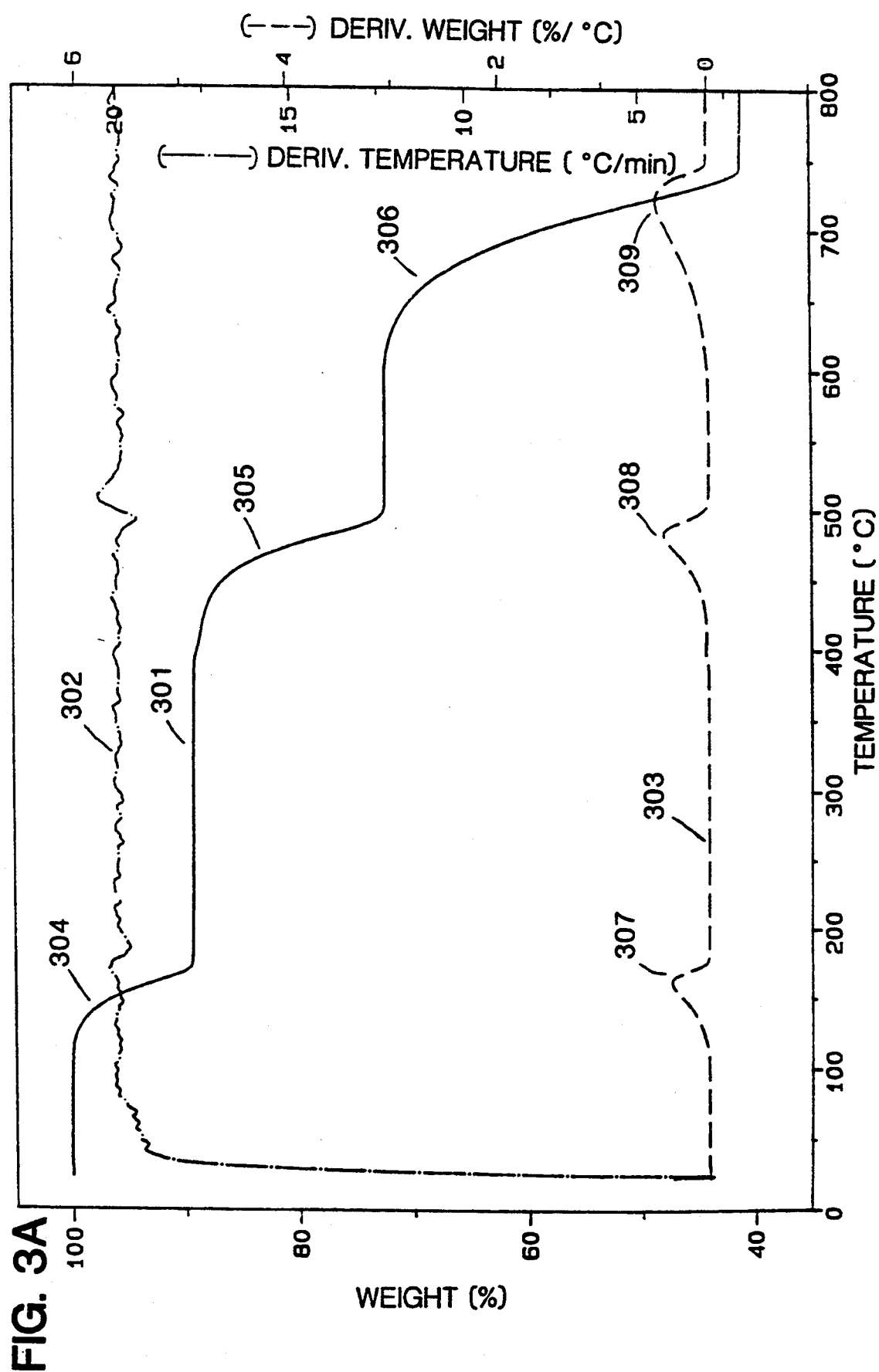
FIGS. 3a-3e are TGA scans of calcium oxalate obtained according to the methods described in Example 3.
Figure 3B:
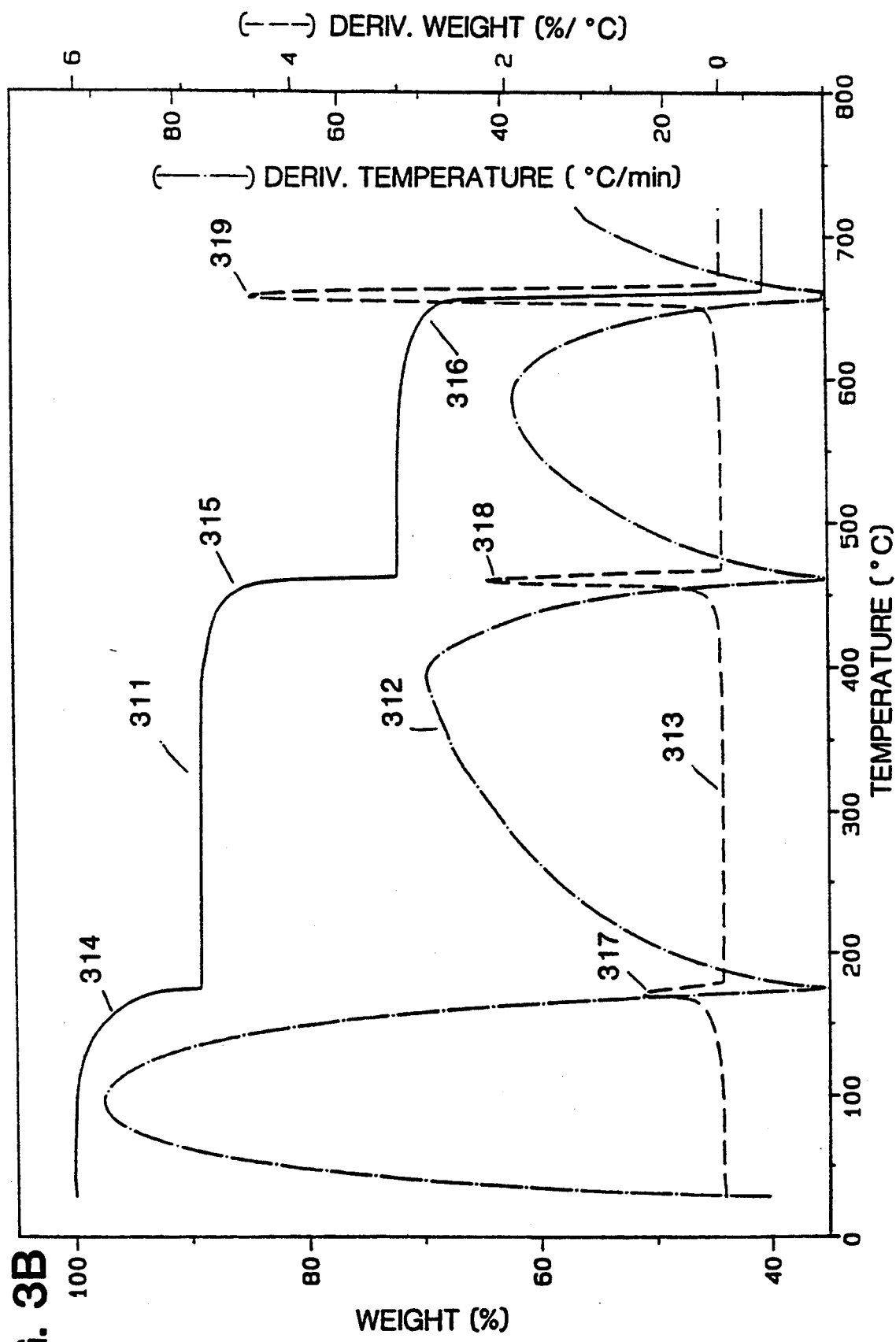
Figure 3C:
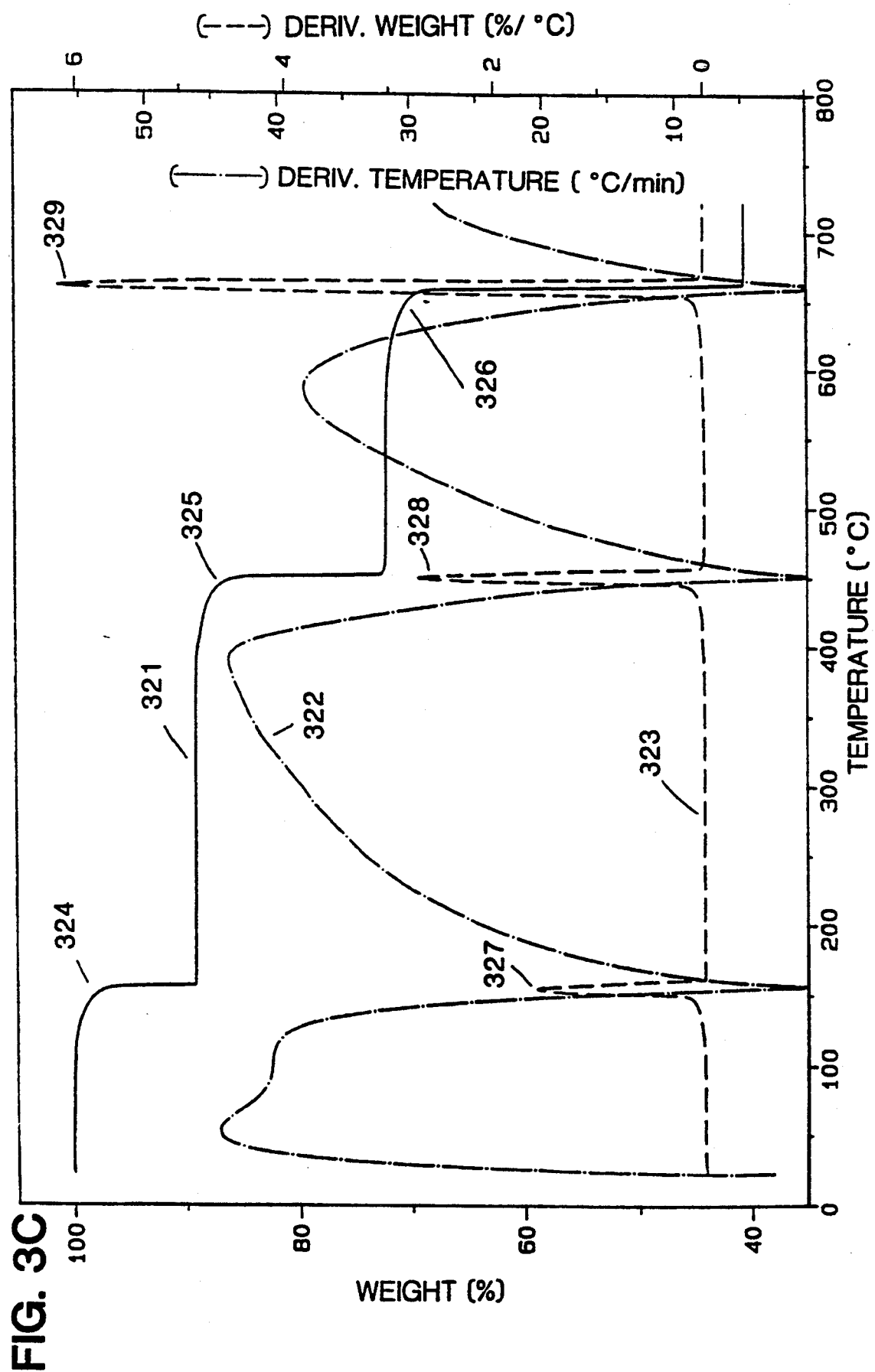

Samples of calcium oxalate monohydrate, $CaC_2O_4$:$H_2O$ were examined in air by conventional TGA using the first preferred embodiment of the present invention to compare the results obtained at a given resolution setting at different maximum heating rates. The experimental procedures followed in this example for preparing the apparatus, loading the samples, and running analyses were described in Example 1. The results of the analyses are shown in FIGS. 3a–3e. FIG. 3a is a TGA scan obtained according to the conventional method, at a constant heating rate of 20° C./minute from ambient temperature to above 800° C. FIGS. 3b, 3c, 3d and 3e are TGA scans obtained according to the first preferred embodiment (steps 1–14) of the present invention described above, with a resolution setting of 5, and maximum heating rates of 100° C./minute, 50° C./minute, 20° C./minute, and 10° C./minute, respectively.

Each of the scans shows three curves. Curves 301 (FIG. 3a), 311 (FIG. 3b), 321 (FIG. 3c), 331 (FIG. 3d) and 341 (FIG. 3e) are plots of the percent weight change of the sample as a function of sample temperature. Curves 302 (FIG. 3a), 312 (FIG. 3b), 322 (FIG. 3c), 332 (FIG. 3d) and 342 (FIG. 3e) are plots of the derivative with respect to time of the sample temperature as a function of sample temperature. Curves 303 (FIG. 3a), 313 (FIG. 3b), 323 (FIG. 3c), 333 (FIG. 3d) and 343 (FIG. 3e) are plots of the derivative with respect to temperature of the percent weight change of the sample as a function of sample temperature.

Calcium oxalate is a well understood material which produces three well-separated and easily observed weight loss transitions between 100° C. and 800° C., as explained in Example 2. The first transition (water is released) appears as features 304 and 307 in FIG. 3a; 314 and 317 in FIG. 3b; 324 and 327 in FIG. 3c; 334 and 337 in FIG. 3d; and 344 and 347 in FIG. 3e. The second transition (calcium carbonate is formed and carbon monoxide is released) appears as features 305 and 308 in FIG. 3a; 315 and 318 in FIG. 3b; 325 and 328 in FIG. 3c; 335 and 338 in FIG. 3d; and 345 and 348 in FIG. 3e. The third transition (calcium oxide is formed and carbon dioxide is released) appears as features 306 and 309 in FIG. 3a; 316 and 319 in FIG. 3b; 326 and 329 in FIG. 3c; 336 and 339 in FIG. 3d; and 346 and 349 in FIG. 3e.

Figure 3D:
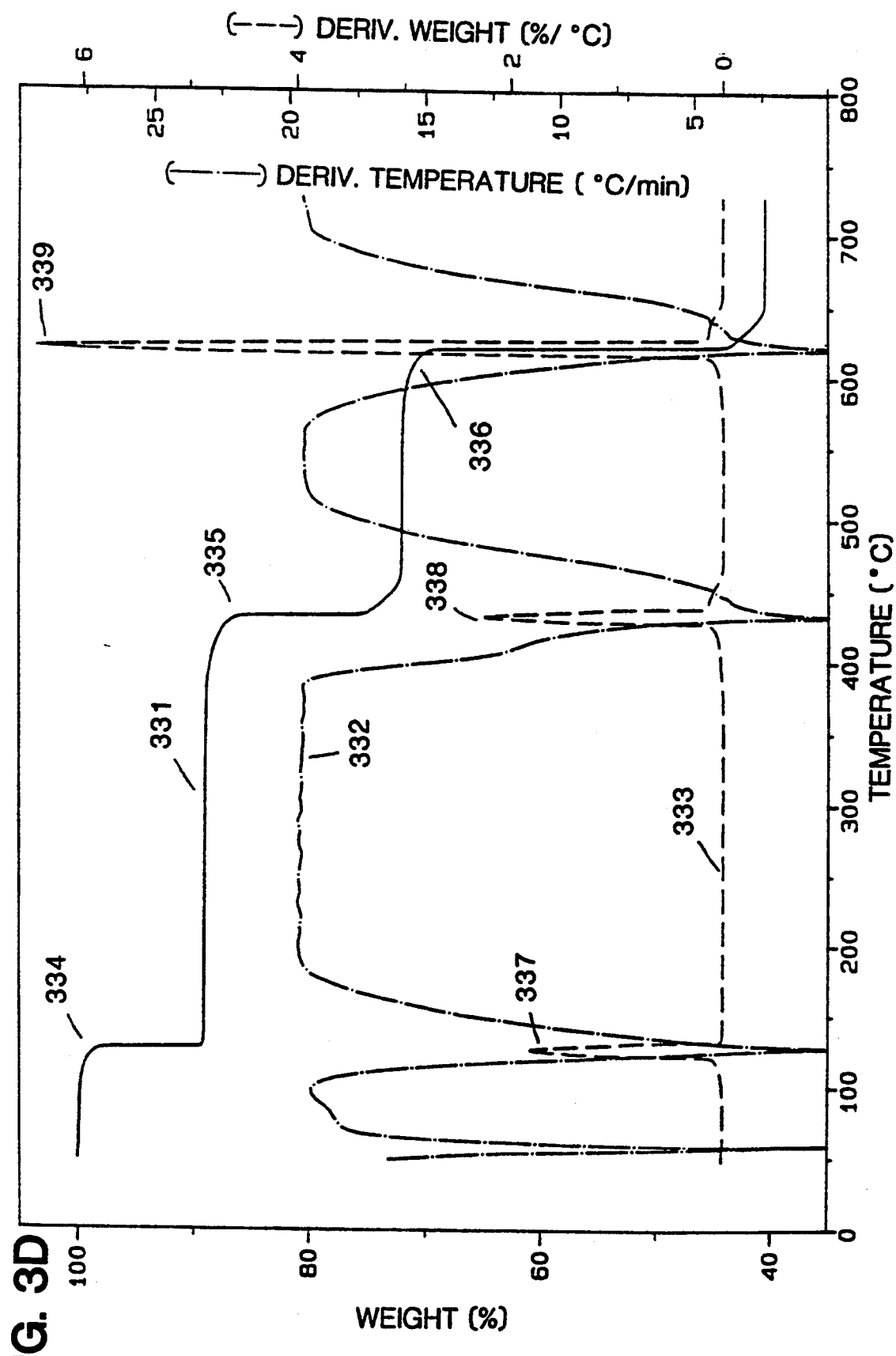
Figure 3E:
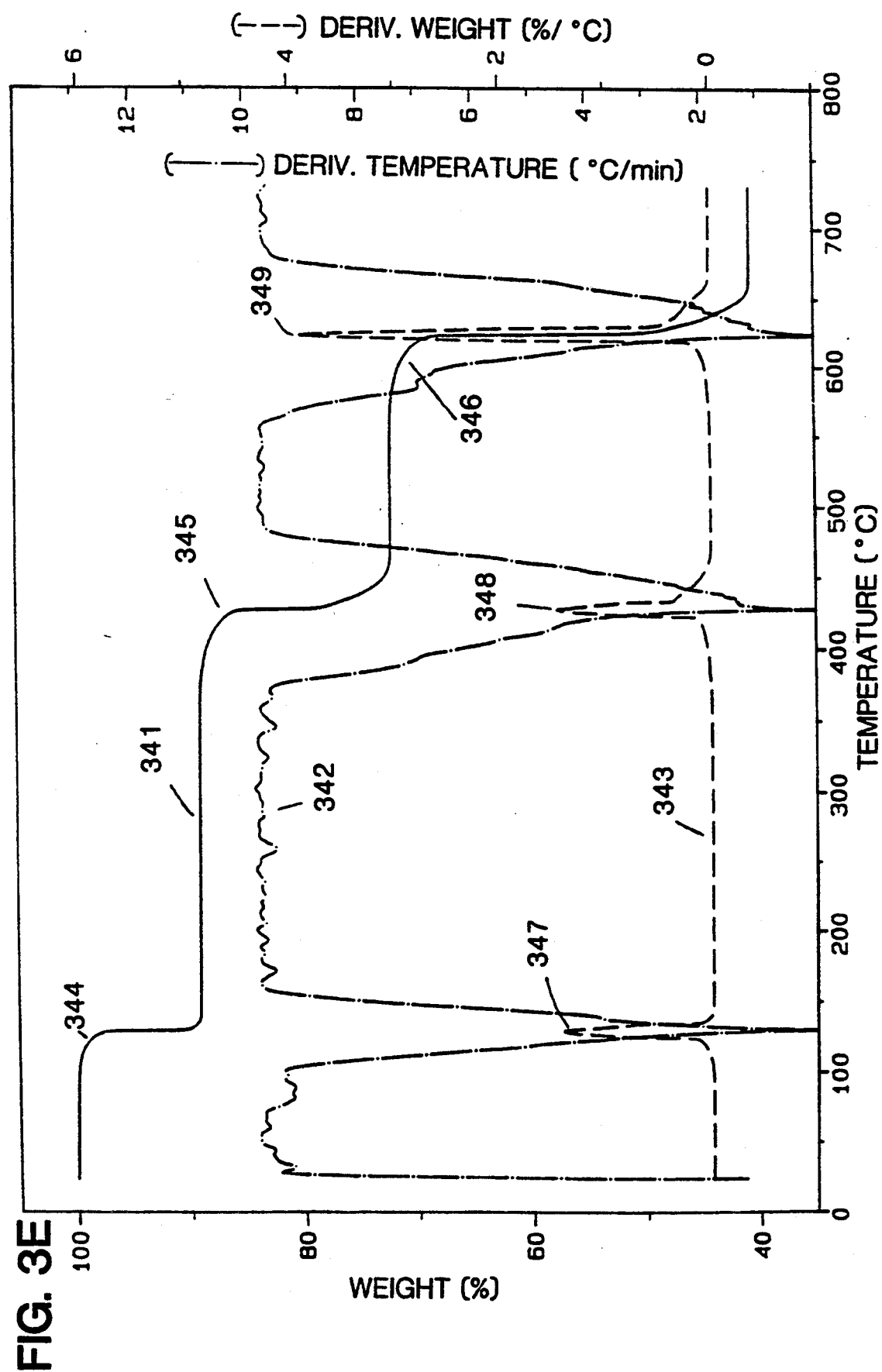

FIGS. 3d and 3e show apparent anomalies at the tail ends of features 338 and 339 (FIG. 3d), and features 348 and 349 (FIG. 3*e*), which are not expected in constant heating rate TGA scans of calcium oxalate. These features are due to plotting the weight loss versus temperature, as the heating rate of the sample is changing. The magnitude of the apparent anomalies is due to the specific implementation and parameters used in this example. These apparent anomalies may be removed by selecting other values for the maximum heating rate and resolution settings.

As shown in FIGS. 3*b*–3*e*, decreasing the maximum heating rate while maintaining a constant resolution setting of 5 results in progressively less transition temperature overshoot, except for the setting of 10° C./minute, which shows no significant improvement over the scan at 20° C./min. In each case, a much sharper weight loss transition is obtained compared to the transition obtained using the conventional constant rate scan shown in FIG. 3*a*. Weight loss baseline is excellent in all scans.

EXAMPLE 4:IMPROVED SEPARATION DEMONSTRATION USING THREE TGA SCANS OF BLACK ELECTRICAL TAPE

Samples of commercially available black electrical tape, a co-polymer sheet with an inorganic adhesive coating on one surface, were examined using conventional TGA (TGA scans shown in FIGS. 4*a* and 4*b*) and using the first preferred embodiment of the present invention (TGA scan shown in FIG. 4*c*), to compare the results obtained by each method. The experimental procedures followed in this example for preparing the apparatus, loading the samples, and running analyses were described in Example 1. In the conventional constant heating rate TGA scan shown in FIG. 4*a*, a 6.34 milligram sample of tape was analyzed in air from ambient temperature to 650 degrees Celsius at a constant heating rate of 50° C./minute. In the conventional constant heating rate scan shown in FIG. 4*b*, a 9.59 milligram sample of tape was analyzed in air from ambient temperature to 650 degrees Celsius at a constant heating rate of 1° C./minute. In the TGA scan obtained according to the first preferred embodiment (steps 1–14) of the present invention shown in FIG. 4*c*, an 8.80 milligram sample of tape was analyzed in air from ambient temperature to 650 degrees Celsius at a heating rate of 50° C./minute and a resolution setting of 4.

Figure 4B:
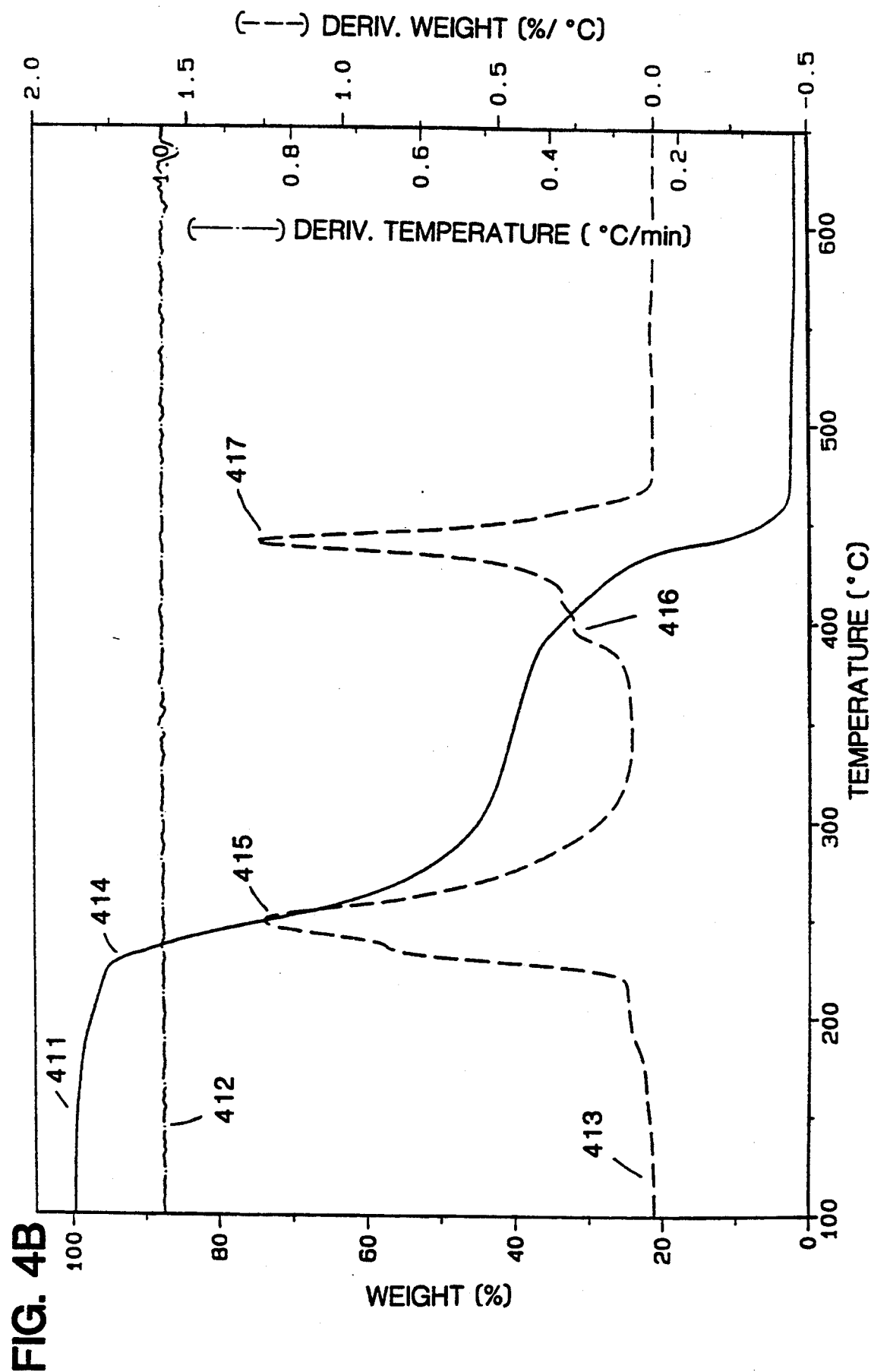
Figure 4C:
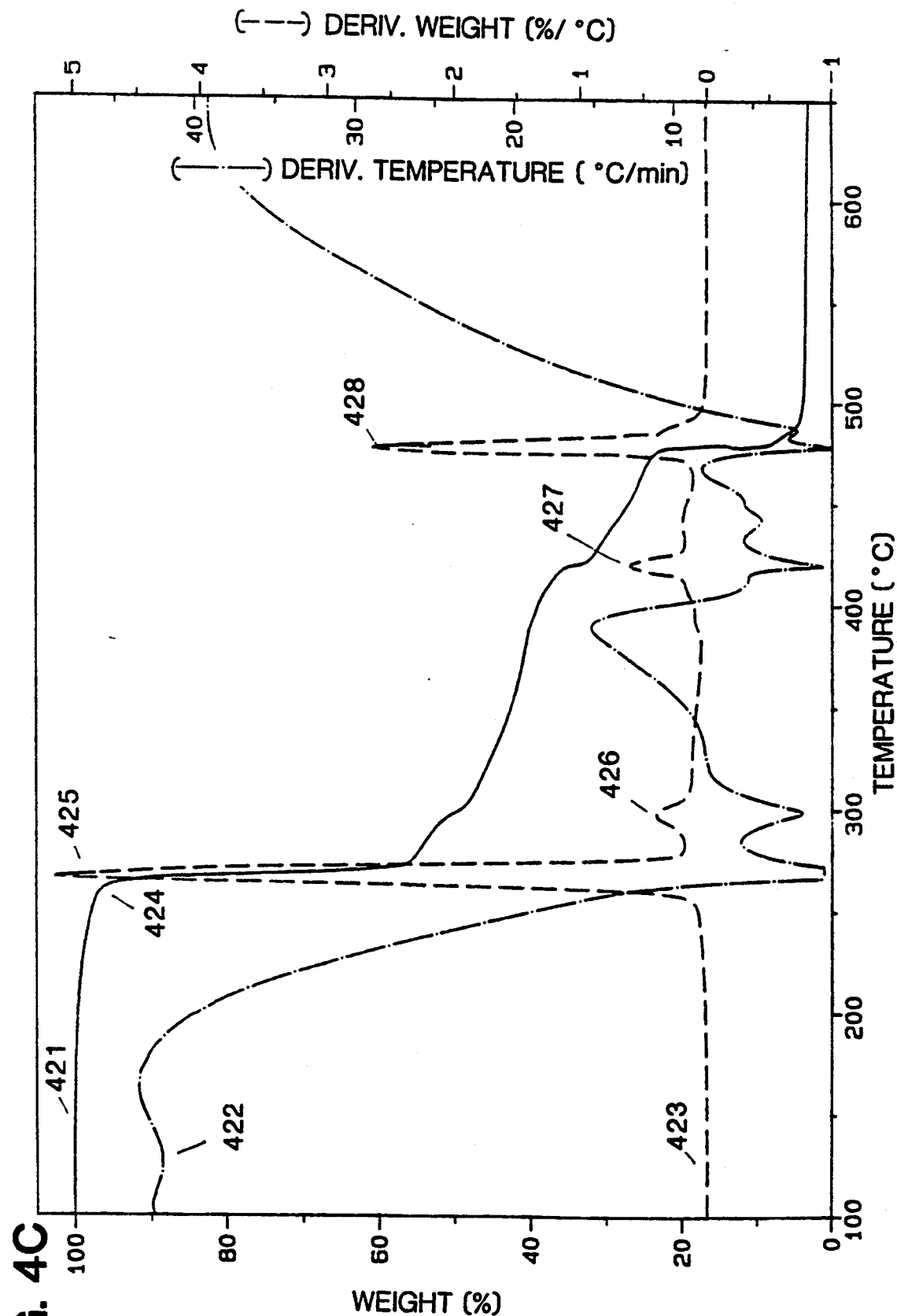

The results of the analyses are shown in FIGS. 4*a*–4*c*. Curves 401 (FIG. 4*a*), 411 (FIG. 4*b*) and 421 (FIG. 4*c*) are plots of the percent weight change of the sample as a function of sample temperature. Curves 402 (FIG. 4*a*), 412 (FIG. 4*b*) and 422 (FIG. 4*c*) are plots of the derivative with respect to time of the sample temperature as a function of sample temperature. Curves 403 (FIG. 4*a*), 413 (FIG. 4*b*) and 423 (FIG. 4*c*) are plots of the derivative with respect to temperature of the percent weight change of the sample as a function of sample temperature.

Features 404 and 405 in FIG. 4*a* and 414 and 415 in FIG. 4*b* appear with much greater resolution in FIG. 4*c* as features 424 and 425. Moreover, peak 426 which is clearly resolved in FIG. 4*c*, is an unresolved component of peak 405 in FIG. 4*a* and peak 415 in FIG. 4*b*. Features 406 and 407 in FIG. 4*a* and 416 and 417 in FIG. 4*b* appear as features 427 and 428 in FIG. 4*c*.

As shown by FIGS. 4*a* and 4*b*, several temperature-overlapped transitions occur between 100° and 350° C., and again between 370° and 550° C. Several of these transitions are difficult to discern in the 50° C./minute scan. In the 1° C./minute scan the overlapped transitions at 240° C. and at 400° C. are still not resolved even though the heating rate has been reduced dramatically. In sharp contrast to these scans is the 50° C./minute scan obtained according to the present invention, which cleanly separates four of the transitions, and shows a significant indication of additional minor transitions. It is evident that the conventional technique of running a fast heating rate survey scan followed by a slow scan to separate transitions at critical points would not have produced results comparable to the scan shown in FIG. 4*c*. Thus, the present invention affords resolution enhancement that cannot be achieved by constant rate TGA regardless of the heating rate selected.

EXAMPLE 5:IMPROVED SEPARATION DEMONSTRATION USING TWO SCANS OF CANDY TAFFY

Figure 5A:
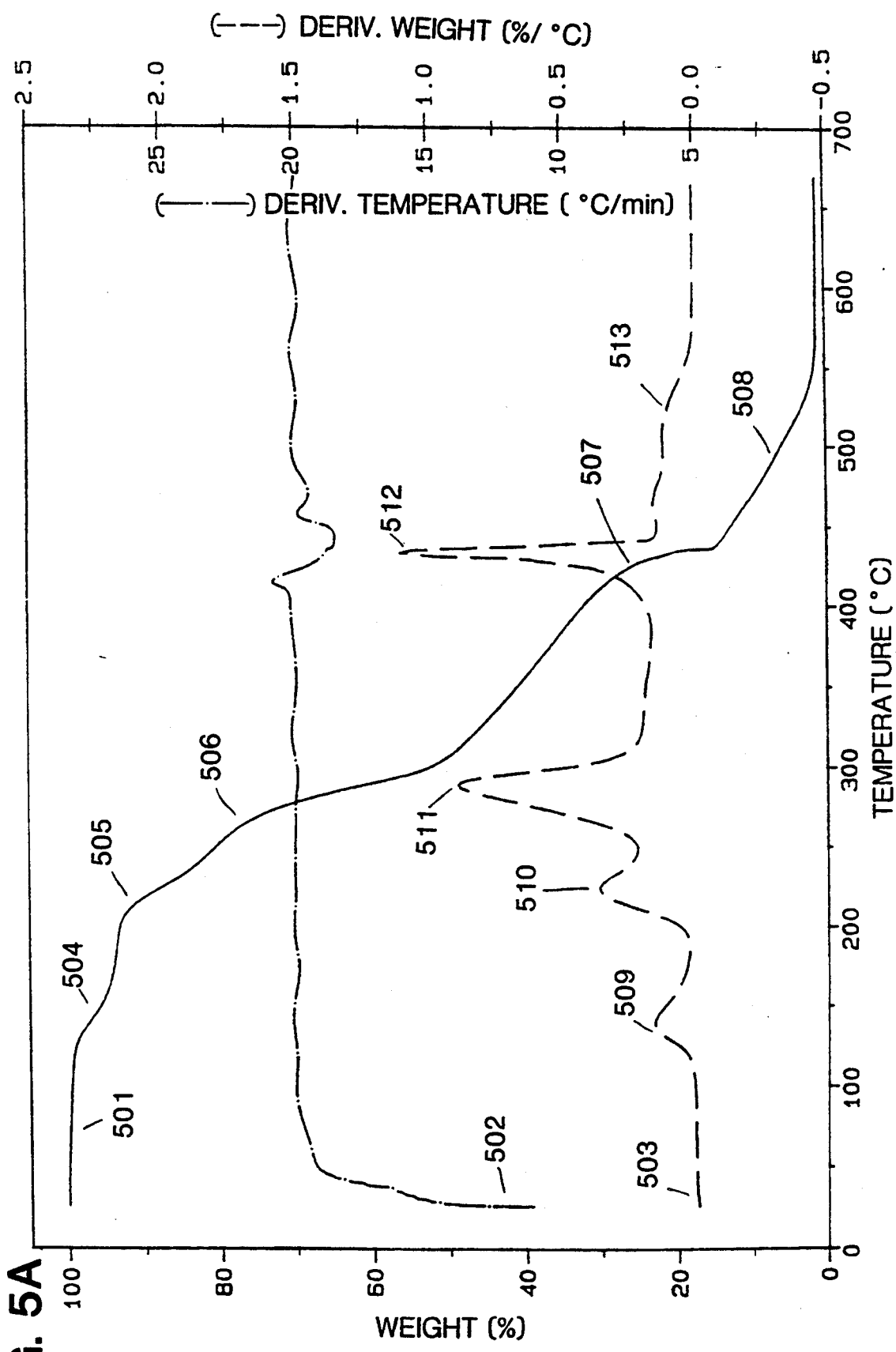
FIGS. 5a-5b are TGA scans of candy taffy obtained according to the methods described in Example 5.
Figure 5B:
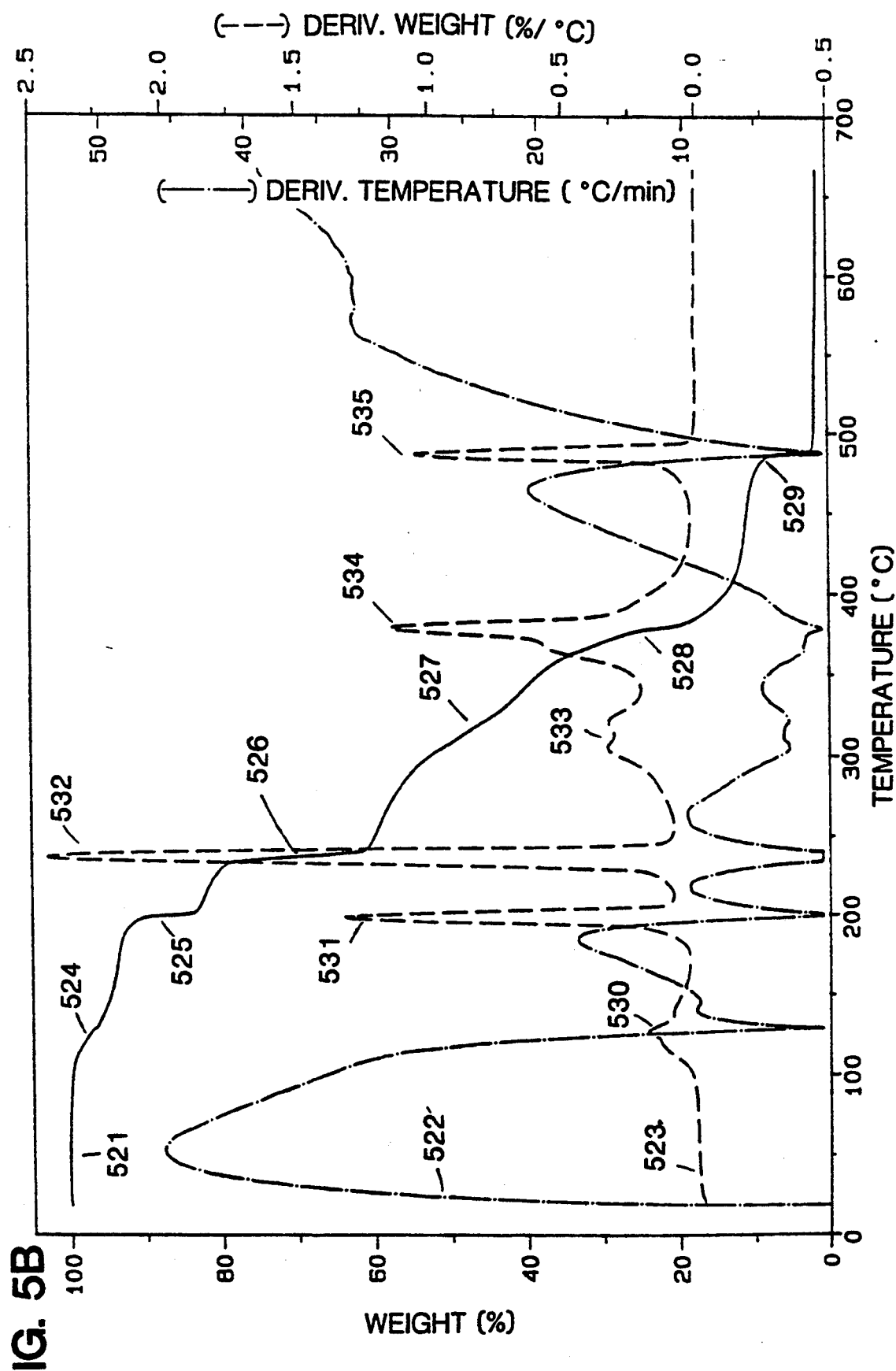

Samples of commercially available candy taffy, a complex mixture of organic compounds, were examined using conventional TGA and using the first preferred embodiment (steps 1–14) of the present invention, to compare the results obtained by each method. The experimental procedures followed in this example for preparing the apparatus, loading the samples, and running analyses were described in Example 1. In FIG. 5*a*, a 12 milligram sample of taffy was analyzed in air from ambient temperature to 670 degrees Celsius at a constant heating rate of 20° C./minute. In FIG. 5*b*, a 12 milligram sample of taffy was analyzed in air, from ambient temperature to 670 degrees Celsius, according to the first preferred embodiment (steps 1–14) of the present invention at a maximum heating rate of 50° C./minute and at a resolution setting of 4.

Curves 501 (FIG. 5*a*) and 521 (FIG. 5*b*) are plots of the percent weight change of the sample as a function of sample temperature. Curves 502 (FIG. 5*a*) and 522 (FIG. 5*b*) are plots of the derivative with respect to time of the sample temperature as a function of sample temperature. Curves 503 (FIG. 5*a*) and 523 (FIG. 5*b*) are plots of the derivative with respect to temperature of the percent weight change of the sample as a function of sample temperature.

As can be seen in FIGS. 5*a* and 5*b*, many temperature overlapped transitions occur between 100° and 550° C. These transitions are much better resolved in the scan shown in FIG. 5*b*. Features 504, 505, 506, 507 and 508 in FIG. 5*a* appear as features 524, 525, 526, 528 and 529, respectively, in FIG. 5*b*. Feature 527 in FIG. 5*b* does not have a readily discernable counterpart in FIG. 5*a*. Features 509, 510, 511, 512, and 513 in FIG. 5*a* appear as features 530, 531, 532, 534 and 535 in FIG. 5*b*. Thus, transitions which were barely perceptible in the conventional scan at 350° C. and 430° C. (not identified in FIG. 5*a*) are well defined at 315° C. (features 527 and 533) and 365° C. (shoulder on feature 534) in the scan obtained according to the present invention. The final weight loss transition, features 529 and 535, is sharply defined in the scan shown in FIG. 5*b*, but appears as a gradual sloping decomposition in the conventional scan shown in FIG. 5*a*, as features 508 and 513. In all cases the derivative of weight change (percent/°C.) curve in FIG. 5*b* is sharper and better resolved with respect to the baseline compared to the same curve shown in FIG. 5*a*. There is also excellent correlation between the size and location of transitions in the scans shown in FIG. 5*a* and 5*b*. FIG. 5*b* shows lower transition temperatures than FIG. 5*a*, especially at higher temperatures. This is because the technique of the present invention reduces transition temperature overshoot, thereby providing a more accurate determination of transition temperatures than the conventional constant heating rate technique.

It is also worth noting in FIG. 5a the sudden increase in the apparent heating rate caused by sample self-heating during combustion at 410 degrees, followed by a reduction in rate as the furnace catches up to the now warmer sample.

EXAMPLE 6: IMPROVED SEPARATION AND RUN TIME DEMONSTRATION USING THREE SCANS OF ETHYLENE-VINYL ACETATE (EVA)

Samples of ethylene-vinyl acetate (EVA) copolymer with 40% vinyl acetate were analyzed using the conventional TGA method and using the first preferred embodiment of the present invention, to compare the results obtained using these methods. This example shows the improved quantitative accuracy of the present invention, compared to the conventional method. The experimental procedures followed in this example for preparing the apparatus, loading the samples, and running analyses were described in Example 1. In the analyses shown in FIGS. 6a, 6b, 6e and 6f, EVA samples were analyzed in nitrogen from ambient temperature to 880 degrees Celsius using the conventional TGA method at a constant heating rate of 20° C./minute (FIGS. 6a and 6b) and 5° C./minute (FIGS. 6e and 6f). FIGS. 6c–6d show TGA scans obtained according to the first preferred embodiment (steps 1–14) of the present invention, using a maximum heating rate of 50° C./minute.

Figure 6A:
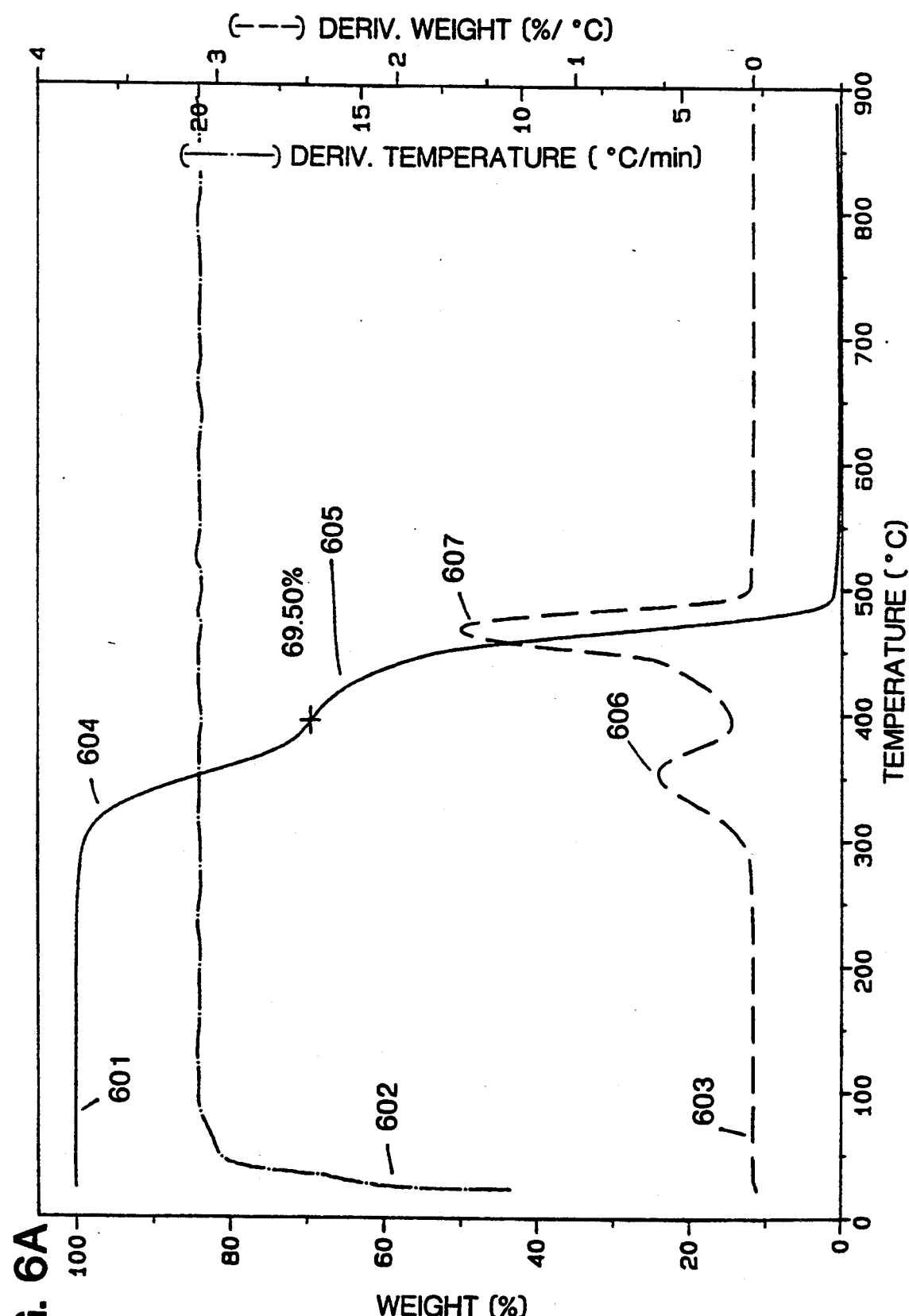
FIGS. 6a-6f are TGA scans of ethylene-vinyl acetate (EVA) obtained according to the methods described in Example 6.
Figure 6B:
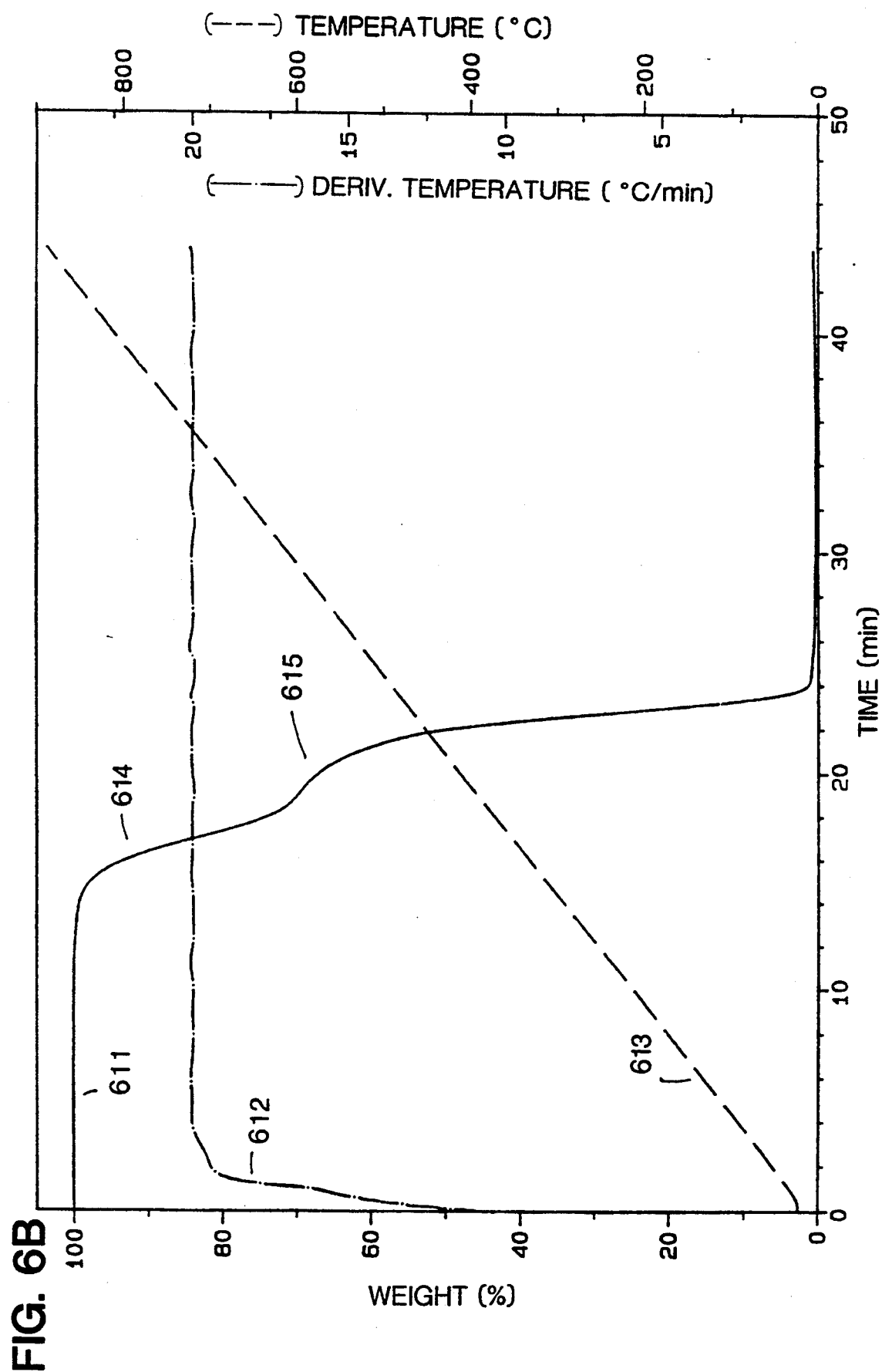
Figure 6C:
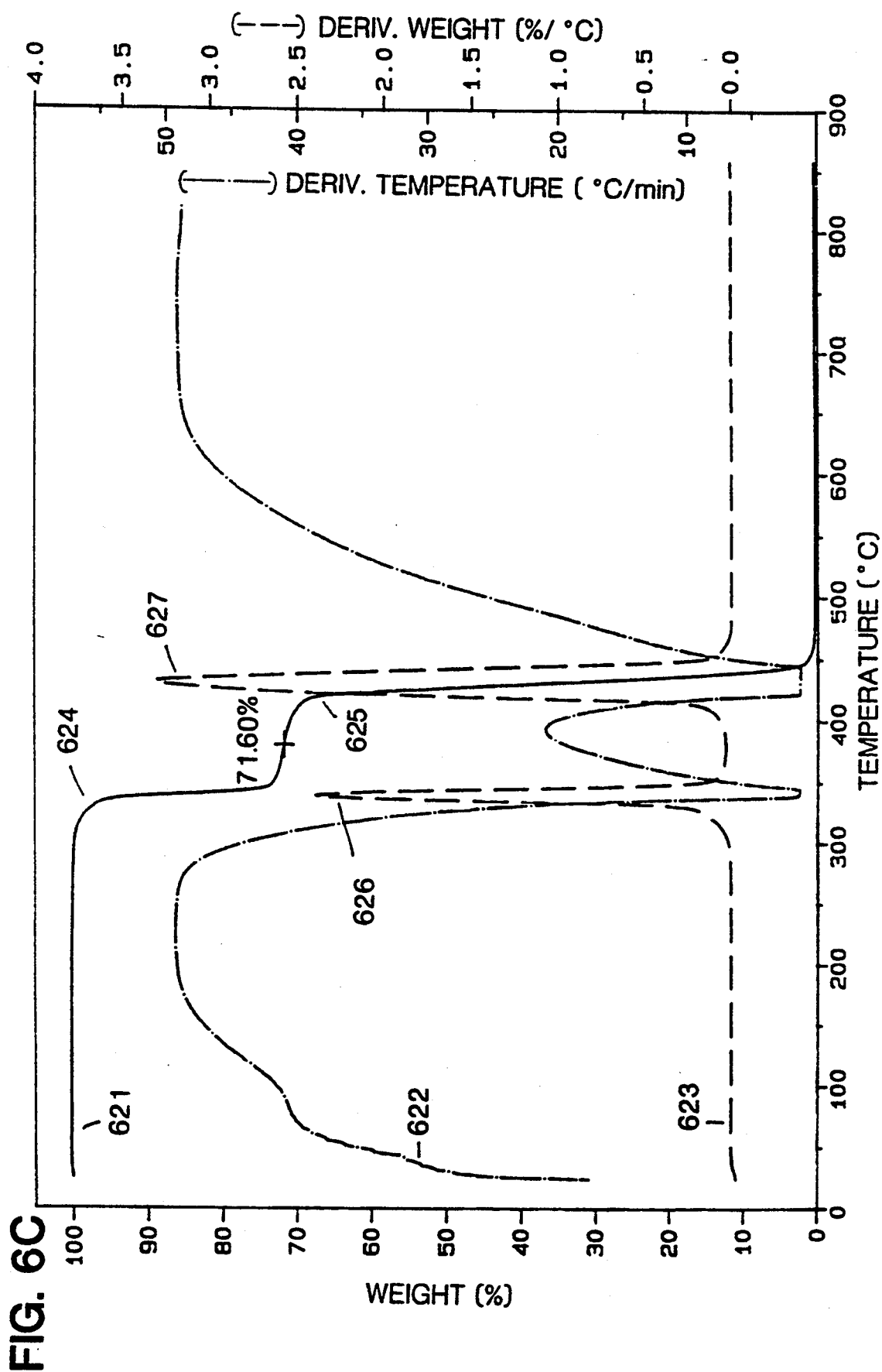
Figure 6D:
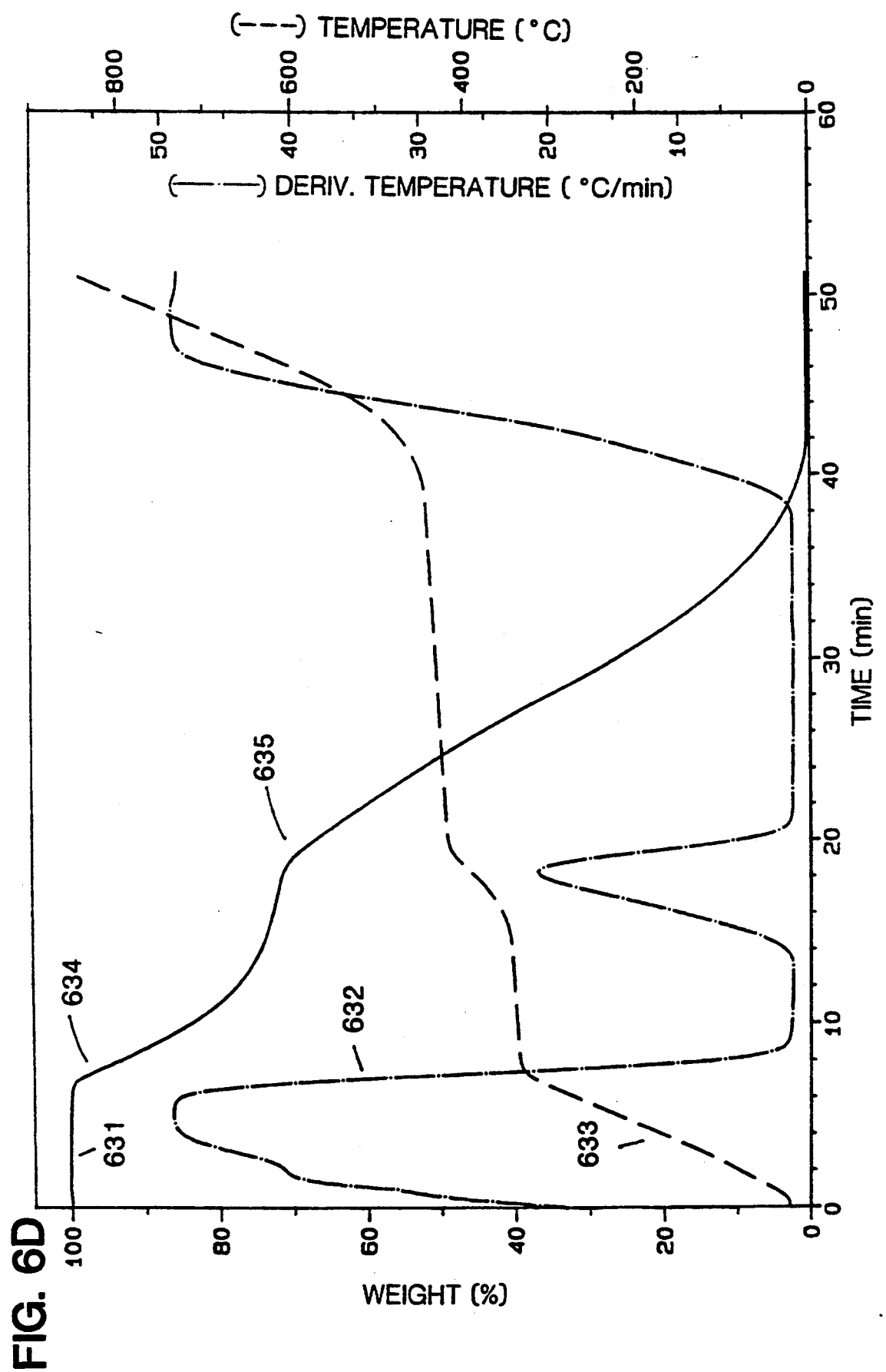
Figure 6E:
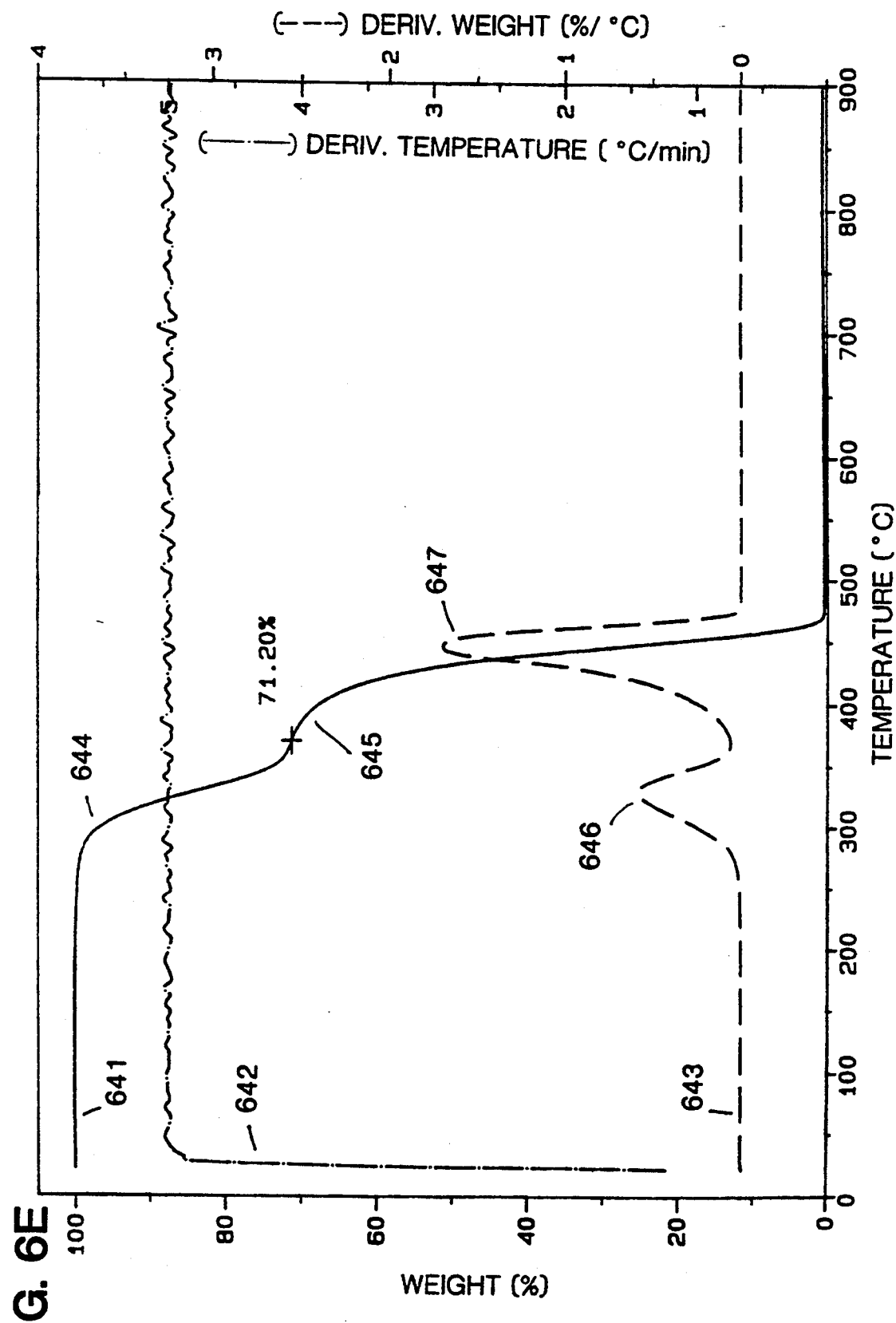
Figure 6F:
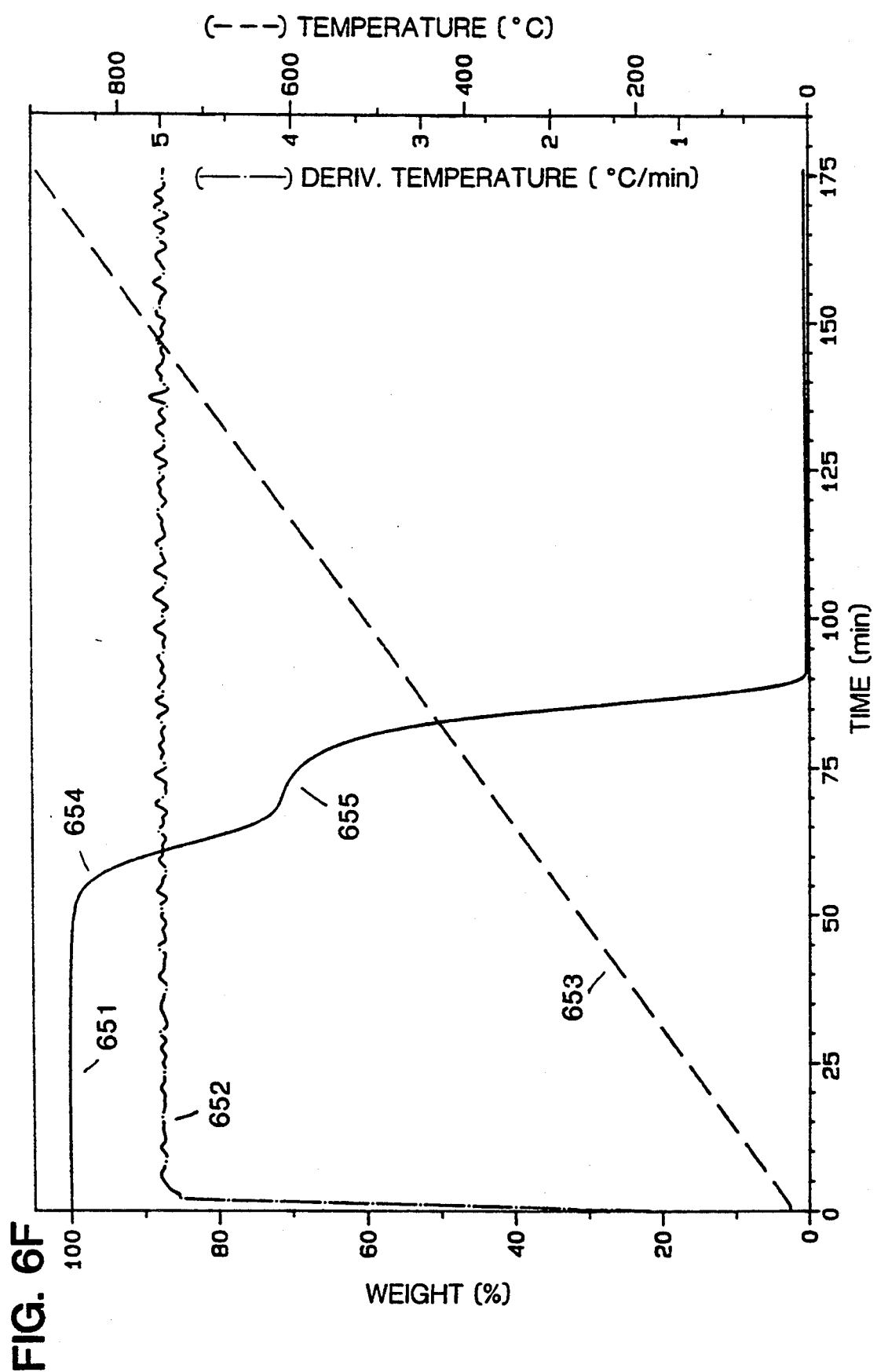

FIGS. 6a, 6c, and 6e show the TGA data plotted versus temperature. Curves 601, 621, and 641 in FIGS. 6a, 6c, and 6e are plots of the percent weight change of the sample as a function of sample temperature. Curves 602, 622, and 642 in FIGS. 6a, 6c, and 6e are plots of the derivative with respect to time of the sample temperature as a function of sample temperature. Curves 603, 623, and 643 in FIGS. 6a, 6c, and 6e are plots of the derivative with respect to time of the percent weight change of the sample as a function of sample temperature.

FIGS. 6b, 6d, and 6f show the TGA data plotted versus time. Curves 611, 631, and 651 in FIGS. 6b, 6d, and 6f are plots of the percent weight change of the sample as a function of time. Curves 612, 632, and 652 in FIGS. 6b, 6d, and 6f are plots of the derivative with respect to time of the sample temperature as a function of time. Curves 613, 633, and 653 in FIGS. 6b, 6d, and 6f are plots of the sample temperature as a function of time. Curves 613 and 653 are straight lines, because that data was obtained using a constant heating rate, whereas curve 633 shows steep high heating rate regions and almost-flat low heating rate regions. FIG. 6d shows that when thermogravimetric analysis is practiced according to the present invention, a greater proportion of the analysis time is generally spent obtaining data during a transition, compared to the conventional method.

FIGS. 6a and 6e show two overlapped transitions between 250 and 500 degrees C. FIG. 6c shows that the same two transitions are clearly separated when thermogravimetric analysis is performed according to the present invention. The first transition is the result of the decomposition of the 40% vinyl acetate in the sample. The first transition appears as features 604 and 606 (FIG. 6a), 614 (FIG. 6b), 624 and 626 (FIG. 6c), 634 (FIG. 6d), 644 and 646 (FIG. 6e), and 654 (FIG. 6f). The second transition, in which the remainder of the sample decomposes, appears as features 605 and 607 (FIG. 6a), 615 (FIG. 6b), 625 and 627 (FIG. 6c), 635 (FIG. 6d), 645 and 647 (FIG. 6e), and 655 (FIG. 6f).

In FIG. 6a, the weight loss from the first transition is difficult to determine because baseline is not re-established before the onset of the second transition. In FIG. 6c the weight loss is much easier to determine because the baseline region between transitions is longer and flatter. The baseline in FIG. 6e is much better established than in FIG. 6a, but is still not as well-defined as in FIG. 6c. This separation permits increased accuracy and increased reproducibility of analyses by decreasing the effect of selecting peak limits and peak overlaps.

In this example, the amount of vinyl acetate in the sample can be determined from the weight loss attained at the point of lowest slope in the weight change curve (i.e., the bottom of the valley between peaks in the derivative of weight change curve), from the following simple relation, described in Jen Chiu, "Applications of Thermogravimetry to the Study of High Polyphers", Applied Polymer Symposia No. 2, pp. 25–43 (1966):

$$\% \text{ vinyl acetate} = \% \text{ weight loss} \times 1.43$$

According to this equation, the percent vinyl acetate in each sample is given by:

sample-1 (FIG. 6a):30.5 weight %×1.43=43.6% vinyl acetate sample-2 (FIG. 6c):28.4 weight %×1.43=40.6% vinyl acetate sample-3 (FIG. 6e):28.8 weight %×1.43=41.2% vinyl acetate These calculations show the improvement in accuracy obtained with the first preferred embodiment of the present invention (sample-2, FIG. 6c) compared to conventional TGA scans at 20° C./minute (sample-1, FIG. 6a) and 5° C./minute (sample-3, FIG. 6e).

The total time required to analyze the first sample using the conventional method at 20° C./minute was 44 minutes (excluding sample preparation, loading and after-test cool down). The time required to analyze the third sample using the conventional method at 5° C./minute was 177 minutes. The time required to analyze the second sample according to the present invention at a maximum heating rate of 50° C./minute was 51 minutes.

These results demonstrate that the improved accuracy of the present invention over the conventional method is attained without a significant decrease in laboratory productivity.

A comparison of the constant heating rate time base plots in FIGS. 6b and 6f with the present invention time base plot in FIG. 6d shows the operating modes of the present invention. In FIGS. 6b and 6f, the weight loss curve appears the same as the weight loss curve in FIGS. 6a and 6e, respectively. This is because time and temperature are both increasing linearly in the constant heating rate technique, as shown by the straight lines of curves 613 and 653.

The weight loss versus time curve in FIG. 6d differs drastically from the weight loss curves in FIGS. 6b and 6f. This is due to the variable heating rate of the present invention. In the present invention, the weight loss per minute is not held constant as in thermogravimetric analysis practiced according to the Paulik quasi-isothermal method.

Key aspects of the present invention are shown by curve 632 of FIG. 6d. During the first few minutes of the experiment, the UPLIFT technique pushes the heating rate to the maximum value set by the operator since no weight is being lost by the sample. At about 5 minutes into the scan, the BASELINE technique detects the beginning of the first transition and rapidly reduces heating rate to the minimum allowable. The heating rate is held at minimum as the weight loss per minute reaches maximum and then subsides to a level within the range of the TRACKING technique. At this point, 13 minutes into the scan, the heating rate is gradually increased primarily due to the influence of the TRACKING technique which strives to maintain the decaying weight loss per minute. At 18 minutes into the scan, the BASELINE technique once again detects the onset of a transition and drives the heating rate to the minimum. The heating rate is held at the minimum for more than 20 minutes while the second transition peaks and subsides. At this point, the TRACKING technique once again raises the heating rate in an effort to maintain the rate of weight loss. At 42 minutes into the scan, the sample has not yet completely decomposed, but the weight loss per minute has fallen to near zero. This reduction in the weight loss per minute triggers the uplift technique to rapidly raise the heating rate to the maximum heating rate set for the analysis, where it remains throughout the remainder of the scan.

EXAMPLE 7: COMPUTER PROGRAM FOR IMPLEMENTING THE FIRST PREFERRED EMBODIMENT OF THE PRESENT INVENTION

The following computer program is an example of a computer program used to control the main steps of the first preferred embodiment of the present invention. Examples 1-6 were implemented using a computer program following an algorithm similar to the algorithm used in this example. However, the computer programs used in Examples 1-6 were not identical to the program disclosed in the present invention. The program is written in PL/M.

PL/M is a high-level computer programming language developed by Intel Corporation. The PL/M language is one of many block structured programming languages (similar to PL/1, Pascal and C) which are based on the ALGOL-60 programming language introduced in the early 1960's. The PL/M language was used to program the control system and high resolution software for the TGA 2950 Thermogravimetric Analyzer used in the experimental apparatus for the first preferred embodiment of the present invention. The steps listed in the first preferred embodiment of the invention described above are referenced in the listing of the computer program herein.

```
HEATING RATE CONTROL PROGRAM - 1
/* TGA Heating Rate Set Point Determination Algorithm.
   This Algorithm executes once every 0.5 seconds. */
/* Definitions of variables used in the heating rate control
   program.
res_setting      current resolution setting (1.0 to 5.0)
wgt_pct          real time weight change (percent)
pct_drv          derivative of wgt_pct with respect to time
                 (percent/minute)
pct_drv_target   pct_drv tracking target (percent/minute)
pct_drv_avg      average derivative of wgt_pct with respect to
                 time (percent/minute)
drv_delay_ctr    time delay counter for avg wgt_pct_deriv
                 calculation
```

```
-continued
HEATING RATE CONTROL PROGRAM - 1
rate_max         maximum heating rate (deg C./minute)
rate_min         minimum heating rate (deg C./minute)
rate_now         current heating rate (deg C./minute)
rate_new         new heating rate (deg C./minute)
range_used       fraction of allowed heating rate range used
                 (0.0 to 1.0)
rate_error       total heating rate error factor (deg
                 C./minute)
rate_baseline_err weight change baseline deviation factor (deg
                 C./minute)
rate_tracking_err weight change tracking factor (deg C./minute)
rate_uplift_err  rate uplift factor (deg C./minute) */
Do
/* STEP 1 */
          /* The maximum heating rate in degrees
             C./minute is selected by the operator prior
             to the start of the experiment and is stored
             by the computer in variable
             "rate_max". */
/* STEP 2 */
          /* The resolution setting (range 1.0 to 5.0) is
             selected by the operator prior to the start of
             the experiment and is stored by the
             computer in variable "res_setting". */
/* STEP 3 */
          /* Compute minimum heating rate from
             maximum. The minimum ranges from 20%
             to 0.37% of the maximum rate depending
             on the resolution setting. (Lowest minimum
             heating rate occurs at the highest resolution
             setting.) */
rate_min = rate_max * EXP(6.3 - resolution) / 1000.0;
          /* Limit the minimum heating rate to 0.01
             degrees C./min. This is the slowest rate the
             heater controller for the TGA 2950 can
             effectively control. */
If rate_min < 0.01 Then
     rate_min = 0.01;   /* 0.01 deg C./minute
                           minimum */
/* STEP 4*/
          /* The absolute weight change as a percent of
             initial weight is monitored by the computer
             in real time and stored in wgt_pct. */
/* STEP 5 */
          /* The derivative of the weight change with
             respect to time is calculated by the
             computer in real time from wgt_pct and
             stored in pct_drv. */
/* STEP 6 */
          /* Delay calculation of the %/minute average
             to allow any ringing or overshoot in the
             weight %/min to dampen out. The average
             is computed with an exponential filter with a
             time constant of about 25 seconds.
             (drv_delay_ctr is initialized to 30 prior to
             start of the method.) */
If drv_delay_ctr > 0 Then
     Do;             /* Delay active */
     drv_delay_ctr = drv_delay_ctr - 1;
     pct_drv_avg = pct_drv;  /* Init
                                average */
     End;
Else                /* Compute average %/minute */
     pct_drv_avg = pct_drv_avg * 0.98 +
                   pct_drv * 0.02;
/* STEP 7 */
          /* Compute the fraction of the total allowable
             heating rate range which is currently in use
             (i.e., how far is the current heating rate
             from the minimum heating rate as a fraction
             of the range between minimum and
             maximum heating rate). This value is used to
             control the percentage of baseline and
             tracking error to use in the error
             calculations. */
range_used =
     (rate_now - rate_min) / (rate_max -
     rate_min);
/* STEP 8 */
          /* Compute rate change desired due to
```

HEATING RATE CONTROL PROGRAM - 1
*-continued*

```
                deviation from the current weight loss per
                minute baseline. This permits the system to
                track a low weight loss baseline without
                severely reducing the heating rate. This
                factor is primarily responsible for detecting
                the beginning of a transition and then
                reducing the heating rate quickly. The effect
                of this tracking is greatest at heating rates
                close to rate__max and is linearly reduced
                to zero as rate__min is approached. */
                rate__baseline__err = 1.0 * range__used *
                    ABS(pct__drv__avg - pct__drv);
/* STEP 9 */
             /* Compute rate change desired due to
                deviation from the desired weight loss per
                minute. This causes the system to track
                constant weight loss during periods of
                moderate weight loss. This speeds up total
                experiment time and helps accentuate weight
                loss transitions. The tracking target ranges
                linearly from 2.5 to 0.5
                %/minute from the lowest to the highest
                resolution setting. The effect of this tracking
                is greatest at heating rates close to rate min
                and is linearly reduced to zero as rate__max
                is approached. */
                pct__drv__target = 3.0 - res__setting * 0.5;
                rate__tracking__err) = 0.1 * (ABS(pct__drv) -
                    pct__drv__target) * (1.0 - range__used);
/* STEP 10 */
             /* Compute rate change desired due to very
                low weight loss. This factor helps to drive
                the heating rate up to maximum when very
                little weight is being lost. This occurs
                between very well resolved transitions and
                especially after ash formation (no more
                weight loss possible). The uplift calculation
                is restricted to prevent numeric blowups at
                weight loss extremes. */
                If ABS(pct__drv__avg) >= 1.0 Then
                /* Rapid loss? */
                    rate__uplift__err = 0.0;
                    /* Force lower limit */
                Else
                    If ABS(pct__drv__avg) <= 0.0001 Then/*
                    No loss? */
                        rate__uplift__err = -0.1;/*
                        Force upper limit */
                    Else
                        rate__uplift__err = 0.025 *
                            LOG(ABS(pct__drv__avg));
/* STEP 11 */
             /* Compute the total heating rate error factor
                by summing the individual components of
                error. Then subtract the error factor from
                the current heating rate to get the new rate.
                (A negative error factor will produce an
                increase in heating rate.) */
                rate__error = rate__baseline__err +
                    rate__tracking__err +
                    rate__uplift__err;
                rate__new = rate__now - rate__error;
/* STEP 12 */
                */ Limit the new rate to the maximum heating
                rate allowed */
                If rate__new > rate__max Then
                    rate__new = rate__max;
/* STEP 13 */
             /* Limit the new rate to the minimum heating
                rate allowed */
                If rate__new < rate-min Then
                    rate__new = rate__min;
/* STEP 14 */
             /* Save the new heating rate for heater
                control. */
                rate__now = rate__new;
                End;
```

EXAMPLE 8: IMPROVED SEPARATION DEMONSTRATION USING TWO SCANS OF CANDY TAFFY

Figure 8A:
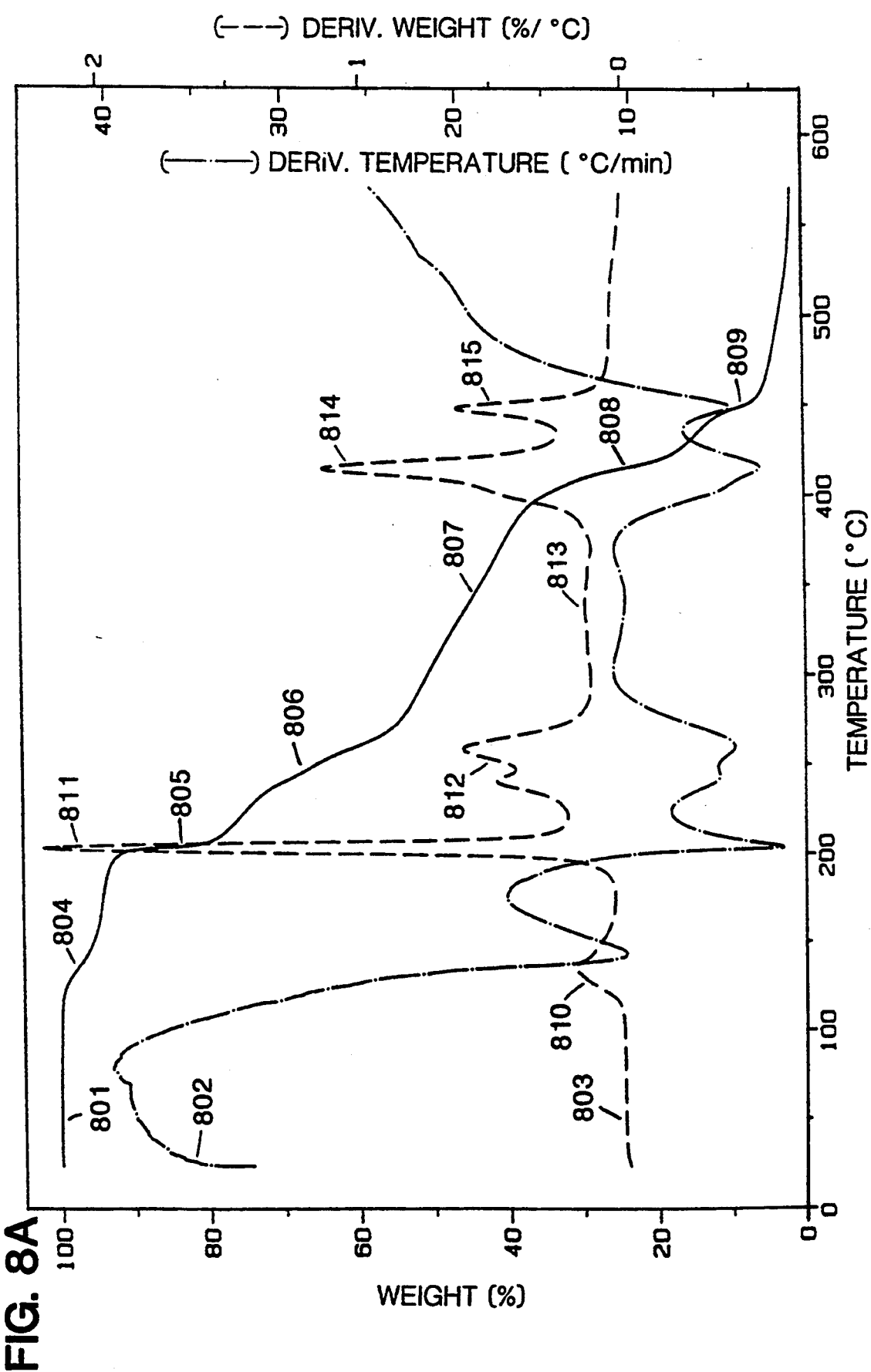
FIGS. 8a-8d are TGA scans of candy taffy obtained according to the methods described in Example 8.
Figure 8B:
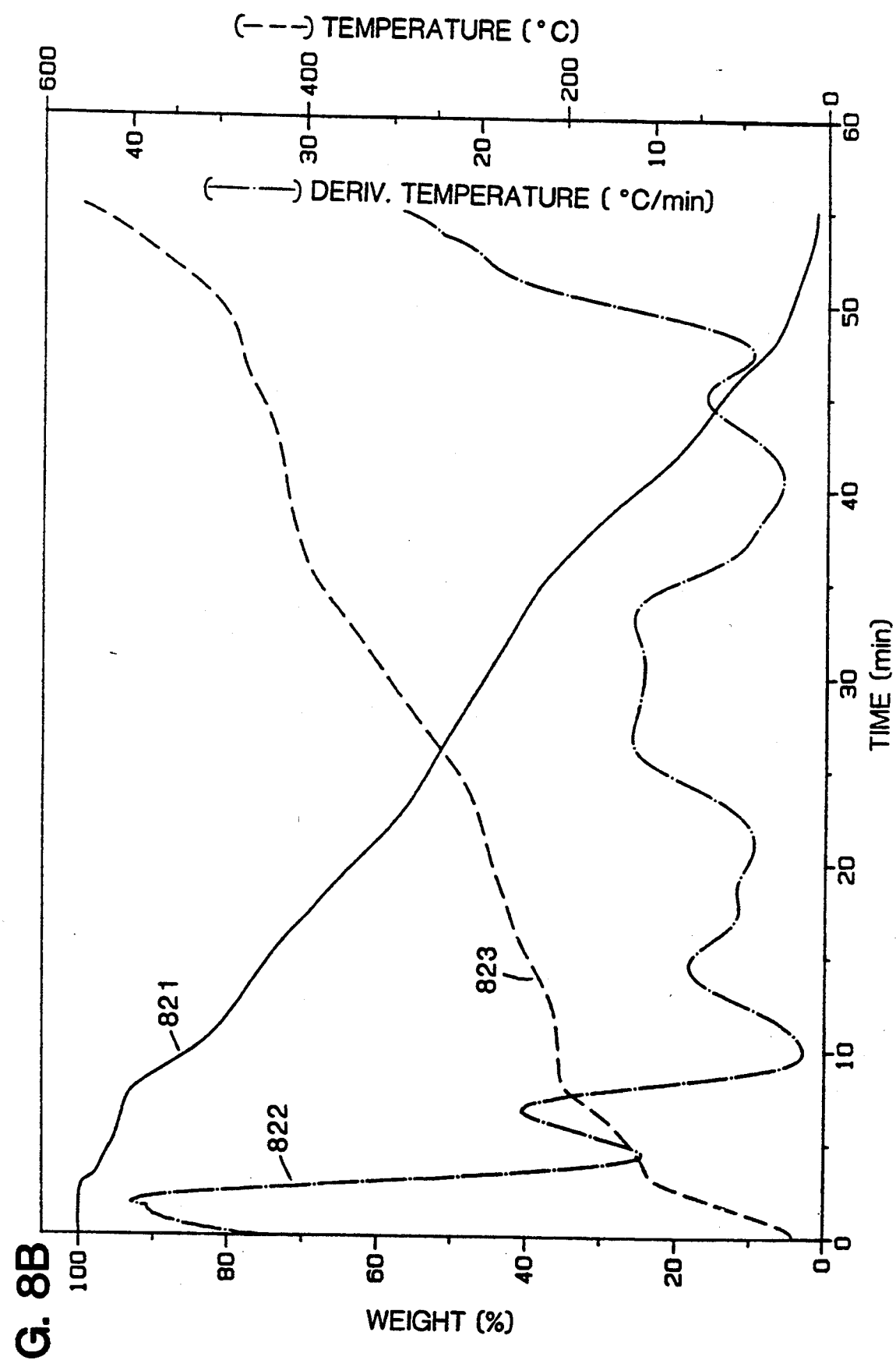
Figure 8C:
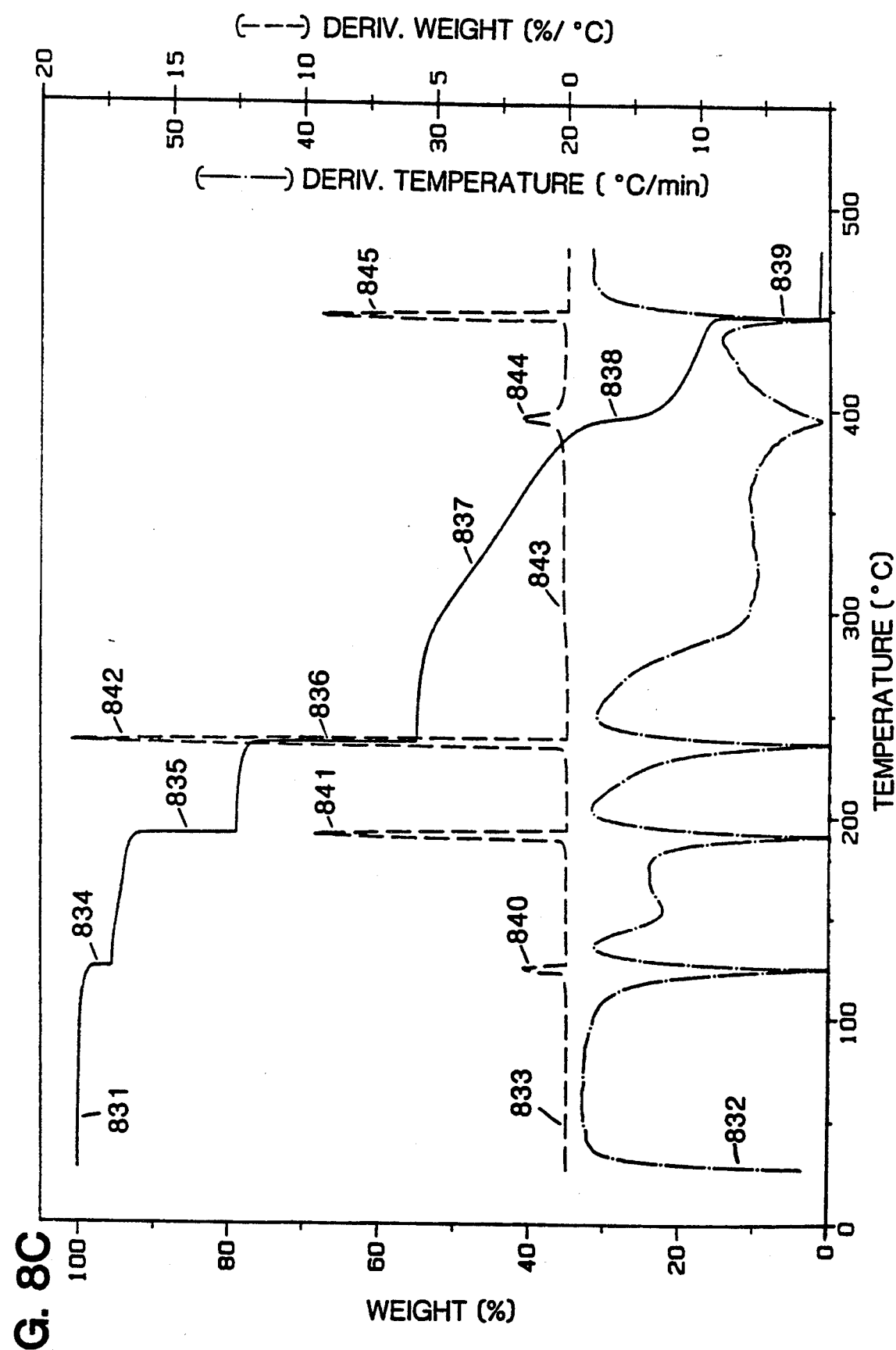
Figure 8D:
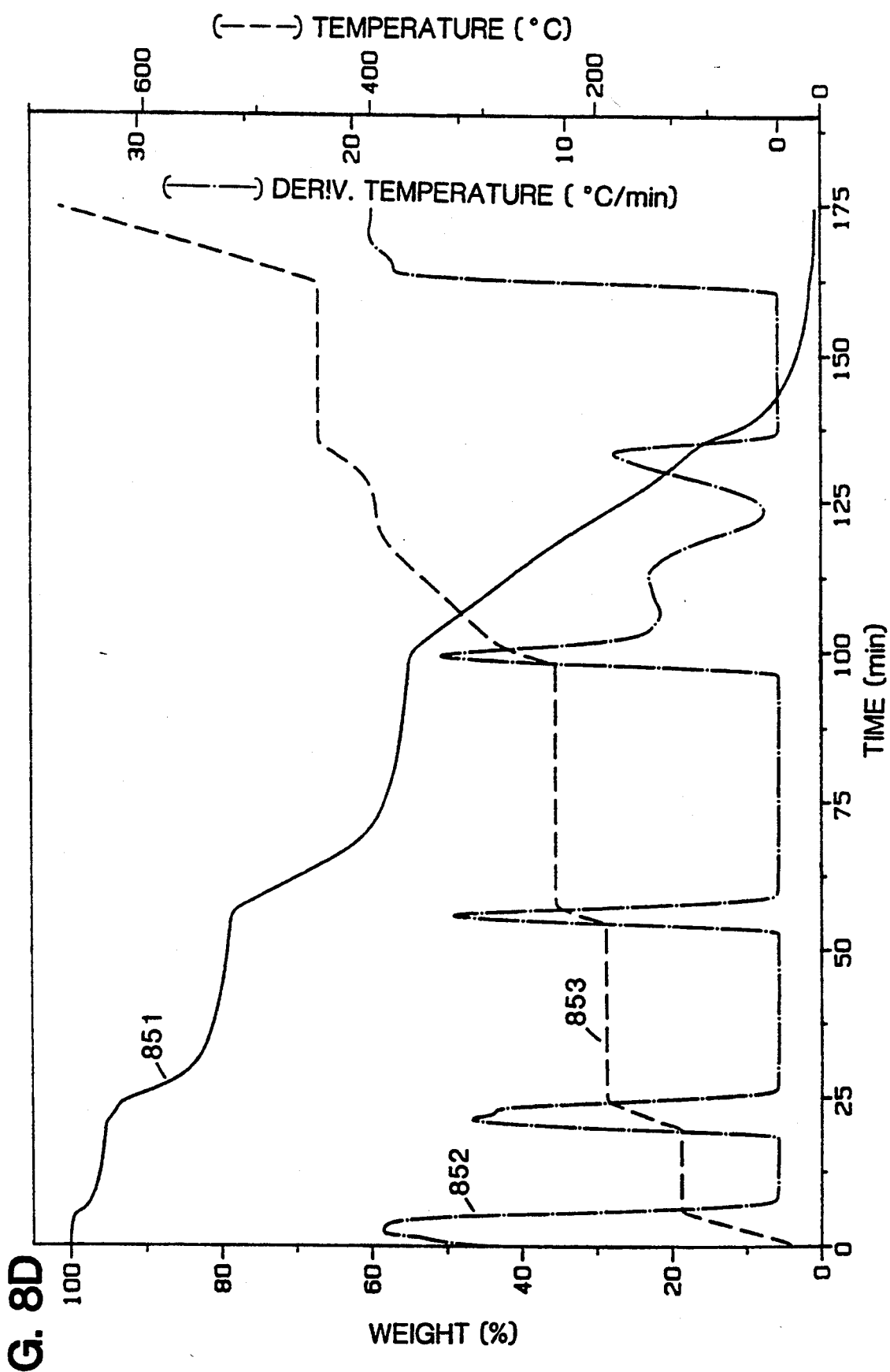

Samples of commercially available candy taffy (the same material as was used in Example 5) were examined by the method (steps 1-14) of the second preferred embodiment of the present invention to compare the results obtained by each mode of the present invention with the scans of Example 5. The experimental procedures followed in this example for preparing the apparatus, loading the samples, and running analyses were described in Example 1. In FIGS. 8a and 8b, a 22 milligram sample of taffy was analyzed in air, from ambient temperature to 570 degrees Celsius, using the first mode of operation (steps 1-14) of the second preferred embodiment of the present invention at a maximum heating rate of 50° C./minute and at a resolution setting of 4.0. In FIGS. 8c and 8d, a 15 milligram sample of taffy was analyzed in air, from ambient temperature to 480 degrees Celsius, using the second mode of operation (steps 1-14) of the second preferred embodiment of the present invention at a maximum heating rate of 20° C./minute and at a resolution setting of −3.5.

FIGS. 8a and 8c show the TGA data plotted versus temperature. Curves 801 (FIG. 8a) and 831 (FIG. 8c) are plots of the percent weight change of the sample as a function of sample temperature. Curves 802 (FIG. 8a) and 832 (FIG. 8c) are plots of the derivative with respect to time of the sample temperature as a function of sample temperature. Curves 803 (FIG. 8a) and 833 (FIG. 8c) are plots of the derivative with respect to temperature of the percent weight change of the sample as a function of sample temperature.

FIGS. 8b and 8d show the TGA data plotted versus time. Curves 821 (FIG. 8b) and 851 (FIG. 8d) are plots of the percent weight change of the sample as a function of time. Curves 822 (FIG. 8b) and 852 (FIG. 8d) are plots of the derivative with respect to time of the sample temperature as a function of time. Curves 823 (FIG. 8b) and 853 (FIG. 8d) are plots of the sample temperature as a function of time.

The scans in FIGS. 8a and 8c can be readily compared to the constant heating rate scan in FIG. 5a and the high resolution scan in FIG. 5b. Features 504, 505, 506, 507 and 508 in FIG. 5a appear as features 804, 805, 806, 808 and 809, respectively, in FIG. 8a, and as features 834, 835, 836, 838 and 839, respectively, in FIG. 8c. Features 807 and 837 in FIGS. 8a and 8c, respectively, do not have a readily discernable counterpart in FIG. 5a. Features 509, 510, 511, 512 and 513 in FIG. 5a appear as features 810, 811, 812, 814 and 815, respectively, in FIG. 8a, and as features 840, 841, 842, 844 and 845, respectively, in FIG. 8c. As can be seen, the many temperature-overlapped transitions occurring between 100° and 550° C. are much better resolved in the scans shown in FIGS. 8a and 8c than in FIG. 5a, and are similar to the scan shown in FIG. 5b. The weight loss transitions at 834, 835, 836 and 839 in FIG. 8c are extremely sharp thereby allowing very accurate determination of the respective decomposition temperatures of those transitions. In all cases, the derivative of weight change (percent/°C.) curves in FIGS. 8a and 8c are sharper and better resolved with respect to the baseline compared to the same curves shown in FIG. 5a. As in FIG. 5b, there is excellent correlation between the size and location of transitions in the scans shown in FIGS. 8a and 8c.

FIGS. 8*b* and 8*c* may be compared to better understand the difference between mode 1 operation (FIG. 8*b*) and mode 2 operation (FIG. 8*d*). Curve 822 in FIG. 8*b* and curve 852 in FIG. 8*d* show the heating rate (°C./minute) of the sample as a function of time. In FIG. 8*b* it can be seen that the heating rate changes slowly and continuously in response to changes in weight loss. This is reflected in the temperature curve, 823, which maintains a positive but varying slope. This contrasts with the heating rate curve, 852, in FIG. 8*d* which changes rapidly from approximately 70% of maximum to near zero every time a major transition is encountered. The heating rate is fixed at a constant 0.01° C./minute for the duration of each major transition after which it rises again rapidly. This results in the stair-step temperature versus time curve 853, and the very sharp derivative of weight loss peaks shown in FIG. 8*c*.

EXAMPLE 9: IMPROVED SEPARATION DEMONSTRATION USING TWO SCANS OF ETHYLENE-VINYL ACETATE (EVA)

Figure 9A:
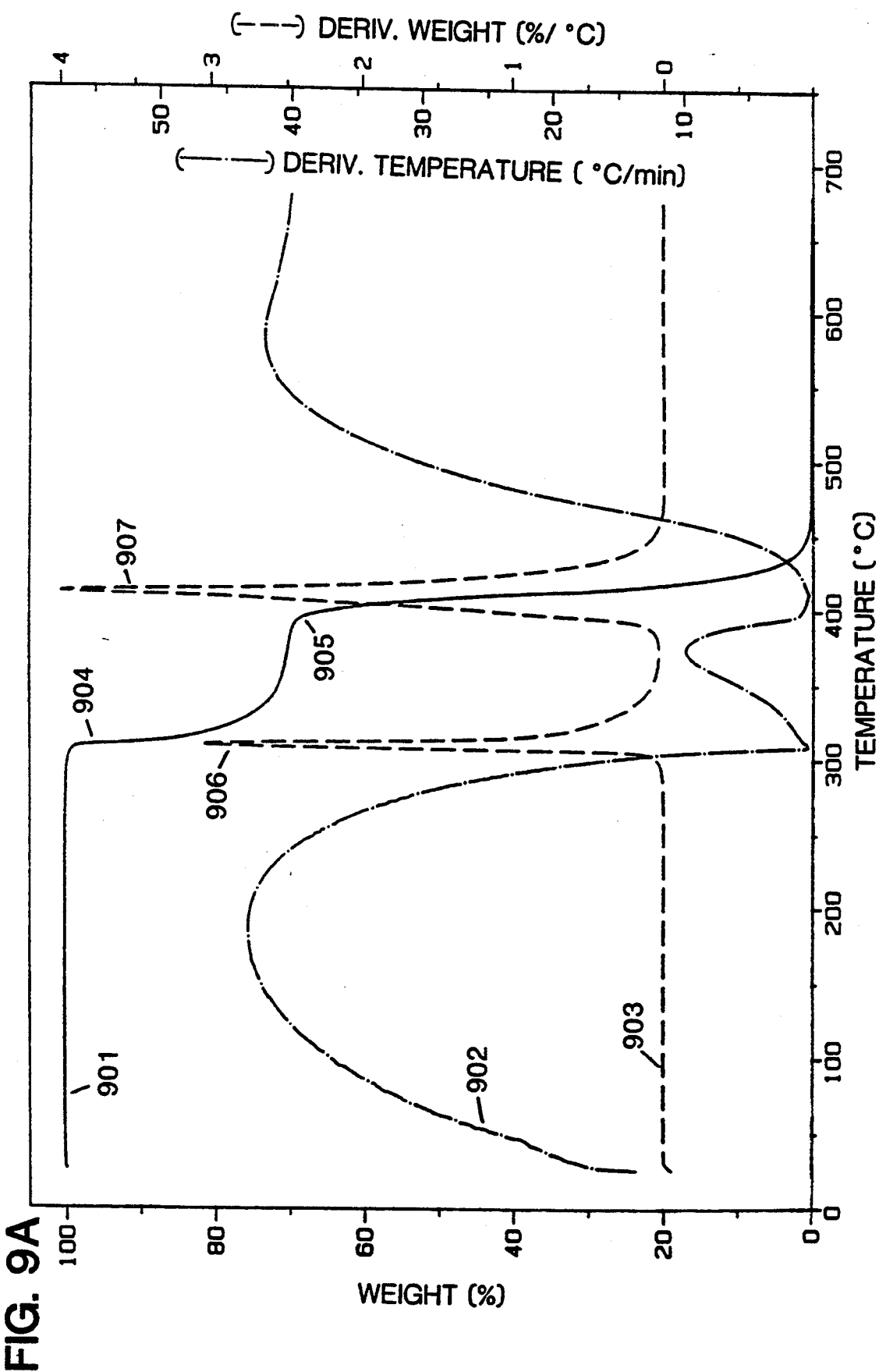
FIGS. 9a-9d are TGA scans of ethylene-vinyl acetate (EVA) obtained according to the methods described in Example 9.
Figure 9B:
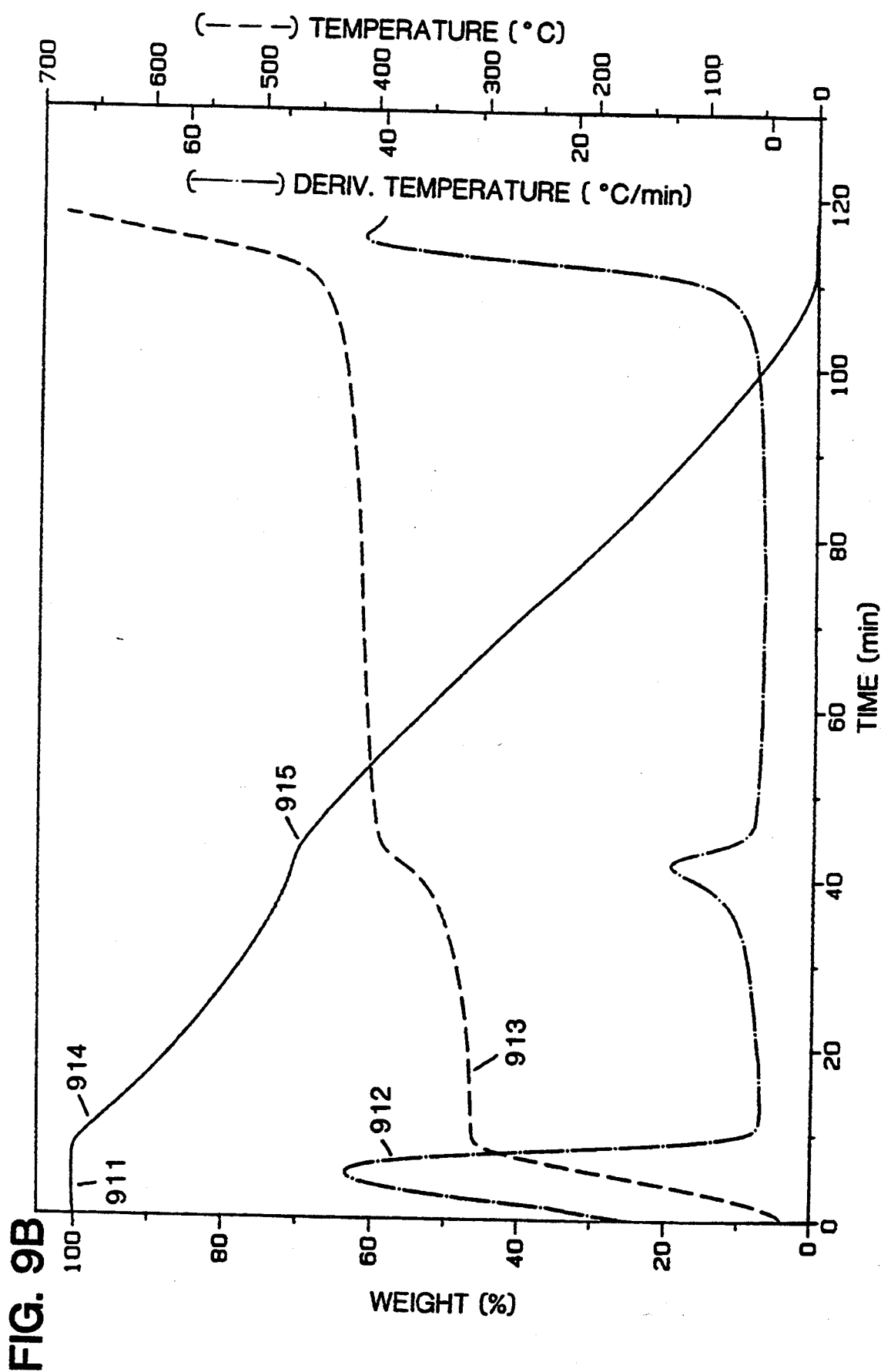
Figure 9C:
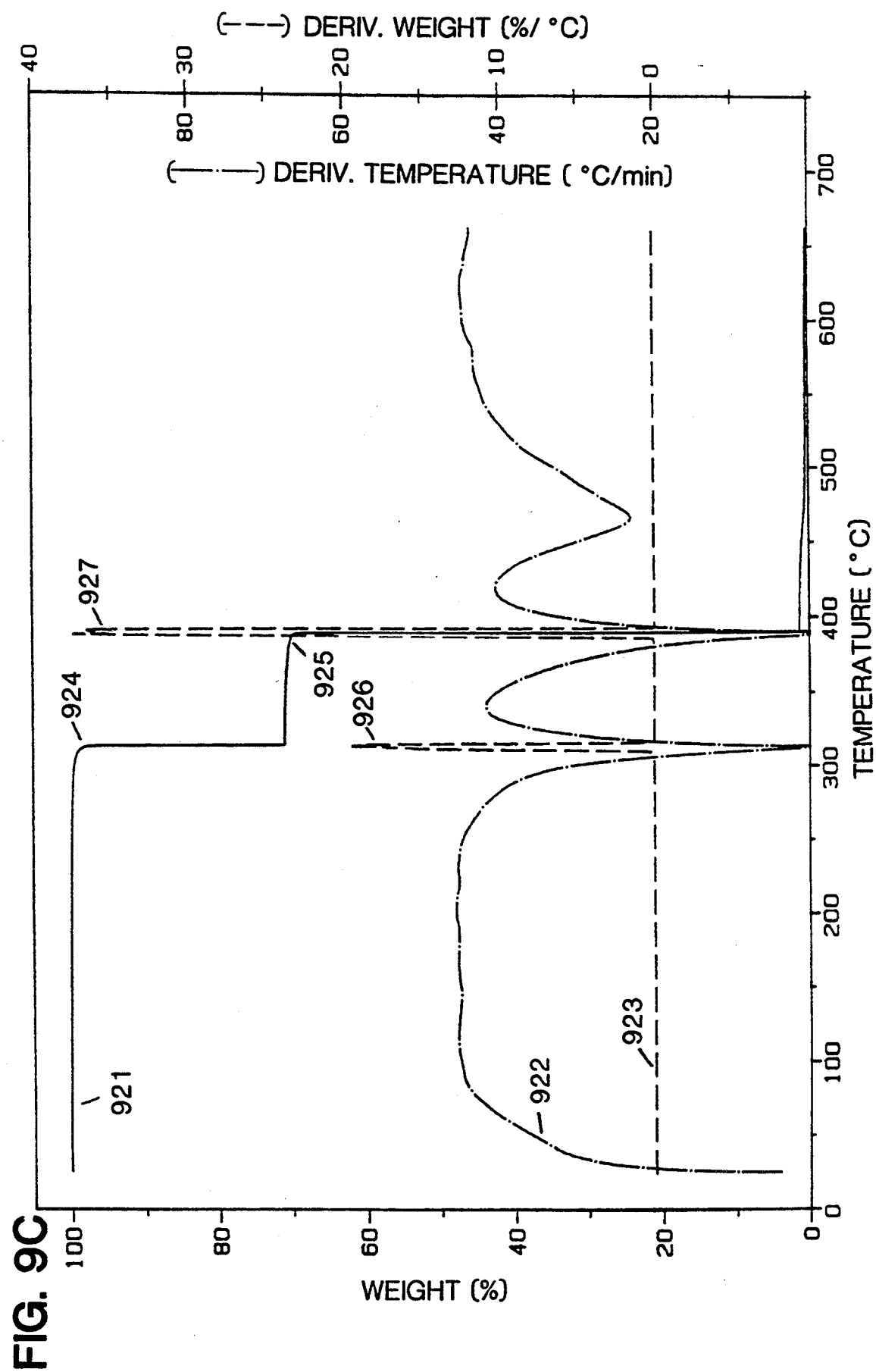
Figure 9D:
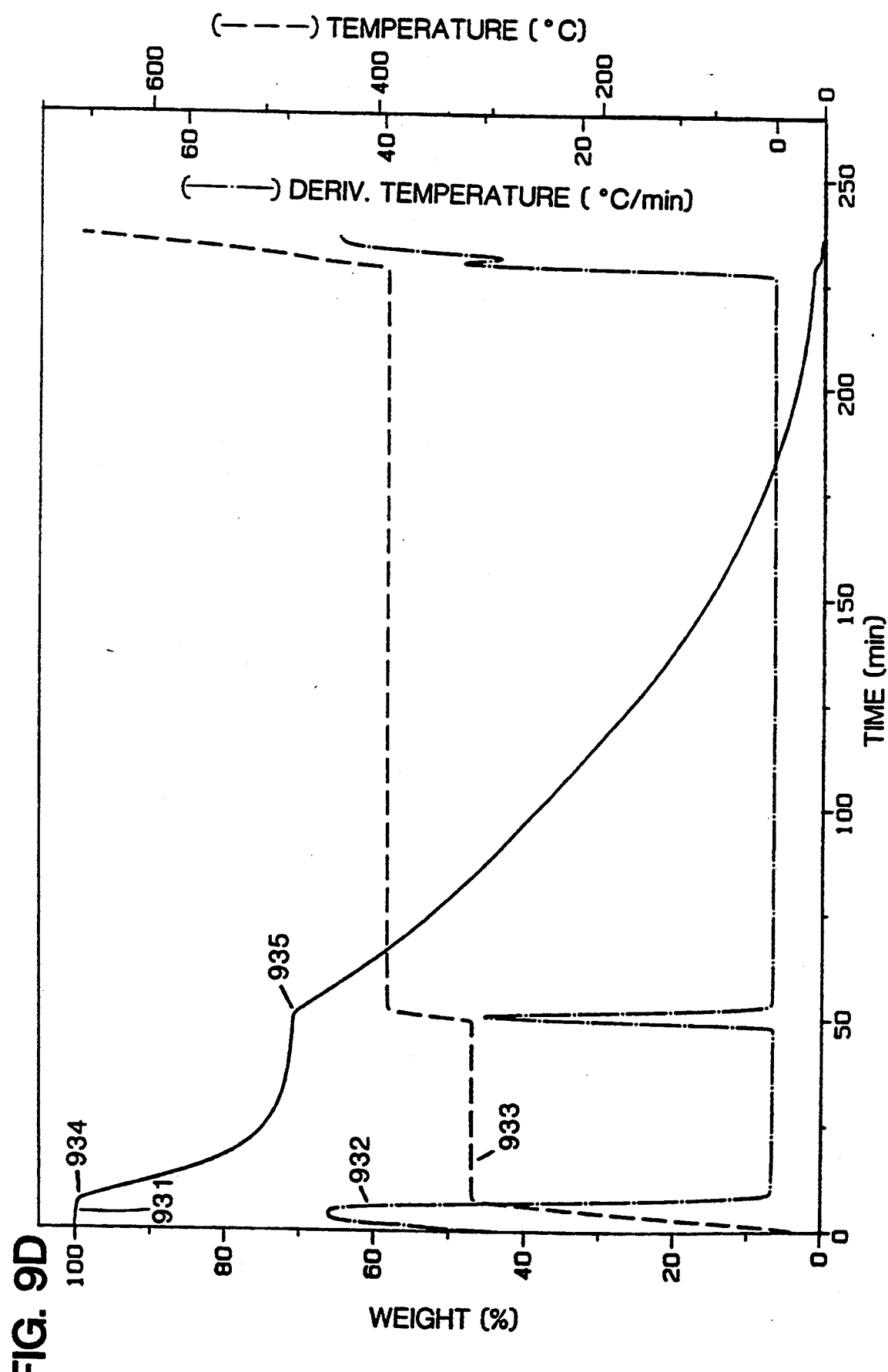

Samples of ethylene-vinyl acetate (EVA) copolymer with 40% vinyl acetate (the same material as was used in Example 6) were examined by the method (steps 1–14) of the second preferred embodiment of the present invention to compare the results obtained by each mode of the present invention with the scans of Example 6. The experimental procedures followed in this example for preparing the apparatus, loading the samples, and running analyses were described in Example 1. In FIGS. 9*a* and 9*b*, a 9.9-milligram sample of EVA was analyzed in nitrogen, from ambient temperature to 680° C., using the first mode of operation (steps 1–14) of the second preferred embodiment of the present invention at a maximum heating rate of 50° C./minute and at a resolution setting of 5.0. In FIGS. 9*c* and 9*d*, an 8.5 milligram sample of EVA was analyzed in nitrogen, from ambient temperature to 660 degrees Celsius, using the second mode of operation (steps 1–14) of the second preferred embodiment of the present invention at a maximum heating rate of 50° C./minute and at a resolution setting of −4.0.

FIGS. 9*a* and 9*c* show the TGA data plotted versus temperature. Curves 901 (FIG. 9*a*) and 921 (FIG. 9*c*) are plots of the percent weight change of the sample as a function of sample temperature. Curves 902 (FIG. 9*a*) and 922 (FIG. 9*c*) are plots of the derivative with respect to time of the sample temperature as a function of sample temperature. Curves 903 (FIG. 9*a*) and 923 (FIG. 9*c*) are plots of the derivative with respect to temperature of the percent weight change of the sample as a function of sample temperature.

FIGS. 9*b* and 9*d* show the TGA data plotted versus time. Curves 911 (FIG. 9*b*) and 931 (FIG. 9*d*) are plots of the percent weight change of the sample as a function of time. Curves 912 (FIG. 9*b*) and 932 (FIG. 9*d*) are plots of the derivative with respect to time of the sample temperature as a function of time. Curves 913 (FIG. 9*b*) and 933 (FIG. 9*d*) are plots of the sample temperature as a function of time.

The scans in FIGS. 9*a*, 9*b*, 9*c*, and 9*d* can be readily compared in the same manner as in Example 8 to the constant heating rate scans in FIGS. 6*a*, 6*b*, 6*e*, and 6*f*, respectively, and to the high resolution scans in FIGS. 6*c* and 6*d*. It is clear from this comparison that the two weight loss transitions, features 904 and 905 in FIG. 9*a*, and features 924 and 925 in FIG. 9*c* are better resolved than their respective features in FIGS. 6*a* and 6*e*. In all cases the derivative of weight change (percent/°C.) curves are sharper and better resolved with respect to the baseline compared to the same curves shown in FIGS. 6*a* and 6*e*.

EXAMPLE 10: COMPUTER PROGRAM FOR IMPLEMENTING THE SECOND PREFERRED EMBODIMENT OF THE PRESENT INVENTION

The following computer program is an example of a computer program used to control the main steps of the second preferred embodiment of the present invention. Examples 8 and 9 were implemented using a similar computer program. The program used to implement Examples 8 and 9 differed from the program listed here only in minor respects, such as the names of some variables. The program is written in PL/M.

```
Heating Rate Control Program - 2

/* High Resolution TGA Heating Rate Set Point
   Determination Algorithm. This Algorithm executes
   once every 0.5 seconds. */
/* Definitions of variables used in the heating rate
   control program.
   res_setting        current resolution setting
                      (−8.0 to 8.0)
   res_factor         resolution factor ((4**res)/256)
   wgt_pct            real time weight change (percent)
   pct_drv            derivative of wgt_pct with respect
                      to time (percent/minute)
   pct_drv_avg        average derivative of wgt_pct with
                      respect to time (percent/minute)
   mode2_pct_min      minimum percent/minute for
                      mode 2 operation (percent/minute)
   drv_delay_ctr      time delay counter for pct_drv_avg
                      calculation
   rate_max           maximum heating rate (deg C./minute)
   rate_min           minimum heating rate (deg C./minute)
   rate_now           current heating rate (deg C./minute)
   rate_drv_pct       new heating rate computed from
                      real-time percent/minute (deg
                      C./minute)
   rate_drv_avg       new heating rate computed from
                      average percent/minute (deg
                      C./minute)
   rate_new           resultant new heating rate (deg
                      C./minute) */
   Do
/* STEP 1 */
   /* The maximum heating rate in °C./minute is
      selected by the operator prior to the start of the
      experiment and is stored by the computer in
      variable "rate_max". */
/* STEP 2 */
   /* The resolution setting (range −8.0 to 8.0) is
      selected by the operator prior to the start of the
      experiment and is stored by the computer in
      variable "res_setting". */
/* STEP 3 */
   /* The absolute weight change as a percent of
      initial weight is monitored by the computer in
      real time and stored in "wgt_pct". */
/* STEP 4 */
   /* The derivative of the weight change with
      respect to time is calculated by the computer in
      real time and stored in "pct_drv". */
/* STEP 5 */
   /* Compute the resolution factor from the
      resolution setting. The resolution factor is used
      in subsequent calculations and is defined to be 4
      raised to the x power divided by 256, where x is
      the absolute value of the resolution setting. (4
      to the x power can be implemented as e raised to
      the x power times the natural logarithm of 4.) */
   res_factor = EXP(ABS(res_setting) * LN(4.0)) /
                256.0;
/* STEP 6 */
   /* Compute the minimum mode 2 %/minute for the
```

-continued

Heating Rate Control Program - 2

```
         current resolution setting. Lowest minimum occurs
         at highest resolution setting. */
         mode2_pct_min = 0.04 / res_factor;
/* STEP 7 */
         /* Compute the minimum Hi-Res heating rate
         allowed. If the resolution setting is less than
         zero then set the minimum to 0.01 deg/min to
         prevent the heater from drifting backward due to
         heater lag and control cycling during transitions
         in mode 2 operation. Otherwise, set the heating
         rate minimum to 0.0 deg/min since the heating rate
         will come close to but never reach zero during
         mode 1 operation. */
         If res_setting < 0.0 Then    /* Mode 2? */
                 rate_min = 0.01;    /* Mode 2 minimum */
         Else
                 rate_min = 0.0;     /* Mode 1 minimum */
/* STEP 8 */
         /* Delay calculation of the %/minute average to
         allow any ringing or overshoot in the weight %/min
         to dampen out. The average is computed with an
         exponential filter with a time constant of about
         50 seconds.
         (drv_delay_ctr is initialized to 30 prior to the
         start of the method.) */
         If drv_delay_ctr > 0 Then    /* delay? */
                 Do; /* Delay active */
                     drv_delay_ctr = drv_delay_ctr - 1;
                     pct_drv_avg = pct_drv;    /* Init drv average */
                 End;
         Else /* Compute average %/minute */
                 pct_drv_avg = pct_drv_avg * 0.99 + pct_drv *
                     0.01;
/* STEP 9 */
         /* Compute the new high resolution heating rates.
         The first rate (rate_drv_pct) is based on the
         real-time %/minute. The second rate
         (rate_drv_avg) is based on the average %/minute.
         Note: If a negative rate results it will be
         limited to the minimum. */
         If res_setting < 0.0 Then    /* Mode 2? */
                 Do;   /* Rates for mode 2 operation */
                     rate_drv_pct = rate_max * (2.0 -
                         EXP(ABS(pct_drv) * res_factor));
                     rate_drv_avg = rate_max *
                         (2.0-EXP(ABS(pct_drv_avg) * res_factor));
                 End;
         Else
                 Do;   /* Rates for mode 1 operation */
                     rate_drv_pct = rate_max / EXP(ABS(pct_drv) *
                         res_factor);
                     rate_drv_avg = rate_max /
                         EXP(ABS(pct_drv_avg) * res_factor);
                 End;
/* STEP 10 */
         /* Use the heating rate associated with the
         largest weight change per minute. */
         If ABS(pct_drv) > ABS(pct_drv_avg) Then rate_new =
             rate_drv_pct;
         Else
             rate_new = rate_drv_avg;
/* STEP 11 */
         /* If we are in mode 2 operation then check to see
         if we are currently holding the temperature to the
         minimum heating rate.
         If we are holding and the average %/minute is
         greater than the heating rate minimum then
         continue holding, otherwise, allow the heating
         rate to increase. */
         If res_setting < 0.0 And  /*    Mode 2? */
                 rate_now <= rate_min And     */ Holding Mode 2? */
                 ABS(pct_drv_avg) > mode2_pct_min
                 Then /* %/min > Min? */
                     rate_new = rate_min;   /* Continue holding*/
/* STEP 12 */
         /* Limit the new rate to the maximum rate allowed.
         */
         If rate_new > rate_max Then
                 rate_new = rate_max;
/* STEP 13 */
         /* Limit the new rate to the minimum rate allowed.
```

-continued

Heating Rate Control Program - 2

```
         */
         If rate_new < rate_min Then
                 rate_new = rate_min;
/* STEP 14 */
         /* Save the new heating rate for heater control.
         */
         rate_now = rate_new;
End;
```

The foregoing examples of computer programs for controlling the heating rate of the sample during thermogravimetric analysis are two of many algorithms that could be used to control the TGA apparatus. These algorithms could reside in the thermal analysis module or in a separate computer. The algorithms would be executed concurrently with other algorithms for controlling the system and analyzing data.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. An analytical method for determining a property of a material that undergoes at least one transition as a function of a driving variable comprising the steps of:

(a) placing a sample of the material in an apparatus for detecting changes in a characterizing physical parameter as a function of said driving variable;

(b) monitoring a signal representative of the characterizing physical parameter, as the driving variable is varied at a predetermined maximum rate of change;

(c) monitoring a signal baseline for the characterizing physical parameter in the signal representative of the characterizing physical parameter;

(d) detecting deviations of the signal representative of the characterizing physical parameter from the monitored signal baseline;

(e) decreasing the rate of change of the driving variable whenever said deviations from the signal baseline are detected;

(f) constraining the absolute value of the rate of change of the driving variable to always exceed or equal a minimum rate of change;

(g) monitoring the rate of change in the signal representative of the characterizing physical parameter;

(h) adjusting the rate of change of the driving variable according to the rate of change of the characterizing physical parameter to track a predetermined rate of change of the characterizing physical parameter;

(i) forcing the rate of change of the driving variable back to the predetermined maximum rate of change whenever the rate of change of the signal representative of the characterizing physical parameter falls below a predetermined minimum value; and (j) determining the property of the material from the detected changes in the characterizing physical parameter.

2. The analytical method of claim 1, wherein the analytical method is a thermal analytical method, and wherein the driving variable is temperature.

3. The analytical method of claim 2, wherein the analytical method is thermogravimetric analysis, and the characterizing physical parameter is the weight of the sample being analyzed.

4. The analytical method of claim 3, further comprising the step of analyzing constituents evolving from the sample using a downstream analytical technique.

5. The analytical method of claim 4, wherein the downstream analytical technique is mass spectroscopy.

6. The analytical method of claim 4, wherein the downstream analytical technique is Fourier transform infrared spectroscopy.

7. The analytical method of claim 4, wherein the downstream analytical technique is selected from the group consisting of infrared spectroscopy, atomic spectroscopy, molecular spectroscopy, computer-assisted dispersive infrared spectroscopy, laser diode spectroscopy, flame ionization detectors, Raman spectroscopy, thermal conductivity detectors, electron capture detectors, photoionization detectors, helium ionization detectors, discharge ionization detectors, flame photometric detectors, and chemiluminescent detectors.

8. The analytical method of claim 2, wherein the analytical method is selected from the group consisting of Differential Thermal Analysis (DTA), Differential Scanning Calorimetry (DSC), Pressure Differential Scanning Calorimetry (PDSC), Thermomechanical Analysis (TMA), Dynamic Mechanical Analysis (DMA), Dynamic Mechanical Spectrometry (DMS), Dielectric Analysis (DEA), Differential Photocalorimetry (DPC), and Thermal Conductivity Analysis (TCA).

9. An apparatus for determining a property of a material that undergoes at least one transition as a function of a driving variable comprising;
(a) means for detecting changes in a characterizing physical parameter of the material as a function of said driving variable;
(b) means for monitoring a signal representative of the characterizing physical parameter, as the driving variable is varied at a predetermined maximum rate of change;
(c) means for monitoring a signal baseline for the characterizing physical parameter in the signal representative of the characterizing physical parameter;
(d) means for detecting deviations of the signal representative of the characterizing physical parameter from the monitored signal baseline;
(e) means for decreasing the rate of change of the driving variable whenever said deviations from the signal baseline are detected;
(f) means for constraining the absolute value of the rate of change of the driving variable to always exceed or equal a predetermined minimum rate of change;
(g) means for monitoring the rate of change in the signal representative of the characterizing physical parameter;
(h) means for adjusting the rate of change of the driving variable according to the rate of change of the characterizing physical parameter to track a predetermined rate of change of the characterizing physical parameter; and
(i) means for forcing the rate of chance of the driving variable back to the predetermined maximum rate of change whenever the derivative of the characterizing physical parameter with respect to the driving variable falls below a predetermined minimum value.

10. The apparatus of claim 9, wherein the apparatus is a thermal analytical apparatus, and wherein the driving variable is temperature.

11. The apparatus of claim 10, further comprising means for analyzing constituents evolving from the material using a downstream analytical technique.

12. The apparatus of claim 10, wherein the apparatus is selected from the group consisting of Differential Thermal Analysis (DTA) apparatus, Differential Scanning Calorimetry (DSC) apparatus, Pressure Differential Scanning Calorimetry (PDSC) apparatus, Thermomechanical Analysis (TMA) apparatus, Dynamic Mechanical Analysis (DMA) apparatus, Dynamic Mechanical Spectrometry (DMS) apparatus, Dielectric Analysis (DEA) apparatus, Differential Photocalorimetry (DPC) apparatus, and Thermal Conductivity Analysis (TCA) apparatus.

13. An analytical method for determining a property of a material that undergoes at least one transition as a function of a driving variable by detecting changes in a characterizing physical parameter of the material comprising the steps of:
(a) selecting a maximum rate of change of the driving variable, a minimum rate of change of the driving variable, and a desired rate of change of the characterizing physical parameter;
(b) placing a sample of the material in an apparatus for detecting changes in the characterizing physical parameter as a function of said driving variable, and varying the driving variable at the maximum rate of change of the driving variable;
(c) monitoring a signal representative of the characterizing physical parameter;
(d) monitoring a signal baseline for the characterizing physical parameter in the signal representative of the characterizing physical parameter;
(e) detecting deviations of the signal representative of the characterizing physical parameter from the monitored signal baseline;
(f) controlling the rate of change of the driving variable according to changes in the signal representative of the characterizing physical parameter, subject to the maximum and minimum rates of change of the driving variable; and
(g) determining the property of the material from the detected changes in the characterizing physical parameter.

14. The analytical method of claim 13, wherein the analytical method is thermogravimetric analysis, and further comprising the step of analyzing constituents evolving from the sample using a downstream analytical technique.

15. The analytical method of claim 13, further comprising monitoring changes in the signal representative of the characterizing physical parameter, wherein the rate of change of the driving variable is controlled such that when the percent change per unit time of the signal representative of the characterizing physical parameter is small, the rate of change of the driving variable approaches the maximum rate of change of the driving variable, and when the percent change per unit time of the signal representative of the characterizing physical parameter is large, the rate of change of the driving variable approaches the minimum rate of change of the driving variable.

16. The analytical method of claim 13, wherein the step of controlling the rate of change of the driving variable according to changes in the signal representing the characterizing physical parameter comprises controlling the rate of change of the driving variable such that the actual rate of change of the signal representing the characterizing physical parameter tracks a predetermined rate of change of the characterizing physical parameter.

17. The analytical method of claim 13, wherein the analytical method is a thermal analysis method, and the driving variable is temperature.

18. A method for determining a property of a material using thermogravimetric analysis, comprising the steps of:
  (a) placing a sample of the material in a thermogravimetric apparatus having means for detecting changes in the weight of the sample as a function of the temperature of the sample, and means for controlling the rate of change of the temperature of the sample;
  (b) monitoring a signal representative of the weight of the sample as the temperature of the sample is increased at a predetermined maximum rate of change;
  (c) monitoring a signal baseline for the weight of the sample as a function of the temperature of the sample in the signal representative of the weight of the sample;
  (d) detecting deviations of the signal representative of the weight of the sample from the monitored signal baseline;
  (e) decreasing the rate of change of the temperature of the sample whenever said deviations from the signal baseline are detected;
  (f) constraining the absolute value of the rate of change of the temperature of the sample to always exceed or equal a minimum rate of change;
  (g) monitoring the rate of change in the signal representative of the weight of the sample;
  (h) adjusting the rate of change of the temperature of the sample according to the rate of change of the weight of the sample to track a predetermined rate of change of the weight of the sample;
  (i) forcing the rate of change of the temperature of the sample back to the predetermined maximum rate of change whenever the rate of change of the weight of the sample with respect to the temperature of the sample falls below a predetermined minimum value; and
  (j) determining the property of the material from the detected changes in the weight of the sample.

19. An apparatus for determining a property of a sample of a material that undergoes at least one transition as a function of temperature comprising:
  (a) means for increasing the temperature of the sample at a predetermined maximum heating rate;
  (b) means for detecting changes in the weight of the sample as a function of the temperature of the sample;
  (c) means for monitoring a signal representative of the weight of the sample;
  (d) means for monitoring a signal baseline for the weight of the sample as a function of the temperature of the sample;
  (e) means for detecting deviations from the signal baseline in the monitored signal representative of the weight of the sample with reference to the monitored signal baseline;
  (f) means for decreasing the heating rate of the sample from the initial predetermined heating rate when deviations from the signal baseline are detected;
  (g) means for constraining the absolute value of the heating rate of the sample to always exceed or equal a predetermined minimum heating rate;
  (h) means for adjusting the heating rate of the sample according to the rate of change of the weight of the sample to track a predetermined rate of change of the weight of the sample;
  (i) means for monitoring the change in weight of the sample; and
  (j) means for forcing the heating rate of the sample to the predetermined maximum heating rate whenever the rate of change of the weight of the sample with respect to the temperature of the sample falls below a predetermined minimum value.

20. An analytical method for determining a property of a material using thermogravimetric analysis comprising the steps of:
  (a) selecting a minimum heating rate, and a maximum heating rate, wherein the minimum heating rate is greater than zero;
  (b) placing a sample of the material in a thermogravimetric apparatus having means for detecting changes in the weight of the sample as a function of the temperature of the sample, and means for controlling the temperature of the sample and the heating rate of the sample;
  (c) raising the temperature of the sample at the maximum heating rate;
  (d) monitoring a signal representative of the weight of the sample;
  (e) monitoring a signal baseline for the weight of the sample;
  (f) detecting deviations from the signal baseline in the monitored signal representative of the weight of the sample with reference to the monitored signal baseline;
  (g) controlling the heating rate according to changes in the signal representative of the weight of the sample when said deviations from the signal baseline are detected;
  (h) holding the heating rate to the minimum heating rate;
  (i) detecting a return to a baseline region in the signal representative of the weight of the sample;
  (j) increasing the heating rate of the sample to the maximum heating rate; and
  (k) determining the property of the material from the detected changes in the weight of the sample.

21. The analytical method of claim 20, further comprising the step of analyzing constituents evolving from the sample using a downstream analytical technique.

22. An analytical method for determining a property of a material that undergoes at least one transition as a function of temperature comprising the steps of:
  (a) placing a sample of the material in a thermogravimetric apparatus having means for detecting the weight of the sample as a function of the temperature of the sample, said apparatus having means for controlling the temperature and heating rate of the sample;

(b) selecting a maximum allowed value for the heating rate of the sample;
(c) selecting a minimum allowed value for the heating rate of the sample;
(d) selecting a desired constant change of weight of the sample;
(e) raising the temperature of the sample at the maximum heating rate;
(f) monitoring a signal representative of the weight of the sample;
(g) monitoring a signal baseline for the weight of the sample;
(h) detecting deviations from the signal baseline in the monitored signal representative of the weight of the sample with reference to the monitored signal baseline;
(i) decreasing the heating rate of the sample to track the desired constant change of weight of the sample when said deviations from the signal baseline are detected, subject to not reducing the heating rate to a value below the minimum allowed value of the heating rate of the sample;
(j) detecting a return to a baseline region in the signal representative of the weight of the sample;
(k) increasing the heating rate of the sample to the maximum heating rate; and
(l) determining the property of the material from the detected changes in the weight of the sample.

23. The analytical method of claim 22, further comprising the step of analyzing constituents evolving from the sample using a downstream analytical technique.

* * * * *